(12) United States Patent
Kawamoto et al.

(10) Patent No.: US 10,620,108 B2
(45) Date of Patent: Apr. 14, 2020

(54) METHOD OF PROCESSING SPECIMEN AND SPECIMEN PROCESSING APPARATUS

(71) Applicant: SYSMEX CORPORATION, Kobe-shi, Hyogo (JP)

(72) Inventors: Yasuko Kawamoto, Kobe (JP); Ayato Tagawa, Kobe (JP)

(73) Assignee: SYSMEX CORPORATION (JP)

(*) Notice: Subject to any disclaimer, the term of this patent is extended or adjusted under 35 U.S.C. 154(b) by 190 days.

(21) Appl. No.: 15/825,965

(22) Filed: Nov. 29, 2017

(65) Prior Publication Data

US 2018/0149574 A1 May 31, 2018

(30) Foreign Application Priority Data

Nov. 30, 2016 (JP) .................. 2016-232094

(51) Int. Cl.
*G01N 15/14* (2006.01)
*B03C 1/28* (2006.01)
(Continued)

(52) U.S. Cl.
CPC .... *G01N 15/1404* (2013.01); *B01L 3/502761* (2013.01); *B03C 1/288* (2013.01);
(Continued)

(58) Field of Classification Search
CPC ....... B01L 2200/027; B01L 2200/0647; B01L 2200/0673; B01L 2400/0487;
(Continued)

(56) References Cited

U.S. PATENT DOCUMENTS

2002/0058332 A1* 5/2002 Quake ................ G01N 15/1459
435/288.5
2007/0242105 A1* 10/2007 Srinivasan .......... B01F 13/0071
347/63
(Continued)

FOREIGN PATENT DOCUMENTS

WO  WO 02/23163     3/2002
WO  WO 2010/148339  12/2010
(Continued)

OTHER PUBLICATIONS

The Communication pursuant to Article 94(3) EPC dated Feb. 13, 2019 in a counterpart European patent application No. 17204025.5.
(Continued)

*Primary Examiner* — Jennifer Wecker
(74) *Attorney, Agent, or Firm* — Brinks Gilson & Lione

(57) ABSTRACT

Disclosed is a method of processing a specimen in which a target component in a specimen is processed using a specimen processing chip provided with a flow-path, the method including: introducing a fluid into a flow-path to form an interface that divides the fluid from a process liquid used for the processing of the target component with a rim of the interface on an inner wall of the flow-path, the process liquid containing particles including the target component; and moving the formed interface along the flow-path with the rim of the interface on the inner wall so as to force out the particles retained in the process liquid by the fluid.

20 Claims, 29 Drawing Sheets

(51) Int. Cl.
*C12N 15/10* (2006.01)
*B01L 3/00* (2006.01)
*G01N 33/543* (2006.01)
*G01N 35/00* (2006.01)
*G01N 35/08* (2006.01)
G01N 15/10 (2006.01)
G01N 35/10 (2006.01)

(52) U.S. Cl.
CPC ..... *G01N 15/1459* (2013.01); *G01N 15/1484* (2013.01); *G01N 33/54326* (2013.01); *G01N 35/00069* (2013.01); *G01N 35/0098* (2013.01); *G01N 35/085* (2013.01); *B01L 3/50273* (2013.01); *B01L 3/502784* (2013.01); *B01L 2200/027* (2013.01); *B01L 2200/0647* (2013.01); *B01L 2200/0673* (2013.01); *B01L 2400/0487* (2013.01); *B03C 2201/18* (2013.01); *G01N 2015/1006* (2013.01); *G01N 2015/1409* (2013.01); *G01N 2015/1415* (2013.01); *G01N 2015/1486* (2013.01); *G01N 2035/00158* (2013.01); *G01N 2035/00237* (2013.01); *G01N 2035/1034* (2013.01)

(58) Field of Classification Search
CPC ........... B01L 3/50273; B01L 3/502761; B01L 3/502784; B03C 1/288; B03C 2201/18; G01N 15/1404; G01N 15/1459; G01N 15/1484; G01N 2015/1006; G01N 2015/1409; G01N 2015/1415; G01N 2015/1486; G01N 2035/00158; G01N 2035/00237; G01N 2035/1034; G01N 33/54326; G01N 35/00069; G01N 35/0098; G01N 35/085
See application file for complete search history.

(56) References Cited

U.S. PATENT DOCUMENTS

2007/0243523 A1* 10/2007 Ionescu-Zanetti .......................... B01L 3/502738
435/4
2008/0003142 A1* 1/2008 Link .................... B01F 3/0807
422/82.08
2008/0073545 A1 3/2008 Akashi et al.
2011/0120562 A1 5/2011 Tan et al.
2014/0371107 A1* 12/2014 Curran ................ B01F 13/0071
506/26

FOREIGN PATENT DOCUMENTS

WO WO 2013/096643 6/2013
WO WO 2013/111016 8/2013

OTHER PUBLICATIONS

The Communication pursuant to Article 94(3) EPC dated Oct. 1, 2019 in a counterpart European patent application No. 17204025.5.

* cited by examiner

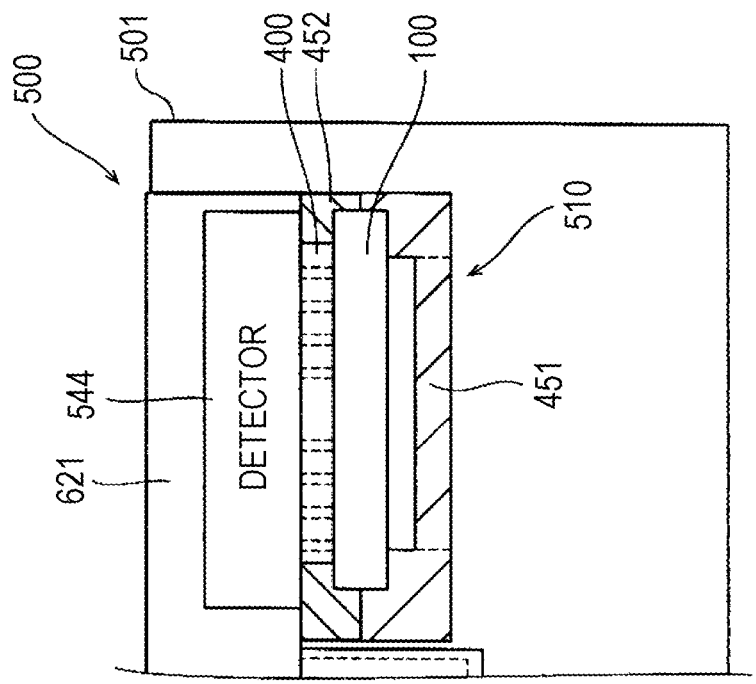
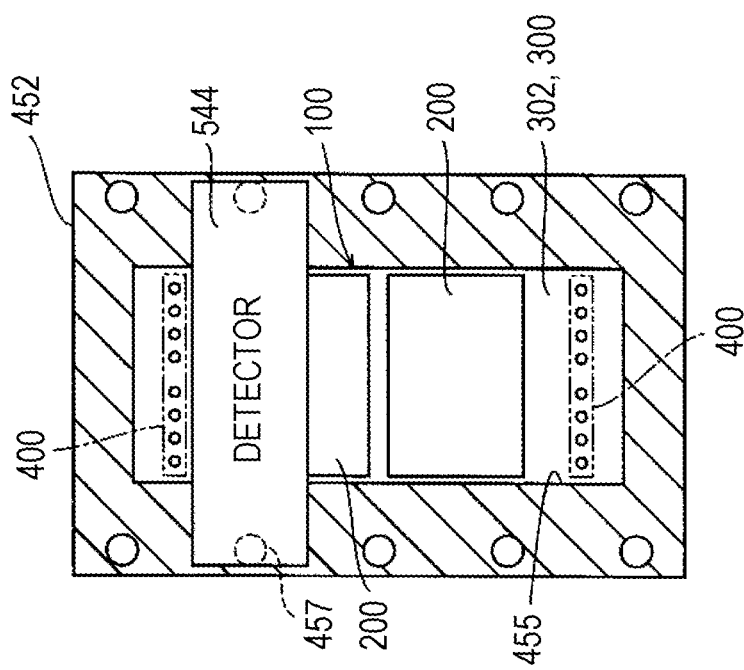

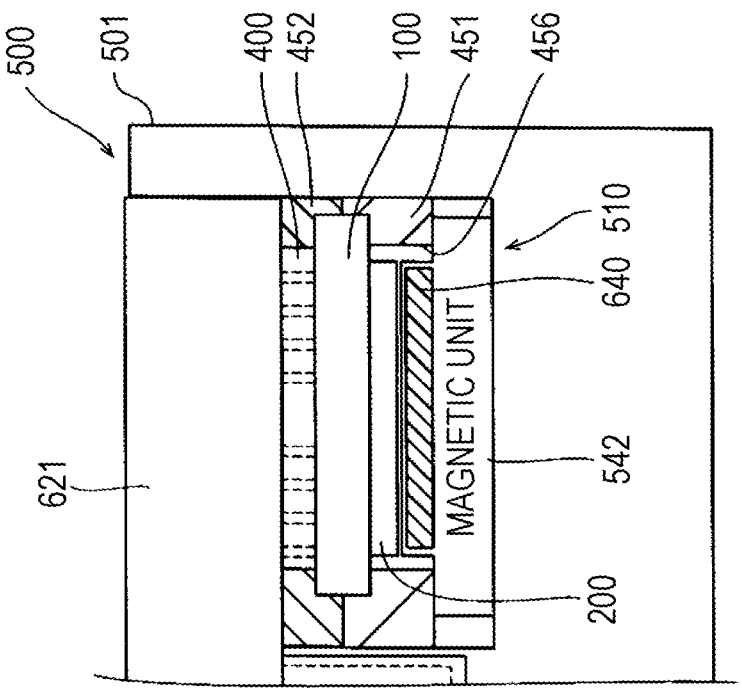
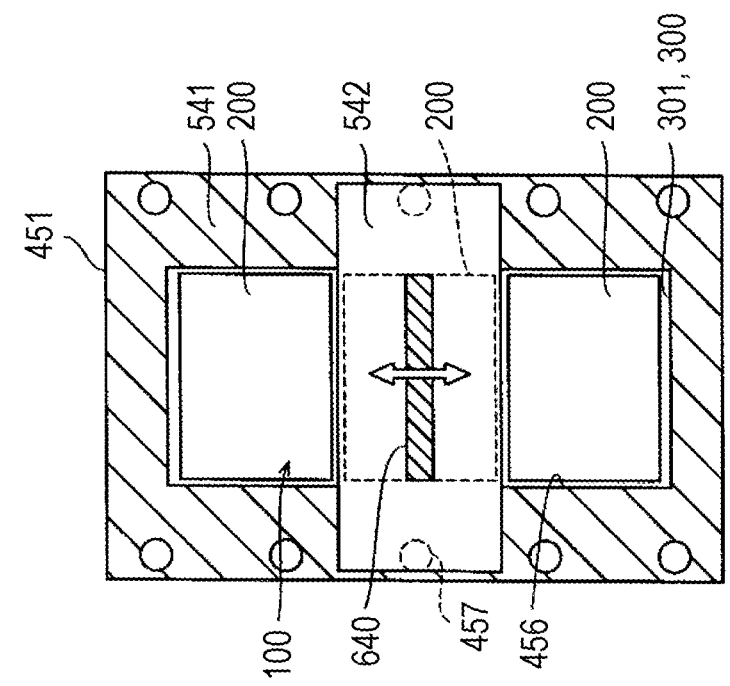
FIG. 30A
FIG. 30B

METHOD OF PROCESSING SPECIMEN AND SPECIMEN PROCESSING APPARATUS

RELATED APPLICATIONS

This application claims priority from prior Japanese Patent Application No. 2016-232094 filed on Nov. 30, 2016, entitled "Method of processing specimen and specimen processing apparatus," the entire contents of which are incorporated herein by reference.

BACKGROUND OF THE INVENTION

1. Field of the Invention

The present invention relates to a method of processing a specimen using a specimen processing chip provided with a flow-path, and a specimen processing apparatus.

2. Description of the Related Art

In a conventional specimen processing chip (see US 2008/073,545 A, for example), a target component included in a specimen is processed in a flow-path. The target component is transferred to a desired place in the flow-path while, before, or after processing the target component. US 2008/073,545 A discloses a micro-reactor provided with a micro-flow-path 900 in which magnetic particles 901 carrying enzyme, for example, introduced into the micro-flow-path 900 are magnetically moved or caught at a desired place by a magnet 902 provided outside the micro-flow-path 900. In the art disclosed in US 2008/073,545 A, after the processing of the target component, the magnetic particles 901, which have been caught in a flowing liquid, are released by removing the magnet 902 and moved outside the micro-flow-path 900.

The inventors have found through the studies that such a method of moving particles, such as magnetic particles, including the target component by supplying a flowing liquid in a micro-flow-path as disclosed in US 2008/073,545 A causes some particles to remain in the micro-flow-path, which makes it difficult to obtain a sufficient amount of particles to be transferred or collected. The method disclosed in in US 2008/073,545 releases the magnetic particles in the flowing liquid to move the magnetic particles. However, the inventors have found that the magnetic particles retained in the micro-flow-path continue to remain in the micro-flow-path even after removing the magnet and supplying a flowing liquid in the micro-flow-path.

In such a method of moving the particles by the liquid flowing in the flow-path of a specimen processing chip, it is difficult to move the particles because, for example, the velocity of the flowing liquid is usually low near the inner wall of the flow-path and causes the particles to adhere and aggregate on the wall. It is therefore desired to avoid remaining of particles in the flow-path.

SUMMARY OF THE INVENTION

The scope of the present invention is defined solely by the appended claims, and is not affected to any degree by the statements within this summary.

The inventors have made efforts to solve the aforementioned problem and found out that by moving particles in a process liquid in a flow-path by moving an interface formed in a flow-path with the rim of the interface on the inner wall of the flow-path, remaining of the particles in the flow-path can be avoided. A first aspect of the present invention is a method of processing a specimen in which a target component (20) in a specimen is processed using a specimen processing chip (100) provided with a flow-path (201), the method including: introducing a fluid (24) into the flow-path (201) to form an interface (23) that divides the fluid (24) from a process liquid (21) used for processing the target component (20) with a rim of the interface (23) on an inner wall (11) of the flow-path (201), the process liquid (21) containing particles (22) including the target component (20); and moving the interface (23) along the flow-path (201) with the rim of the interface (23) on the inner wall (11) to force out the particles (22) retained in the process liquid (21) by the fluid (24). The term "particle" means not only a solid particle but a liquid particle formed of liquid. The term "fluid" means a gas or a liquid.

In the method of processing a specimen according to the first aspect, the fluid (24) is introduced into the flow-path (201) to form an interface (23) that divides the fluid (24) from the process liquid (21) used for processing the target component (20), the process liquid (21) containing particles (22) including the target component (20), the rim of the interface (23) being on an inner wall (11) of the flow-path (201), and the interface (23) is moved by the fluid (24) along the flow-path (201) with the rim of the interface (23) on the inner wall (11) to force out the particles (22) retained in the process liquid (21). When the particles (22) in the process liquid (21) are retained during the processing of the target component (20) in the flow-path (201), the interface (23) having the rim on the inner wall (11) can be formed to divide the process liquid (21) from the fluid (24) by the fluid (24) introduced into the flow-path (201). Then, the interface (23) is moved along the flow-path (201) with the rim of the interface (23) on the inner wall (11) to forcibly convey the particles (22) retained in the flow-path (201) together with the process liquid (21). This avoids remaining of the particles (22) including the target component (20) in the flow-path (201) in which the target component (20) is processed, where the flow-path (201) is provided in the specimen processing chip (100).

In the method of processing a specimen according to the first aspect, the particles (22) retained in the process liquid (21) and forced out of the specimen processing chip (100) preferably by the fluid (24). In such a manner, the process liquid (21) in the downstream of the interface (23) can be forced out of the specimen processing chip (100) together with the retained particles (22), which enables collecting a large number of particles (22) while suppressing the increase in the amount of a sample collected from the specimen processing chip (100) compared to, for example, a method in which a great amount of the process liquid (21) is introduced in the flow-path (201) to force out the retained particles (22).

Preferably, the particles (22) forced out of the specimen processing chip (100) are counted by a flow cytometer (40). The increase in the amount of the sample finally collected from the specimen processing chip (100) is suppressed and thereby the concentration of the particles (22) in the collected sample can be raised. Therefore, no additional processing is necessary to condense the sample to a concentration suitable for counting using the flow cytometer (40).

In the method of processing a specimen according to the first aspect, the number of particles (22) in the process liquid (21) is preferably from 100 thousand to 10 million. For such a large number of particles (22), the collection rate of the particles (22) including the target component (20) can be raised by using the method that avoids remaining of the particles (22) in the flow-path (201), and thereby measurement sensitivity can be improved.

In the method of processing a specimen according to the first aspect, the process liquid (21) preferably includes a water phase liquid and an oil phase liquid. In this case, when either of the water phase liquid or the oil phase liquid adheres to the inner wall (11) of the flow-path (201), an interface formed between the phases traps the particles (22) between the water phase liquid and the oil phase liquid to easily cause the particles (22) to be retained near the inner wall (11). Moving the particles (22) retained on the inner wall (11) by moving the interface (23) along the flow-path (201) with the rim of the interface (23) on the inner wall (11) is effective when using the process liquid (21) including the water phase liquid and the oil phase liquid.

In the method of processing a specimen according to the first aspect, the particles (22) retained on the inner wall (11) of the flow-path (201) are moved away from the inner wall (11) to be conveyed along the flow-path (201) preferably by moving the interface (23) along the flow-path (201). In this manner, the particles (22) retained on the inner wall (11) of the flow-path (201) is forced away from the inner wall (11) and moved by the approaching interface (23). This effectively avoids remaining of the particles (22) in the flow-path (201) even for such a case where the particles (22) are retained on the inner wall (11) of the flow-path (201) in which the flow velocity is very small and thus conveyance of the particles (22) is difficult.

In this case, the interface (23) is preferably moved along the flow-path (201) so that the interface (23) contacts the particles (22) retained on the inner wall (11) to move the particles (22) away from the inner wall (11). In this manner, the moving interface (23) contacts the particles (22) adhering to the inner wall (11) of the flow-path (201) and applies a force that rips off the particles (22) from the inner wall (11). As a result, even for the particles (22) adhering to the inner wall (11) of the flow-path (201), remaining of the particles (22) in the flow-path (201) can further effectively be avoided.

In the method of processing a specimen according to the first aspect, the interface (23) of the fluid (24) is moved back and forth along the inner wall (11) preferably in a region where the particles (22) in the flow-path (201) are retained. The term "region where the particles are retained" means a region where the particles (22) may possibly be retained during the processing, which may be a local region in the flow-path (201) or the entire region of the flow-path (201). In this manner, the interface (23) moving back and forth contacts the particles (22) adhering to the inner wall (11) of the flow-path (201) and repetitively applies a force to the particles (22). As a result, remaining of the particles (22) in the flow-path (201) can further effectively be avoided.

In the method of processing a specimen according to the first aspect, the particle (22) including the target component (20) is preferably a liquid particle (25) including the target component (20). In such a case, when the liquid particles (25) including the target component (20) are contained in the process liquid (21), the liquid particles (25) retained in the flow-path (201) can forcibly be conveyed by the interface (23). Consequently, remaining of the liquid particles (25), which are particles (22) other than solid particles such as magnetic particles (26a), in the flow-path (201) can effectively be avoided. By conveying the retained liquid particles (25) by the moving interface (23), the chances of an excessive force acting on the liquid particles (25) in order to avoid remaining of the liquid particles (25) are small.

In the method of processing a specimen according to the first aspect, the particle (22) including the target component (20) is preferably a solid carrier (26) surficially bonded to the target component (20). Such carriers (26) bonded to the target component (20) in the specimen easily aggregate and therefore easily adhere to the inner wall (11) of the flow-path (201). Remaining of the carriers (26) in the flow-path (201) can effectively be avoided.

Preferably, in this case, the processing of the target component (20) includes catching the carriers (26) in the flow-path (201) followed by releasing the carriers (26) and moving the carriers (26) by the interface (23) of the fluid (24). The carriers (26) caught in the flow-path (201) may easily aggregate and settle or adhere to the inner wall (11). After the carriers (26) are released as described above, the interface (23) of the fluid (24) moves the released carriers (26), which are easily retained in the flow-path (201), and thereby effectively avoids remaining of the carriers (26) in the flow-path (201).

More preferably, in this case, the carriers (26) are magnetic particles (26a). The magnetic particles (26a) in the flow-path (201) are magnetically caught and, after releasing the magnetic particles (26a) from a magnetic force, the magnetic particles (26a) are moved by the interface (23) of the fluid (24). In this manner, the magnetic particles (26a) once magnetically caught adhering to the inner wall (11) of the flow-path (201) can be moved away from the inner wall (11) by the interface (23) of the fluid (24). As a result, remaining of the magnetic particles (26a), once caught on the inner wall (11), in the flow-path (201) can effectively be avoided.

In the method of processing a specimen according to the first aspect, the particles (22) and the process liquid (21) preferably have different specific gravities and the outer diameter of the particle (22) is preferably from 0.1 μm to 0.1 mm. Such particles (22) of a very small size go down to the bottom in the process liquid (21) or go up to the top in the flow-path (201). The particles (22) are easily retained near the inner wall (11) in the bottom side or the top side in the flow-path (201). For such particles (22) that are easily retained on the inner wall (11) in the bottom side or the top side in the flow-path (201), the particles (22) can be conveyed by the interface (23), which effectively avoids remaining of the particles (22) in the flow-path (201). The outer diameter of the particle (22) means the average particle diameter, which is the average of particle diameters measured by a light scattering method.

In the method of processing a specimen according to the first aspect, the fluid (24) is preferably a gas. Using a gas as the fluid (24), the interface (23) can easily be formed for various types of the process liquid (21). Unlike using a liquid as the fluid (24), the liquid amount in the flow-path (201) does not increase, and thus the increase in the liquid amount of the finally collected sample containing the particles (22) including the target component (20) is suppressed. Therefore, no additional processing to condense the target component (20) is necessary after collecting the sample.

In this case, the fluid (24) is preferably air. Unlike using a specific gas other than air as the fluid (24), the air as the fluid (24) can be obtained easily and introduced into the flow-path (201).

In the method of processing a specimen according to the first aspect, it is preferable that the particles (22) and the process liquid (21) are supplied from a flow-in joint (12) provided on an end of the flow-path (201), the target component (20) included in the particles (22) is processed in a channel (202) of the flow-path (201), and the particles (22) that have been processed and the process liquid (21) are conveyed to a flow-out joint (14) provided on the other end of the flow-path (201). In this configuration, the particles (22) and the process liquid (21) simply flow from an end to the other end of the flow-path (201) and no back and forth motion of the particles (22) and the process liquid (21) is required. The fluid (24) is simply introduced from one end to flow to the other end of the flow-path (201), which makes conveyance of the particles (22) easy.

The channel (202) preferably has a flow-path width (W1) larger than a flow-path width (W2) at the joints (12 and 14). Configured in such a manner, the channel (202) which has relatively large flow-path width in the flow-path (201) can be provided. Thus, the particles (22) can be distributed across the channel (202), in the width direction, to contact the process liquid (21) so that the target component (20) can efficiently be processed. The particles (22) retained in the channel (202) can efficiently be conveyed by the interface (23) because the fluid (24) adjusts its form along the cross section of the flow-path (201).

The channel (202) provided in the flow-path (201) preferably has a cross section having a width (W1) larger than a height (H1). The channel (202) has a flat cross section which is wide in the width direction. The particles (22) are therefore planarly distributed across the channel (202) to efficiently contact the process liquid (21), so that the target component (20) can efficiently be processed. The particles (22) retained in the channel (202) can efficiently be conveyed by the interface (23) because the fluid (24) adjusts its form along the cross section of the flow-path (201).

The channel (202) provided in the flow-path (201) preferably has a channel cross sectional area (Ac) from 0.01 $\mu m^2$ to 10 $mm^2$. The "channel cross sectional area" is the area of a cross section of the channel (202) normal to the flow direction of the liquid. The flow-path (201) having the channel (202) of such a size is generally referred to as a micro-flow-path. The flow-path (201) having a small cross sectional area allows only a small amount of liquid to flow through the flow-path (201) so that the total amount of the target component (20) is small. Thus, remaining of the particles (22) in the flow-path (201) results in reduction in the collection rate of the finally collected sample. Moving the interface (23) is effective for such a micro-flow-path to avoid remaining of the particles (22).

In the method of processing a specimen according to the first aspect, the target component (20) is preferably processed in a laminar flow in the flow-path (201). In a laminar flow unlike a disturbed flow in which the liquid is mixed and flows in random directions, the flow velocity closer to the inner wall (11) of the flow-path (201) is smaller. Thus, in a laminar flow, the particles (22) are easily retained in the flow-path (201). For the processing of the target component (20) in a laminar flow as described above, moving the interface (23) is effective to avoid remaining of the particles (22).

In the method of processing a specimen according to the first aspect, the target component (20) is preferably processed in a flow of a Reynolds number of 2000 or below in the flow-path (201). More preferably, the target component (20) is processed in a flow of a Reynolds number of 100 or below in the flow-path (201). More preferably, the target component (20) is processed in a flow of a Reynolds number of 10 or below in the flow-path (201). The Reynolds number Re is defined by Equation (1) expressed below.

$$Re = V \times d / \nu \quad (1)$$

V m/s is the average flow velocity in the flow-path (201), d m is the inner diameter of the flow-path (201), and $\nu$ $m^2/s$ is the dynamic viscosity of the fluid.

Generally, the flow of a Reynolds number Re of 2300 or below is a laminar flow. For a flow in the flow-path (201), the Reynolds number is smaller for a smaller inner diameter and a smaller flow velocity, so that in a flow of a smaller Reynolds number, the particles (22) are more easily retained in the flow-path (201). For the processing of the target component (20) in a flow of such a small Reynolds number, moving the interface (23) is effective to avoiding remaining of the particles (22). It is further effective in particular for a flow of a smaller Reynolds number in which the particles (22) are more easily retained.

In the method of processing a specimen according to the first aspect, the fluid (24) is introduced into the flow-path (201) at a flow-rate preferably of 0.1 μL/min to 5 mL/min. Under such a very small amount of flow-rate of 0.1 μL/min to 5 mL/min in a micro-flow-path, remaining of the particles (22) can effectively be avoided by moving the interface (23), without increasing the flow-rate of the fluid (24) by a large amount.

In the method of processing a specimen according to the first aspect, the fluid (24) introduced into the flow-path (201) preferably forms the interface (23) covering the entire flow-path cross section. The flow-path cross section is a cross section normal to the direction in which the liquid flows in the flow-path (201). By moving the interface (23), which completely covers the flow-path (201), along the inner wall (11), the particles (22) in the flow-path (201) are further surely conveyed.

In a case where the fluid (24) is air, it is preferable that a plurality of bubbles (27) each having an interface (23) containing air are formed in the flow-path (201), and the bubbles (27) are moved along the inner wall (11). The particles (22) in the flow-path (201) can be moved by the interface (23) formed of gathered bubbles (27). Remaining of the particles (22) in the flow-path (201) can also be avoided using the bubbles (27).

In the method of processing a specimen according to the first aspect, the fluid (24) is preferably interposed in the process liquid (21) in the flow-path (201) to form an interposed region (28) of the fluid (24), the interposed region (28) having interfaces (23) on both ends adjoining the process liquid (21). By simply interposing the fluid (24) in the flow of the process liquid (21), the two interfaces (23) are formed to divide the process liquid (21) from the fluid (24). By moving the interposed region (28) of the fluid (24) together with the process liquid (21), the particles (22) that the first interface (23) has failed to convey along the moving direction can be conveyed by the second interface (23). The conveyance efficiency of the interface (23) can thus be improved.

Preferably, the fluid (24) is intermittently interposed a plurality of times in the flow-path (201) to form a plurality of interposed regions (28). In this manner, the interfaces (23) are formed by twice the number of interposed regions (28) of the fluid (24). The conveyance efficiency of the interface (23) is further improved than forming a large single interposed region (28) by introducing the same amount of the fluid (24).

In the method of processing a specimen according to the first aspect, a valve (31) for introducing the fluid (24) into the flow-path (201) is preferably opened and closed to form the interfaces (23) of the fluid (24) in the flow-path (201) while or after the processing of the target component (20). The interfaces (23) of the fluid (24) can easily be formed by opening and closing a valve (522). By regulating the opened period and the number of opening and closing of the valve (522), the amount of the fluid (24) introduced and the number of interfaces (23) formed can be controlled. Interfaces suitable for the flow-path shape and the particles (22) can thus be formed.

Preferably, in this case, a valve (32) for introducing the particles (22) including the target component (20) into the flow-path (201) and the valve (33) for introducing the process liquid (21) into the flow-path (201) are each opened and closed to introduce the particles (22) and the process liquid (21) into the flow-path (201), and then the valve (31) for introducing the fluid (24) into the flow-path (201) is opened and closed to introduce the fluid (24) into the flow-path (201). In such a manner, introduction of the fluid (24) into the flow-path (201) can be regulated independent of introduction of the particles (22) and the process liquid (21). Interfaces suitable for the flow amount and flow velocity of the particles (22) and the process liquid (21) can thus be formed.

When the particles (22) are the solid carriers (26) surficially bonded to the target component (20), it is preferable that the target component (20) is nucleic acid, and the particles (22) are the carriers (26) bonded to the amplified nucleic acid as a result of amplifying nucleic acid, the amplified nucleic acid covering the surface of the carriers (26). With the nucleic acid covering the surface of the carriers (26), or the particles (22), the carriers (26) easily aggregate and adhere to the inner wall (11) of the flow-path (201). The carriers (26) bonded to the amplified nucleic acid, which are easily retained in the flow-path (201), can also be conveyed efficiently by moving the interface (23) along the inner wall (11), avoiding remaining of the carriers (26).

Preferably, in this case, the carriers (26) are the magnetic particles (26a), the process liquid (21) is a cleaning liquid, the processing of the target component (20) includes magnetically catching the magnetic particles (26a) in the flow-path (201), introducing the cleaning liquid into the flow-path (201) in which the magnetic particles (26a) are caught, and releasing the magnetic particles (26a). The fluid (24) is introduced into the flow-path (201) after cleaning the magnetic particles (26a) with the cleaning liquid to move the released magnetic particles (26a) by the interface (23) of the fluid (24). The magnetic particles (26a) of which surface covered with the amplified nucleic acid easily aggregate and adhere. Magnetically gathering and catching such magnetic particles (26a) further cause remaining of the magnetic particles (26a) in the flow-path (201). The released magnetic particles (26a) are moved by the interface (23) of the fluid (24), and remaining of the magnetic particles (26a), which are easily retained, can efficiently be avoided.

In the case described above where the target component (20) is nucleic acid and the particles (22) are the carriers (26) bonded to the amplified nucleic acid, it is preferable that the carriers (26) are the magnetic particles (26a), the process liquid (21) is the cleaning liquid, the processing of the target component (20) includes magnetically catching the magnetic particles (26a) in the flow-path (201), introducing a labeled matter for detecting the amplified nucleic acid in the flow-path (201) to form the magnetic particles (26a) including the labeled matter by reaction between the labeled matter and the amplified nucleic acid, and introducing the cleaning liquid into the flow-path (201) with the magnetic particles (26a) including the labeled matter kept caught to clean the magnetic particles (26a), and the fluid (24) is introduced into the flow-path (201) after cleaning the magnetic particles (26a) with the cleaning liquid to move the released magnetic particles (26a) by the interface (23) of the fluid (24). In this case, the magnetic particles (26a) are further easily retained in the flow-path (201) because the magnetic particles (26a), which are surficially bonded to the amplified nucleic acid and the labeled matter and aggregate and adhere easily, are magnetically gathered and caught. The released magnetic particles (26a) are moved by the interface (23) of the fluid (24), and remaining of the magnetic particles (26a), which are easily retained, can efficiently be avoided.

Preferably, in the case where the magnetic particles (26a) are cleaned with the cleaning liquid, the magnetic particles (26a) are magnetically caught and moved back and forth along the flow-path (201) in the cleaning liquid to be cleaned. In this manner, the magnetically gathered magnetic particles (26a) moved along the flow-path (201) can efficiently make contact with the cleaning liquid, which improves cleaning efficiency. Meanwhile, the magnetic particles (26a) are moved while being magnetically forced against the inner wall (11) of the flow-path (201) and therefore the magnetic particles (26a) further easily adhere to the inner wall (11). Nevertheless, moving the released magnetic particles (26a) by the interface (23) of the fluid (24) effectively avoids remaining of the magnetic particles (26a), which easily adhere to the inner wall (11).

Preferably, in the case where the particles (22) are liquid particles (25) including the target component (20), the target component (20) is nucleic acid, the processing of the target component (20) includes forming the liquid particles (25) in the process liquid (21) in the flow-path (201), the liquid particles (25) including a mixed liquid of nucleic acid, a reagent for amplification reaction of nucleic acid, and the carriers (26) that bonds to nucleic acid, and the liquid particles (25) are moved in the flow-path (201) by moving the interface (23) of the fluid (24). When the liquid particles (25) are formed in the process liquid (21) in the flow-path (201), the liquid particles (25) may adhere to the inner wall (11) and remain in the flow-path (201). By moving the liquid particles (25) formed in the process liquid (21) by the interface (23) of the fluid (24), remaining of the liquid particles (25) can efficiently be avoided.

Preferably, in the case where the particles (22) are liquid particles (25) including the target component (20), the target component (20) is nucleic acid, the processing of the target component (20) includes amplifying nucleic acid in the liquid particles (25) in the process liquid (21), the liquid particles (25) including a mixed liquid of nucleic acid, a reagent for amplification reaction of nucleic acid, and the carriers (26) that bond to nucleic acid, and the liquid particles (25) including the carriers (26) bonded to nucleic acid amplified by nucleic acid amplification are moved by moving the interface (23) of the fluid (24). Such nucleic acid amplification is performed by thermal cycle processing in which a cycle of setting the temperature to different values is repeated a plurality of times. To perform the thermal cycle processing in the flow-path (201), for example, the liquid particles (25) are conveyed so as to pass through a plurality of temperature zones provided in the flow-path (201). This extends the conveyed distance and causes some liquid particles (25) to be retained during conveyance. By moving the liquid particles (25) by the interface (23) of the fluid (24), remaining of the liquid particles (25) can efficiently be avoided.

In the case where the particles (22) are solid carriers (26), it is preferable that the target component (20) is nucleic acid, the processing of the target component (20) is breaking the liquid particles (25) including the carriers (26) bonded to amplified nucleic acid, and the carriers (26) taken out of the broken liquid particles (25) are moved by moving the interface (23) of the fluid (24). When breaking the water phase liquid particles (25) formed in the oil phase oil, for example, the carriers (26) taken out of the broken liquid particles (25) contact the surrounding oil and acquire characteristics of aggregating and adhering easily. By moving the carriers (26), taken out of the broken liquid particles (25), by the interface (23) of the fluid (24), remaining of the carriers (26) can effectively be avoided.

In this case, it is preferable that the process liquid (21) includes a reagent for breaking the liquid particles (25) and, in the processing of breaking the liquid particles (25), the liquid particles (25) including the carriers (26) bonded to the amplified nucleic acid are mixed with the reagent for breaking the liquid particles (25) to break the liquid particles (25). The liquid particles (25) can easily be broken by simply mixing the liquid particles (25) with the reagent for breaking the liquid particles (25).

Preferably, in the case where the particles (22) are liquid particles (25) including the target component (20), it is preferable that the processing of the target component (20) is forming the liquid particles (25) in the process liquid (21) in the flow-path (201), the liquid particles (25) including a mixed liquid of cells, a reagent for disintegrating the cells, and the carriers (26) that bond to nucleic acid, and the liquid particles (25) including the cells and the carriers (26) bonded to nucleic acid are moved by moving the interface (23) of the fluid (24). When the liquid particles (25) are formed in the process liquid (21) in the flow-path (201), the liquid particles (25) may adhere to the inner wall (11) and remain in the flow-path (201). By moving the liquid particles (25) formed in the process liquid (21) by the interface (23) of the fluid (24), remaining of the liquid particles (25) can effectively be avoided.

In the case where the particles (22) are solid carriers (26), it is preferable that the target component (20) is nucleic acid, the processing of the target component (20) includes breaking the liquid particles (25) in the process liquid (21) in the flow-path (201), the liquid particles (25) including the carriers (26) bonded to the nucleic acid taken out of disintegrated cells in a mixed liquid of the cells, the reagent for disintegrating cells, and the carriers (26) that bond to nucleic acid, and the carriers (26) bonded to the nucleic acid taken out of the disintegrated cells are moved by moving the interface (23) of the fluid (24). By moving the carriers (26) taken out of the broken liquid particles (25) by the interface (23) of the fluid (24), remaining of the carriers (26) can efficiently be avoided.

In the method of processing a specimen according to the first aspect, the fluid (24) is preferably a liquid that separately stays in a phase different from the process liquid (21) which is in contact, or a gas. By suitably selecting a liquid or a gas as the fluid (24), the interface (23) can easily be formed.

Preferably, when the process liquid (21) is a water phase liquid, the fluid (24) is an oil phase liquid or a gas, and when the process liquid (21) is an oil phase liquid, the fluid (24) is a water phase liquid or a gas. An interface is easily formed between a liquid mainly including water, which is composed of polar molecules, and a liquid mainly including an oil, which is composed of non-polar molecules. No matter the molecules are polar or non-polar, a gas easily and surely forms an interface dividing the gas from the liquid. Using such a fluid (24), the interface is further surely formed to divide the process liquid (21) from the fluid (24).

A second aspect of the present invention is a specimen processing apparatus (500) for processing a target component (20) in a specimen using a specimen processing chip (100), the apparatus (500) including: a chip base (510) on which the specimen processing chip (100) provided with a flow-path (201) is provided; and an introducer (520) for introducing a fluid (24) into the flow-path (201) of the specimen processing chip (100) to form an interface (23) that divides the fluid (24) from a process liquid (21) used for the processing of the target component (20), in which the introducer (520) forms the interface (23) that divides the process liquid (21) containing particles (22) including the target component (20) from the fluid (24) introduced into the flow-path (201) with a rim of the interface (23) on an inner wall (11) of the flow-path (201), and the introducer (520) moves the interface (23) along the flow-path (201) with the rim of the interface (23) on the inner wall (11) to force out the particles (22) retained in the process liquid (21) by the fluid (24).

The specimen processing apparatus (500) according to the second aspect is provided with the introducer (520). The introducer (520) forms the interface (23) that divides the process liquid (21) containing the particles (22) including the target component (20) from the fluid (24) introduced into the flow-path (201) with the rim of the interface (23) on the inner wall (11) of the flow-path (201). The introducer (520) moves the interface (23) along the flow-path (201) with the rim on the inner wall (11) to force out the particles (22) retained in the process liquid (21) by the fluid (24). In a case where the particles (22) including the target component (20) are retained in the flow-path (201) during the processing of the target component (20) in the flow-path (201), the interface (23) can be formed to divide the process liquid (21) from the fluid (24) with the rim of the interface (23) on the inner wall (11) by introducing the fluid (24) into the flow-path (201). The interface (23) is then moved along the flow-path (201) with the rim of the interface (23) on the inner wall (11) to forcibly convey the particles (22) retained in the flow-path (201) together with the process liquid (21). This avoids remaining of the particles (22) including the target component (20) in the flow-path (201) where the target component (20) is processed, the flow-path (201) being provided in the specimen processing chip (100).

In the specimen processing apparatus (500) according to the second aspect, the introducer (520) preferably forces out the particles (22) retained in the process liquid (21) out of the specimen processing chip (100) by introducing the fluid (24). In such a manner, the process liquid (21) in the downstream of the interface (23) can be forced out of the specimen processing chip (100) together with the retained particles (22), which enables collecting a large number of particles (22) while suppressing the increase in the amount of a sample collected from the specimen processing chip (100) compared to, for example, a method in which a great amount of the process liquid (21) is introduced in the flow-path (201) to force out the retained particles (22).

In the specimen processing apparatus (500) according to the second aspect, the number of particles (22) in the process liquid (21) is preferably from 100 thousand to 10 million. For such a large number of particles (22), the collection rate of the particles (22) including the target component (20) can be raised by using the method that avoids remaining of the particles (22) in the flow-path (201), and thereby measurement sensitivity can be improved.

In the specimen processing apparatus (500) according to the second aspect, the process liquid (21) preferably includes a water phase liquid and an oil phase liquid. In this case, when either of the water phase liquid or the oil phase liquid adheres to the inner wall (11) of the flow-path (201), an interface formed between the phases traps the particles (22) between the water phase liquid and the oil phase liquid to easily cause the particles (22) to be retained near the inner wall (11). Moving the particles (22) retained on the inner wall (11) by moving the interface (23) along the flow-path (201) with the rim of the interface (23) on the inner wall (11) is effective when using the process liquid (21) including the water phase liquid and the oil phase liquid.

In the specimen processing apparatus (500) according to the second aspect, the introducer (520) moves the interface (23) along the flow-path (201) to convey the retained particles (22) along the flow-path (201) away from the inner wall (11) of the flow-path (201). In this manner, the particles (22) retained on the inner wall (11) of the flow-path (201) are forcibly moved away from the inner wall (11) by the approaching interface (23). This effectively avoids remaining of the particles (22) retained on the inner wall (11) of the flow-path (201) where the flow velocity is small and thus conveyance of the particles (22) is difficult.

In this case, the introducer (520) preferably moves the interface (23) along the flow-path (201) so that the interface (23) contacts the particles (22) retained on the inner wall (11). In this manner, the moving interface (23) contacts the particles (22) adhering to the inner wall (11) of the flow-path (201) and applies a force that rips off the particles (22) from the inner wall (11). As a result, even for the particles (22) adhering to the inner wall (11) of the flow-path (201), remaining of the particles (22) in the flow-path (201) can further effectively be avoided.

In the specimen processing apparatus (500) according to the second aspect, it is preferable that the introducer (520) includes a pump (521) for pressurizing the flow-path (201), and a plurality of valves (522) for opening and closing a pressure line to the flow-path (201). By opening and closing the valves (522), the interface (23) is formed to divide the process liquid (21) from the fluid (24) introduced into the flow-path (201), and the interface (23) is moved by pressure. The interface (23) of the fluid (24) can easily be formed by opening and closing the valve (522). By regulating the pressure of the pump (521) and the opened period and the number of opening and closing of the valve (522), the amount of the fluid (24) introduced and the number of interfaces (23) formed can be controlled. Interfaces suitable for the flow-path shape and the particles (22) can thus be formed.

Preferably, the introducer (520) opens and closes the valve (522) for introducing the process liquid (21) and the valve (522) for introducing the fluid (24) alternately to interpose the fluid (24) in the flow of the process liquid (21) in the flow-path (201). An interposed region (28) of the fluid (24) having the interfaces (23) on both ends is thus formed in the process liquid (21). By simply interposing the fluid (24) in the flow of the process liquid (21), the two interfaces (23) are formed to divide the process liquid (21) from the fluid (24). By moving the interposed region (28) of the fluid (24) together with the process liquid (21), the particles (22) that the first interface (23) has failed to convey along the moving direction can be conveyed by the second interface (23). The conveyance efficiency of the interface (23) can thus be improved. By a simple control of alternately regulating opening and closing of the valves (522), the interposed region (28) of the fluid (24) is easily formed in the flow-path (201).

Preferably, for the introducer (520) provided with the pump (521) and the valves (522), the fluid (24) is air, and the introducer (520) includes an air line (527) to supply air from the pump (521) to the valve (522) and from the valve (522) to the specimen processing chip (100). Using air as the fluid (24), the interface (23) can easily be formed for various types of the process liquid (21). Unlike using a liquid as the fluid (24), the liquid amount in the flow-path (201) does not increase, and thus the increase in the liquid amount of the finally collected sample containing the particles (22) including the target component (20) is suppressed. Therefore, no additional processing to condense the target component (20) is necessary after collecting the sample. Unlike using a specific gas other than air as the fluid (24), the air as the fluid (24) can be obtained easily and introduced into the flow-path (201) via the air line (527).

Preferably, in the specimen processing apparatus (500) according to the second aspect, the target component (20) is nucleic acid, the particles (22) are magnetic particles (26a) bonded to nucleic acid, the specimen processing apparatus (500) further includes a magnetic unit (542) for magnetically catching the magnetic particles (26a) in the flow-path (201), the target component (20) is processed with the magnetic particles (26a), bonded to nucleic acid, magnetically caught in the flow-path (201) by the magnetic unit (542), and the magnetic particles (26a) are released after the processing of the target component (20) and moved by the interface (23) of the fluid (24). In this manner, the magnetic particles (26a) once magnetically caught adhering to the inner wall (11) of the flow-path (201) can be moved away from the inner wall (11) by the interface (23) of the fluid (24). As a result, remaining of the magnetic particles (26a), once caught on the inner wall (11), in the flow-path (201) can effectively be avoided.

Preferably, in the specimen processing apparatus (500) according to the second aspect, the particles (22) are liquid particles (25) including the target component (20), and the introducer (520) introduces the fluid (24) into the flow-path (201) containing the process liquid (21) including the liquid particles (25) to form the interface (23) different from liquid particle interfaces (25a) forming the liquid particle (25). The introducer (520) moves the interface (23) along the flow-path (201) to convey the liquid particles (25) in the process liquid (21) along the flow-path (201). In a case where the liquid particles (25) are retained in the process liquid (21) in the flow-path (201), the interface (23) different from the liquid particle interfaces (25a) can be formed with the rim of the interface (23) on the inner wall (11) by introducing the fluid (24) into the flow-path (201). The interface (23) is then moved along the inner wall (11) to forcibly convey the liquid particles (25) retained in the process liquid (21) in the flow-path (201) together with the process liquid (21). As a result, remaining of the liquid particles (25) including the target component (20) in the flow-path (201) can further effectively be avoided.

Remaining of particles including a target component in a flow-path where the target component is processed can be avoided, the flow-path being provided in the specimen processing chip.

BRIEF DESCRIPTION OF THE DRAWINGS

FIG. 29A is a top view illustrating an example disposition of a detecting unit;

FIG. 29B is a cross sectional view schematically illustrating an example disposition of the detecting unit in the chip base;

FIG. 30A is a bottom view illustrating an example disposition of a magnetic unit;

FIG. 30B is a cross sectional view schematically illustrating an example disposition of the detecting unit in the chip base;

DETAILED DESCRIPTION OF THE PREFERRED EMBODIMENTS

Embodiments will now be described with reference to the drawings.

[Summary of Method of Processing Specimen]

Figure 1:
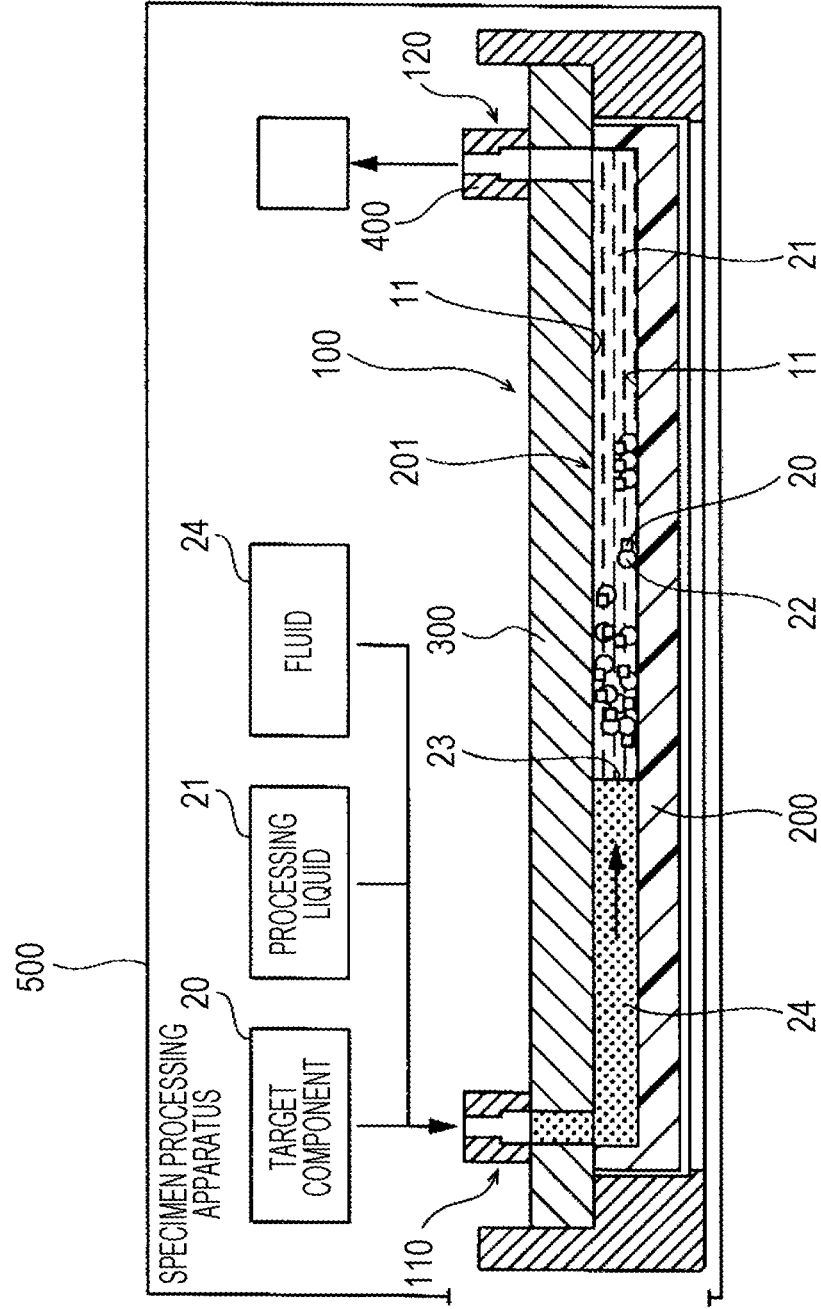
FIG. 1 schematically illustrates a specimen processing chip.

A method of processing a specimen according to an embodiment will now be described schematically with reference to FIG. 1.

The method of processing a specimen according to the embodiment uses a specimen processing chip 100 provided with a flow-path 201 to perform processing of a target component 20 in a specimen.

The specimen processing chip 100 is disposed in a specimen processing apparatus 500. The specimen processing chip 100 is used to perform processing including one or more processing steps for the target component 20 in a specimen supplied by the specimen processing apparatus 500. The specimen processing chip 100 receives a specimen including the target component 20. The specimen processing chip 100 is configured as a cartridge which is set in the specimen processing apparatus 500 so that the processing of the specimen can be performed in the specimen processing apparatus 500. The specimen processing chip 100 is a micro fluid chip provided with a very small flow-path where a desired processing step is performed as will be described below. The flow-path is, for example, a micro-flow-path having dimensions (width, height, and inner diameter) of 0.1 μm to 1000 μm.

Liquid collected from a patient, such as body liquid and blood (whole blood, serum, or plasma), or a specimen obtained by a certain pre-processing of collected body liquid or blood is introduced into the specimen processing chip 100. The target component 20 is, for example, nucleic acid such as DNA (deoxyribo nucleic acid), cells or intracellular substances, antigen or antibody, protein, or peptide. When the target component 20 is nucleic acid, for example, extraction liquid containing nucleic acid extracted from blood, for example, by a certain pre-processing is introduced into the specimen processing chip 100.

The specimen including the target component 20 introduced into the specimen processing chip 100 is supplied through the specimen processing chip 100 by the specimen processing apparatus 500. One or more steps of processing are performed on the target component 20 in a predetermined order while the specimen is being supplied. By the processing of the target component 20, an assay sample suitable for analyzing the specimen or a liquid sample suitable for the subsequent processing using another apparatus is produced in the specimen processing chip 100.

The specimen processing chip 100 includes, for example, a fluid module 200 provided with the flow-path 201 and a base plate 300. Besides the liquid including the target component 20, a liquid used for processing the target component 20 or other type of fluids, such as a gas, may be introduced into the flow-path 201 of the specimen processing chip 100. The flow-path 201 has a form of a tube having an inner wall 11.

The processing of the target component 20 depends on the use of the specimen processing chip 100. The processing of the target component 20 includes, for example, mixing the specimen with a reagent, causing reaction between the specimen and the reagent, dispersing the specimen including the target component 20 in a form of very small liquid particles, breaking the dispersed liquid particles, and cleaning off unnecessary components included in the specimen. The processing of the target component 20 may be one among the examples described above or a combination of a plurality of those of the examples. The processing of the target component 20 may be any processing that produces a desired sample.

By the processing performed in the flow-path 201, the liquid or solid including the target component 20 becomes particles 22 that are then sent to a flow-path where the subsequent processing is performed or to the outside of the specimen processing chip 100. The particles 22 may be in the process liquid 21 used for processing. Namely, the particles 22 may be in the process liquid 21, keeping the form of particles without uniting with the process liquid 21. For example, as a result of the processing of the target component 20, the particles 22 including the target component 20 are dispersed in the process liquid 21. The term "dispersed" means that the substance taking a form of particles is suspended in the liquid.

As a result of the processing of the target component 20 in the flow-path 201, the particles 22 including the target component 20 are in the process liquid 21 used for the processing of the target component 20.

In a system that contains the particles 22 in the process liquid 21, some particles 22 are retained in the flow-path 201, though not intended, during the processing of the target component 20. The particles 22 are retained by, for example, adhering to the inner wall 11 of the flow-path 201. The particles 22 may be retained also by, for example, settling to the inner wall 11 on the bottom of the flow-path 201 to aggregate or going up to the inner wall 11 on the top of the flow-path 201 to aggregate.

Figure 2:
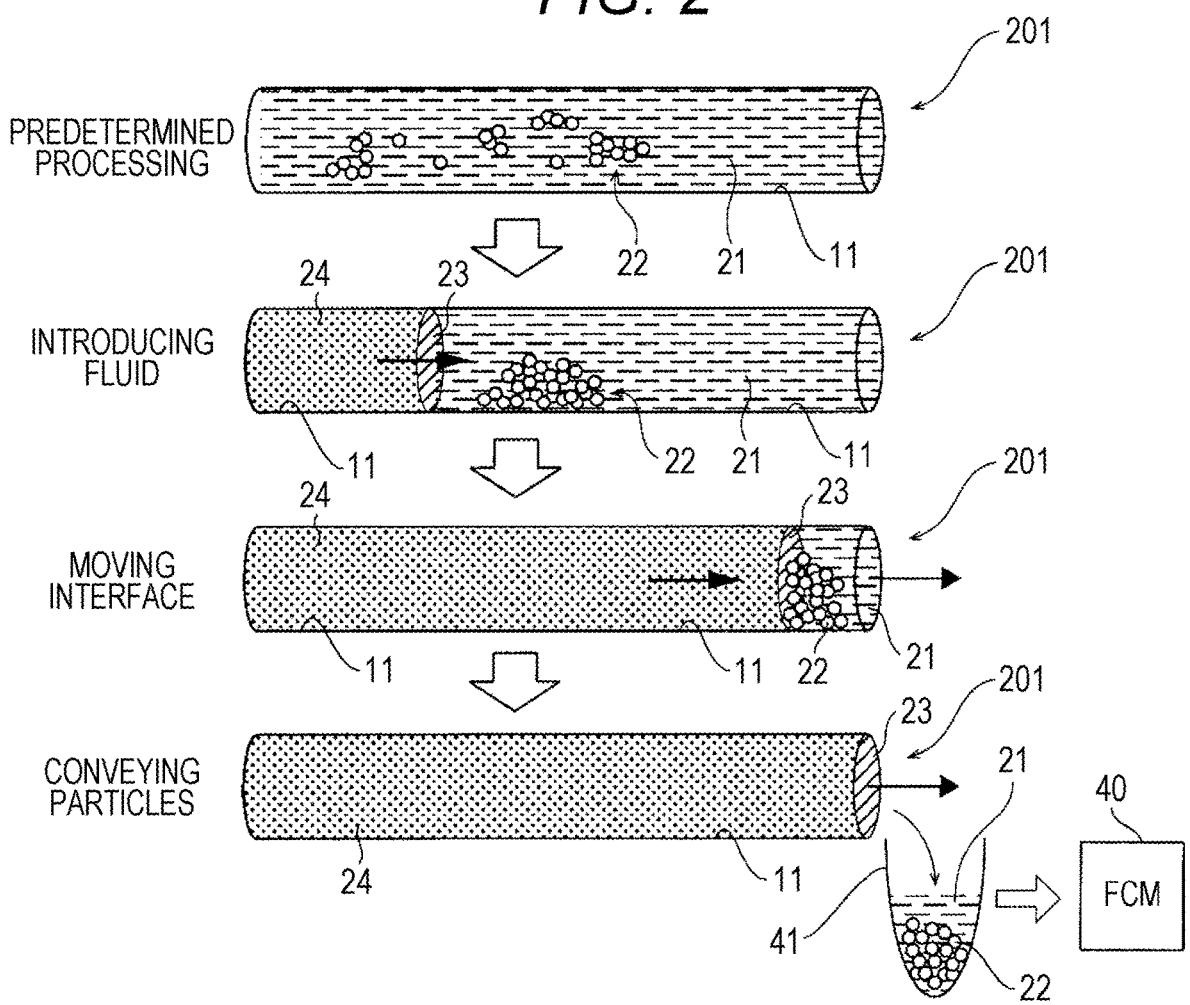
FIG. 2 illustrates a method of processing a specimen.

As illustrated in FIG. 2, in the method of processing a specimen according to the embodiment, the fluid 24 is introduced into the flow-path 201 to form an interface 23 that divides the process liquid 21 used for the processing of the target component 20 from the fluid 24, the process liquid 21 containing particles 22 including the target component 20, the rim of the interface 23 being on an inner wall 11 of the flow-path 201, and the interface 23 is moved along the flow-path 201 with the rim of the interface 23 on the inner wall 11 to force out the particles 22 retained in the process liquid 21 by the fluid 24.

The fluid 24 conveys the particles 22 together with the process liquid 21 along the flow-path 201. The fluid 24 may be a liquid or a gas. Any fluid 24 that forms the interface 23 that divides the fluid 24 from the process liquid 21 may be used. For example, such a liquid that does not mix with the process liquid 21 or such a gas of an amount greater than the amount dissolved in the process liquid 21 is introduced as the fluid 24 to form the interface 23 that divides the process liquid 21 from the fluid 24 in the flow-path 201. The term "interface" means a sectional area by which the uniform liquid phase or gas phase fluid 24 is in contact with another uniform liquid phase process liquid 21. The term "phase" means the state of a matter, namely, gas, liquid, or solid. The chemical composition and the physical state are assumed to be uniform or approximately uniform in each phase.

By moving the interface 23 along the flow-path 201 with the rim of the interface 23 on the inner wall 11, the particles 22 retained in the flow-path 201 can forcibly be conveyed together with the process liquid 21. For example, the particles 22 that adhere or settle in the flow-path 201 are moved by the approaching interface 23. The particles 22 that are no longer adhering to or settling in the flow-path 201 can easily be conveyed with the flow of the fluid 24 and the process liquid 21 along the flow-path 201.

According to the method of processing a specimen according to the embodiment, remaining of the particles 22 including the target component 20 in the flow-path 201, where the target component 20 is processed, of the specimen processing chip 100 can be avoided.

The fluid 24 is introduced so as to form the interface 23 that divides the process liquid 21 from the fluid 24 with the rim of the interface 23 on the inner wall 11 of the flow-path 201. The interface 23 is not necessarily required to have a shape same as the cross section of the flow-path 201 that entirely covers the flow-path cross section. The interface 23 may be formed to contact a portion of the inner wall 11 without contacting the other portion of the inner wall 11 in a flow-path cross section. For example, the interface 23 is formed to contact at least the portion of the inner wall 11 where the particles 22 adhere. For example, the interface 23 is formed to cover the full width of the flow-path 201.

The fluid 24 introduced into the flow-path 201 preferably forms the interface 23 that entirely covers the flow-path cross section. Such an interface 23 entirely covering the flow-path 201 conveys every particles 22 no matter which portion of the flow-path cross section the particles 22 are retained. By moving the interface 23 along the flow-path 201, the particles 22 in the flow-path 201 can surely be conveyed.

The fluid 24 is a liquid that separately stays in a phase different from the process liquid 21 which is in contact, or a gas. By suitably selecting a liquid or a gas as the fluid 24, the interface 23 can easily be formed.

For example, when the water phase process liquid 21 is used, the fluid 24 is preferably an oil phase liquid or a gas. For example, when the oil phase process liquid 21 is used, the fluid 24 is preferably a water phase liquid or a gas. An interface is easily formed between a liquid mainly including water, which is composed of polar molecules, and a liquid mainly including an oil, which is composed of non-polar molecules. No matter the molecules are polar or non-polar, a gas easily and surely forms an interface dividing the gas from the liquid. Using such a fluid 24, the interface 23 is further surely formed to divide the process liquid 21 from the fluid 24.

The fluid 24 is preferably a gas. Using a gas as the fluid 24, the interface 23 can easily be formed for various types of the process liquid 21. Unlike using a liquid as the fluid 24, the liquid amount in the flow-path 201 does not increase, and thus the liquid amount of the finally collected sample containing the particles 22 including the target component 20 does not increase. Therefore, no additional processing to condense the target component 20 is necessary after collecting the sample.

A gas used as the fluid 24 is preferably air. Unlike using a specific gas other than air as the fluid 24, the air as the fluid 24 can be obtained easily and introduced into the flow-path 201.

In the example in FIG. 2, the particles 22 retained in the process liquid 21 are forced out of the specimen processing chip 100 by the introduced fluid 24. The particles 22 including the target component 20 are collected together with the process liquid 21 from the outlet of the flow-path 201 into a sample container 41. Along with the moving interface 23, the process liquid 21 in the downstream of the interface 23 are forced out of the specimen processing chip 100 with the retained particles 22. Compared to forcing out the retained particles 22 by supplying a large amount of the process liquid 21 at a high velocity into the flow-path 201, for example, a large number of the particles 22 can be collected while suppressing the increase in the amount of the sample collected from the specimen processing chip 100.

The sample containing the particles 22, including the target component 20, collected outside the specimen processing chip 100 is provided to, for example, an external measuring device to be measured. In the example in FIG. 2, the particles 22 forced out of the specimen processing chip 100 are counted by a flow cytometer (FCM) 40. As described above, collecting the particles 22 by moving the interface 23 suppresses the increase in the amount of the sample finally collected from the specimen processing chip 100 and thereby the concentration of the particles 22 in the collected sample can be raised. Therefore, no additional processing is necessary to condense the sample to a concentration suitable for counting performed by the flow cytometer 40. Obtaining a sample of a sufficiently high particle-concentration eliminates the need of condensing the sample which requires settling the particles 22 in the sample by centrifugation to remove supernatant. In a case of an excessively high concentration, a diluting liquid is simply added, which is easier than condensing, to adjust the concentration to a suitable level.

In the flow-path 201, viscosity of the fluid causes a low flow velocity near the inner wall 11. The particles 22 retained in the flow-path 201 therefore easily adhere to or settle on the inner wall 11 of the flow-path 201. The particles 22 retained near the inner wall 11 cannot be conveyed easily even by increasing the flow rate of the flow in the flow-path 201. Therefore, it is preferable to move the interface 23 along the flow-path 201 to move the retained particles 22 away from the inner wall 11 of the flow-path 201, thereby conveying the particles 22 along the flow-path 201. In this manner, the particles 22 retained on the inner wall 11 of the flow-path 201 are forcibly moved away from the inner wall 11 by the approaching interface 23. This effectively avoids remaining of the particles 22 retained on the inner wall 11 of the flow-path 201 where conveyance of the particles 22 is very difficult.

Figure 3:
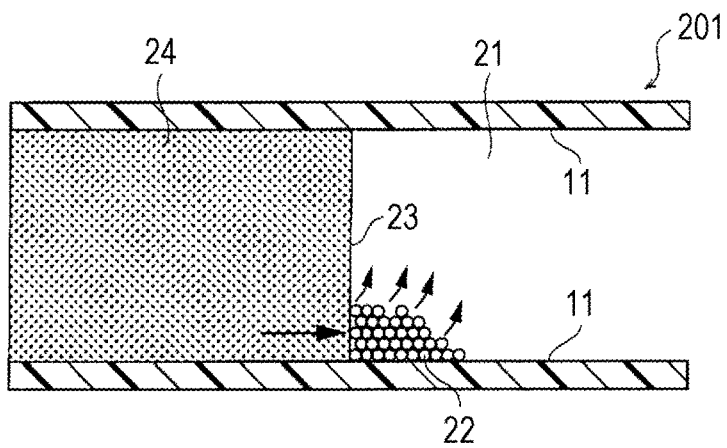
FIG. 3 exemplarily illustrates an interface contacting particles.

In the example in FIG. 3, the interface 23 is moved along the flow-path 201 so that the interface 23 contacts the particles 22 retained on the inner wall 11 and thereby move the particles 22 away from the inner wall 11. The interface 23 is moved to pass the region where the particles 22 are present in the flow-path 201. In this manner, the moving interface 23 contacts the particles 22 adhering to the inner wall 11 of the flow-path 201 to apply a force that rips off the particles 22 from the inner wall 11. As a result, even for the particles 22 adhering to the inner wall of the flow-path 201, remaining of the particles 22 in the flow-path 201 can further effectively be avoided.

Figure 4:
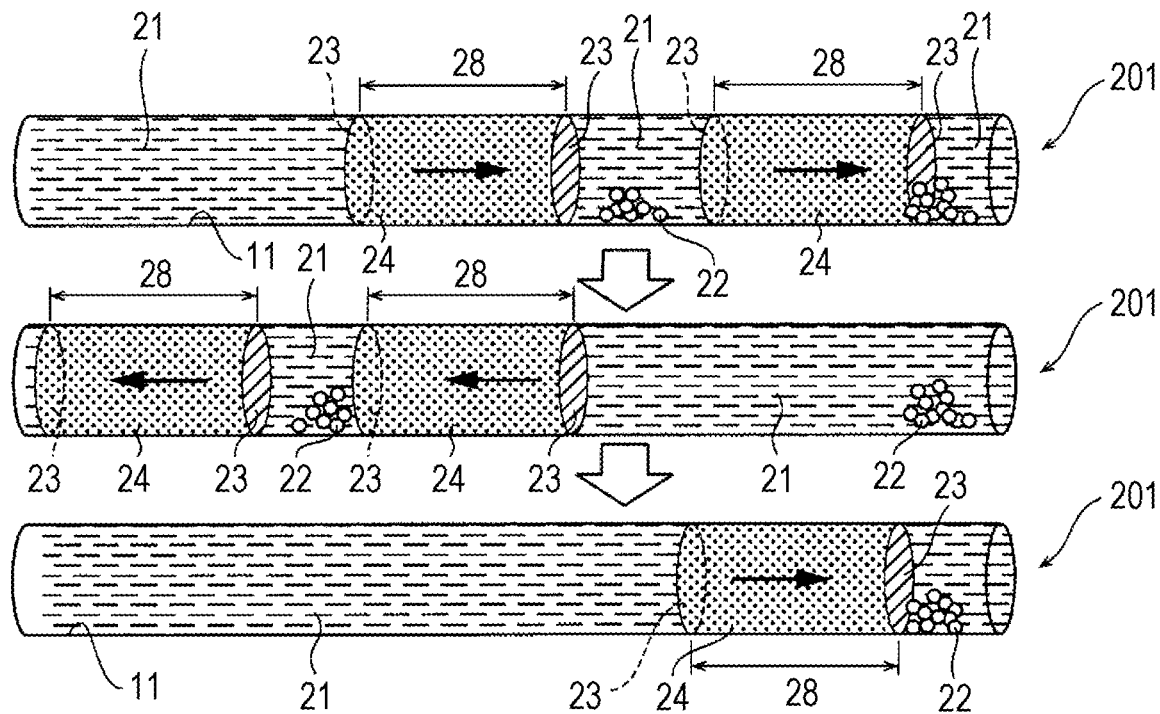
FIG. 4 illustrates an example of the interface moved back and forth and an example of forming an interposed region of fluid.

In the example in FIG. 4, the interface 23 of the fluid 24 is moved back and forth along the flow-path 201 in the region where the particles 22 are retained in the flow-path 201. In this manner, for the particles 22 adhering to the inner wall 11 of the flow-path 201, the interface 23 moving back and forth contacts the particles 22 and repetitively applies a force to the particles 22. The interface 23 moving back and forth releases the particles 22 from an adhering state. Once the particles 22 are set free in the flow-path 201, the particles 22 can easily be conveyed by simply supplying liquid into the flow-path 201. As a result, remaining of the particles 22 in the flow-path 201 can further effectively be avoided. The particles 22 are retained in a region where the particles 22 may settle or adhere in the flow-path 201. Such a region may be a portion of or the entire portion of the flow-path 201. In the processing of catching the particles 22 in the flow-path 201, for example, the particles 22 may be retained in a local region including the portion where the particles 22 are caught. When the particles 22 simply pass through the flow-path 201, the particles 22 may be retained along the entire region of the flow-path 201. In such a case, the region where the particles 22 are retained may be the entire region of the flow-path 201.

In the example in FIG. 4, the fluid 24 is interposed in the process liquid 21 in the flow-path 201 to form the interposed region 28 of the fluid 24 in the process liquid 21. The interposed region 28 has the interface 23 formed on both ends. In this case, the fluid 24 is introduced so as to divide the process liquid 21 midway in the flow-path 201 to form the interposed region 28 occupying a section having a certain length in the flow-path 201. By simply interposing the fluid 24 midway in the flow of the process liquid 21, two interfaces 23 are formed to divide the process liquid 21 from the fluid 24. One interface 23 is formed to divide the process liquid 21 in the downstream in the conveyance direction from the fluid 24, and the other interface 23 is formed to divide the process liquid 21 in the upstream in the conveyance direction from the fluid 24.

By moving the formed interposed region 28 so as the two interfaces 23 to pass the region where the particles 22 are present in the flow-path 201, the retained particles 22 contact the interface 23 two times. By moving the interposed regions 28 of the fluid 24 together with the process liquid 21, the retained particles 22 that the first interface 23 has failed to convey along the moving direction can be conveyed by the second interface 23. The conveyance efficiency of the interface 23 can thus be improved.

The number of the interposed region 28 of the fluid 24 formed in the flow-path 201 is not limited to one. Preferably, the fluid 24 is intermittently interposed a plurality of times in the flow-path 201 to form a plurality of interposed regions 28 of the fluid 24. In this manner, the interfaces 23 are formed by twice the number of the interposed regions 28 formed by the fluid 24. With the same amount of the fluid 24 introduced, the conveyance efficiency of the interface 23 is further improved than forming a large single interposed region 28.

Figure 5:
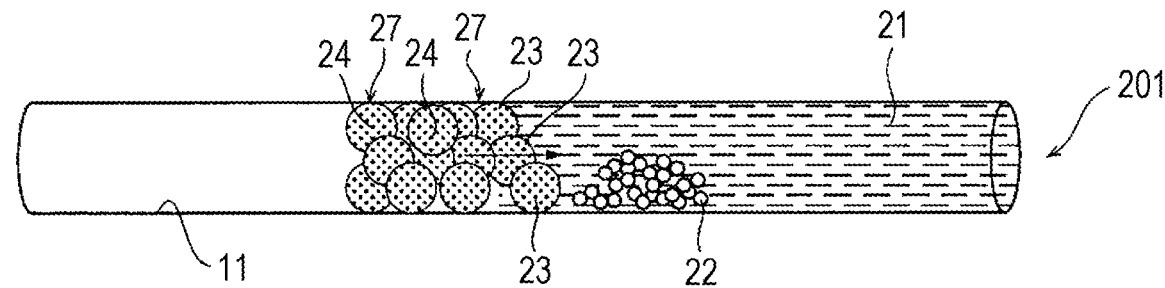
FIG. 5 exemplarily illustrates particles moved by bubbles.

Alternatively, as illustrated in FIG. 5, a plurality of bubbles 27 each having an interface 23 and containing air may be formed in the flow-path 201 and moved along the flow-path 201. The interfaces 23 of the gathered bubbles 27 adjoin each other to form a wall. The interfaces 23 of the gathered bubbles 27 covering the flow-path cross section provides an effect similar to a single interface 23 covering the entire flow-path cross section. By moving the bubbles 27 along the flow-path 201 to move the particles 22 in the flow-path 201, remaining of the particles 22 in the flow-path 201 can be avoided.

Figure 6:
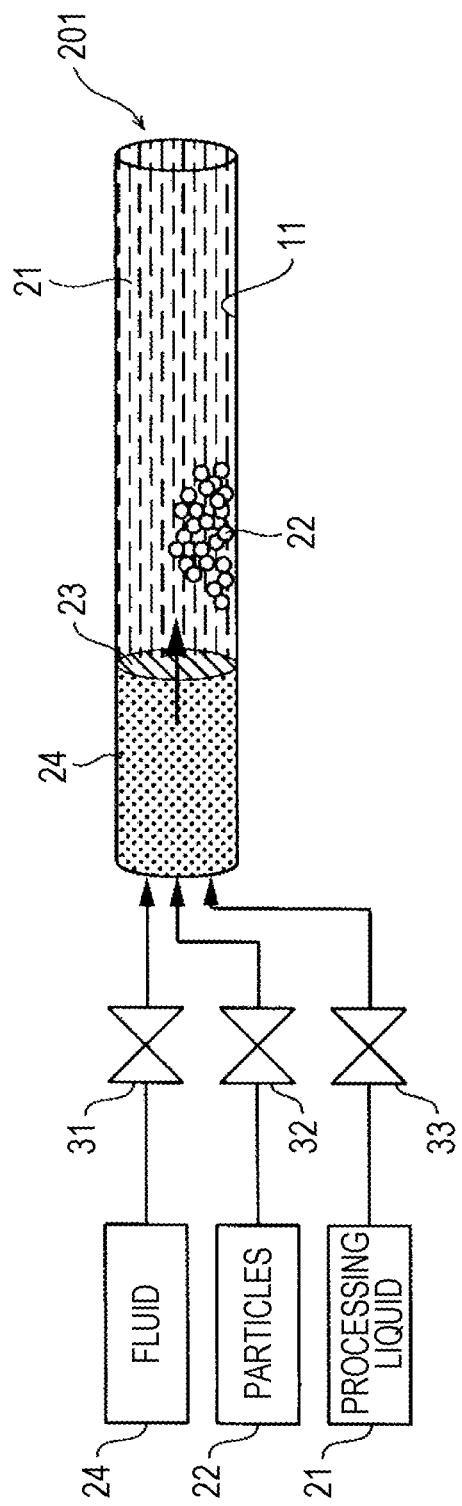
FIG. 6 exemplarily illustrates switching fluids to be introduced into the flow-path by opening and closing valves.

The fluid 24 is introduced into the flow-path 201 to form the interface 23 by, for example, supplying the pressurized fluid 24. As illustrated in FIG. 6, the fluid 24 is introduced by opening and closing a valve 31 connected to the flow-path 201. During or after the processing of the target component 20, the valve 31 for introducing the fluid 24 into the flow-path 201 is opened and closed to form the interface 23 by introducing the fluid 24 into the flow-path 201. In this manner, the interface 23 of the fluid 24 can easily be formed by opening and closing the valve 31.

For example, by opening and closing the valve 31 once after introducing the process liquid 21 including the particles 22 and then introducing the process liquid 21 again, the interposed region 28 of the fluid 24 is formed. By alternately performing opening and closing of the valve 31 and introducing of the process liquid 21, a plurality of interposed regions 28 are formed. The opened period of the valve 31 may be adjusted to control the volume of the introduced fluid 24. By regulating the opened period and the number of opening and closing of the valve 31, the amount of the fluid 24 introduced and the number of interfaces 23 formed can be controlled. The interfaces 23 suitable for the flow-path shape and the particles 22 can thus be formed.

Preferably, the valve 31 for introducing the fluid 24 is provided separately from the valve for introducing the target component 20 and the process liquid 21. Specifically, a valve 32 for introducing the particles 22 including the target component 20 into the flow-path 201 and a valve 33 for introducing the process liquid 21 into the flow-path 201 are each opened and closed to introduce the particles 22 and the process liquid 21 into the flow-path 201. Then, the valve 31 for introducing the fluid 24 into the flow-path 201 is opened and closed to introduce the fluid 24 into the flow-path 201.

Introduction of the fluid 24 into the flow-path 201 can be controlled independent of introducing the particles 22 and the process liquid 21. The interposed region 28 can arbitrarily be formed to an adjusted size while controlling the flow rate and the flow velocity of the particles 24 and the process liquid 21 by the valve 32 and the valve 33. The interface 23 suitable for the flow rate and the flow velocity of the particles 22 and the process liquid 21 can thus be formed.

<Particles and Process Liquid>

The particles 22 and the process liquid 21 may be used in various combinations according to the processing of the target component 20. Various types of the particles 22 can be conveyed by the interface 23.

Figure 7:
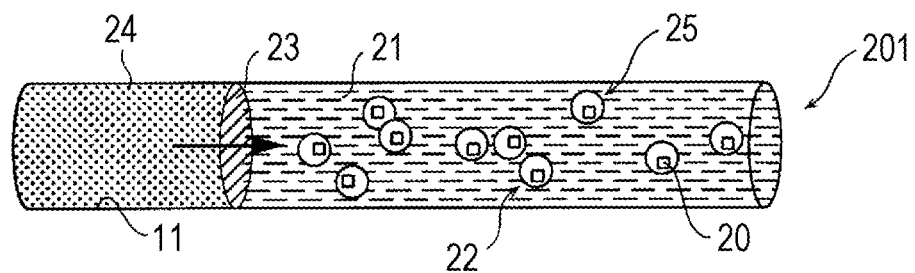
FIG. 7 illustrates an example where the particles are liquid particles.

In FIG. 7, for example, the particles 22 including the target component 20 are liquid particles 25 including the target component 20. When the liquid particles 25 including the target component 20 are contained in the process liquid 21, the liquid particles 25 retained in the flow-path 201 are forcibly conveyed by the interface 23. Consequently, remaining of the liquid particles 25, which are particles 22 other than solid particles such as magnetic particles 26a, in the flow-path 201 can effectively be avoided. An excessive force might act on the liquid particles 25 in order to avoid remaining of the liquid particles 25. However, such an excessive force can be avoided by conveying the retained liquid particles 25 by the moving interface 23.

Figure 8:
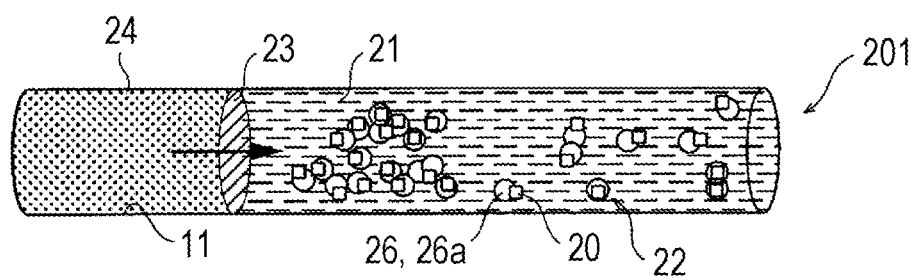
FIG. 8 illustrates an example where the particles are carriers.

In FIG. 8, for example, the particles 22 including the target component 20 are solid carriers 26 surficially bonded to the target component 20. Such carriers 26 easily aggregate by bonding to the target component 20 in the specimen and therefore easily adhere to the inner wall 11 of the flow-path 201. Remaining of the carriers 26 in the flow-path 201 can effectively be avoided.

Figure 9:
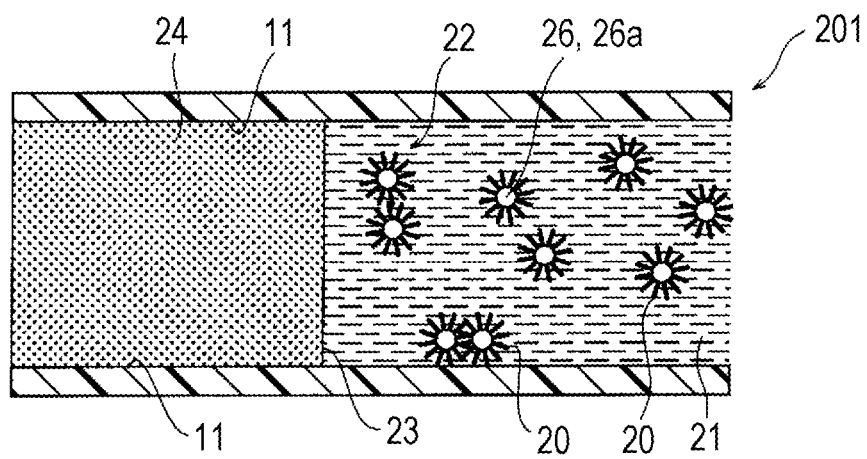
FIG. 9 exemplarily illustrates carriers bonded to amplified nucleic acid as the particles.

In the example in FIG. 9, the target component 20 is nucleic acid, and the particles 22 are the carriers 26 bonded to amplified nucleic acid covering the surface the carriers 26 as a result of nucleic acid amplification. With the nucleic acid covering the surface of the carrier 26, or the particles 22, the carriers 26 easily aggregate and adhere to the inner wall 11 of the flow-path 201, which causes the particles 22 to be retained in the flow-path 201. The carriers 26, bonded to the amplified nucleic acid, retained in the flow-path 201 can also be conveyed efficiently by moving the interface 23 along the flow-path 201, thereby avoiding remaining of the carriers 26.

The method of processing a specimen according to the embodiment is effective for the particles 22 and the process liquid 21 that have different specific gravities. The method of processing a specimen according to the embodiment is effective for the particles 22 having an outer diameter from 0.1 μm to 0.1 mm.

When the particles 22 and the process liquid 21 have different specific gravities, the particles 22 in the process liquid 21 easily go down to the bottom side or go up to the top side in the flow-path 201. The particles 22 having a larger specific gravity than the process liquid 21 easily remain near the inner wall 11 on the bottom of the flow-path 201. When the specimen processing chip 100 is in a position to be used, the bottom of the flow-path 201 is in the lower side with respect to the direction in which the gravity acts. The particles 22 having a smaller specific gravity than the process liquid 21 easily remain near the inner wall 11 on the top of the flow-path 201. When the specimen processing chip 100 is in a position to be used, the top of the flow-path 201 is in the upper side with respect to the direction in which the gravity acts.

Very small particles 22 having an outer diameter from 0.1 μm to 0.1 mm have a larger relative surface area than particles having a larger diameter. Such very small particles 22 easily aggregate and thereby tend to remain by a large amount. Such very small particles 22 retained on the inner wall 11 can be conveyed by the interface 23 formed by the fluid 24. Remaining of the particles 22 in the flow-path 201 is thus effectively avoided.

The number of particles 22 in the process liquid 21 in the specimen processing chip 100 is from 100 thousand to 10 million. In such a case, a very large number of particles 22 move in the flow-path 201. For such a very large number of particles 22, the embodiment is also effective to avoiding the particles 22 from remaining in the flow-path 201. For a very large number of particles 22, the collection rate of particles 22 including the target component 20 can be raised to improve measurement sensitivity.

The method of processing a specimen according to the embodiment is effective for the process liquid 21 including a water phase liquid and an oil phase liquid. For example, such a case is when the process liquid 21 includes water phase reagents and an oil phase oil. In this case, when either of the water phase liquid or the oil phase liquid adheres to the inner wall 11 of the flow-path 201, an interface formed between the phases traps the particles 22 between the water phase liquid and the oil phase liquid to easily cause the particles 22 to be retained near the inner wall 11. The particles 22 retained on the inner wall 11 can be moved by moving the interface 23 along the flow-path 201 with the rim of the interface 23 on the inner wall 11. This effectively avoids remaining of the particles 22 which is likely to happen.

In some conditions, depending on the particles 22 and the process liquid 21 or the processing using the process liquid 21, the particles 22 may easily be retained in the flow-path 201. The method of processing a specimen according to the embodiment, which avoids remaining of the particles 22, is particularly effective in such a condition in which the particles 22 are easily retained in the flow-path 201.

Figure 10:
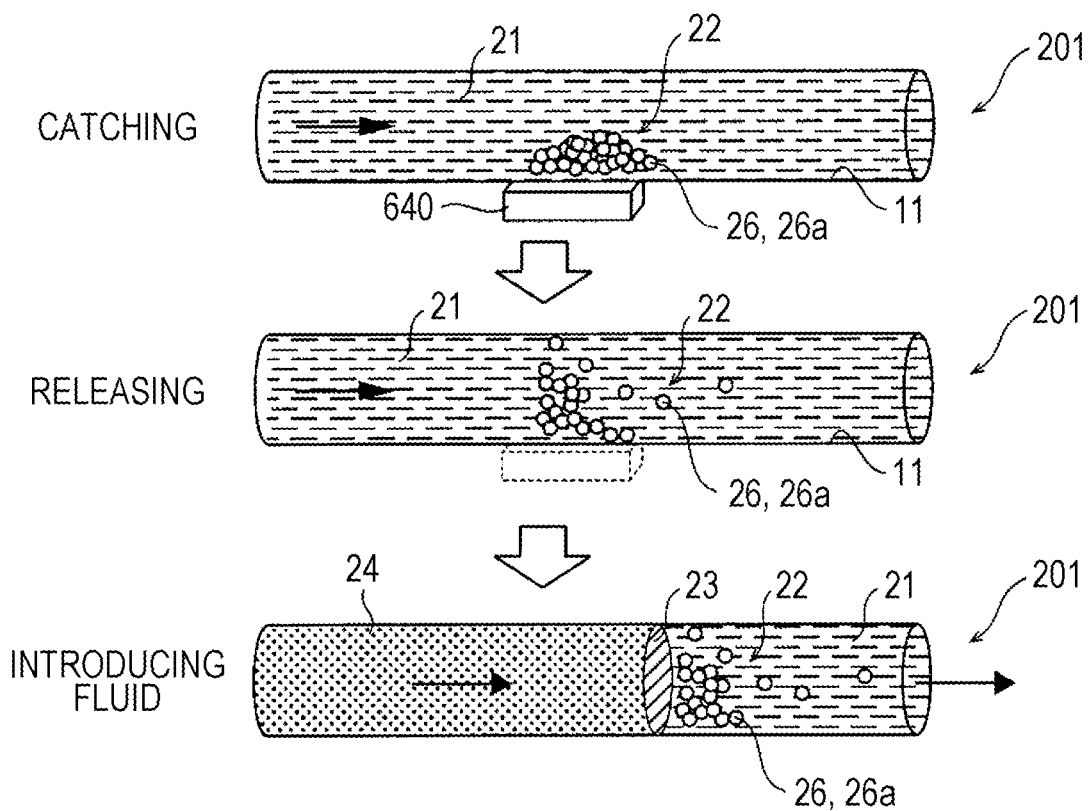
FIG. 10 illustrates a step of catching the particles and a step of releasing the particles.

In the example in FIG. 10, the processing of the target component 20 includes catching the carriers 26 in the flow-path 201. The way of catching the carriers 26 is not particularly limited. For example, the carriers 26 including a magnetic substance can be caught by a magnetic force. The charged carriers 26 can be caught by electrocataphoresis performed in an electric field.

The caught carriers 26 are retained at a certain place in the flow-path 201 for a certain period of time. The carriers 26 caught in the flow-path 201 easily aggregate and settle or adhere to the inner wall 11. The carriers 26 once caught are easily retained after being released. In the example in FIG. 10, the carriers 26 are caught to be processed and then the carriers 26 are released and moved by the interface 23 of the fluid 24. The carriers 26 once caught and then released, which are easily retained in the flow-path 201, can also be moved by moving the interface 23 of the fluid 24. Remaining of the carriers 26 in the flow-path 201 can thus be avoided effectively.

In FIG. 10, the carriers 26 are, for example, the magnetic particles 26a. When using the magnetic particles 26a, the carriers 26, namely the magnetic particles 26a, are magnetically caught in the flow-path 201. The magnetic particles 26a are magnetically caught by a magnetic force of a magnet 640 disposed outside the flow-path 201 acting on the magnetic particles 26a. The magnetic particles 26a are magnetically gathered near the inner wall 11 of the flow-path 201 and therefore easily aggregate and adhere. Preferably, such magnetic particles 26a once magnetically caught and then released are moved by the interface 23 of the fluid 24. When the magnetic particles 26a once magnetically caught adhere to the inner wall 11 of the flow-path 201, the moving interface 23 of the fluid 24 can move the magnetic particles 26a away from the inner wall 11. As a result, remaining of the magnetic particles 26a once caught on the inner wall 11 in the flow-path 201 can effectively be avoided.

<Flow-Path>

The flow-path 201 of the specimen processing chip 100 may have any form that allows a liquid introduced from an inlet port of the specimen processing chip 100 to flow therethrough. The flow-path 201 has a shape suitable for the processing performed in the flow-path 201. The flow-path 201 has a width, a height or depth, a length, and a volume which are suitable for the processing performed in the flow-path 201. The flow-path 201 takes a form of a thin tubular passage or a channel. The channel may be straight, curved, or have a zig-zag form. A dimension such as the width or the height of flow-path 201 may change along the path (see FIG. 11). A portion of or the entire flow-path 201 may have a flat and wide shape (see FIG. 34). The flow-path 201 may have a form of a chamber that can store the introduced liquid (not shown).

Figure 11:
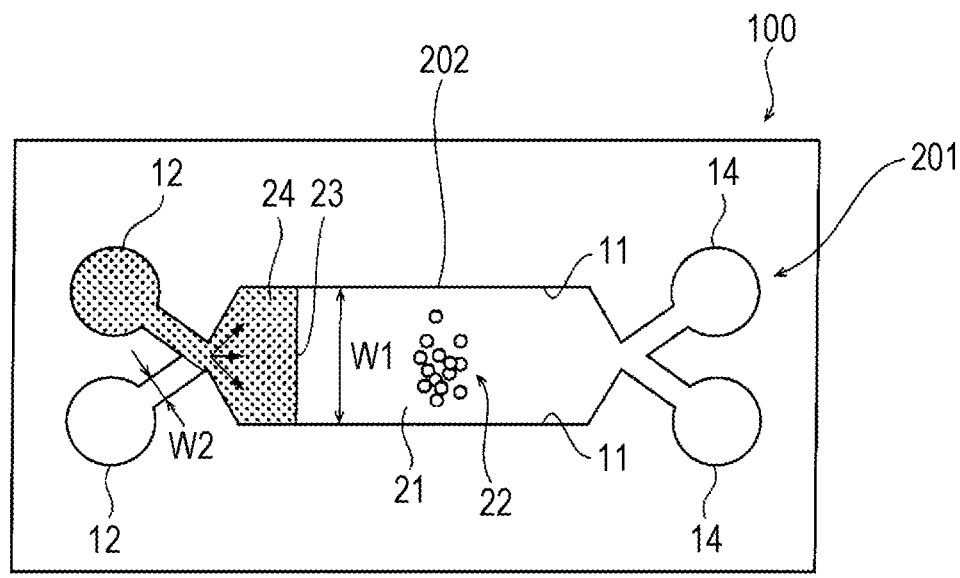
FIG. 11 is a schematic plan view of an example flow-path.

As illustrated in FIG. 11, the flow-path 201 has, for example, a joint 12 provided on an end, a channel 202 in which the target component 20 is processed, and a joint 14 provided on the other end. The joint 12, the channel 202, and the joint 14 may each be provided by an arbitrary number.

For example, the joint 12 is an inlet port from which the liquid flows in. The particles 22 and the process liquid 21 flow in from the joint 12 to the channel 202. The target component 20 included in the particles 22 is processed in the channel 202. The particles 22 and the process liquid 21 that have been processed flow from the channel 202 to the joint 14. The particles 22 and the process liquid 21 are sent via the joint 14 to another flow-path 201 for the next processing and to the outside of the specimen processing chip 100.

Likewise, the fluid 24 flows via the joint 12 to the channel 202 and forms the interface 23 in the channel 202. By moving the interface 23 of the fluid 24 toward the joint 14, the particles 22 retained in the channel 202 are conveyed toward the joint 14.

The particles 22 and the process liquid 21 flow from one end of the flow-path 201 where the joint 12 is provided to the other end of the flow-path 201 where the joint 14 is provided. In such a manner, the particles 22 and the process liquid 21 simply flow from one end to the other end of the flow-path 201 and no back and forth motion of the particles 22 and the process liquid 21 is required. The fluid 24 is introduced from one end of the flow-path 201 and moved to the other end, which makes conveyance of the particles 22 easy.

The channel 202 has, for example, a flow-path width W1 larger than a flow-path width W2 of the joint 12 or the joint 14. The channel 202 has a wide shape, namely, a relatively large flow-path width in the flow-path 201. Thus, the particles 22 are distributed across the wide channel 202 to contact the process liquid 21 so that the target component 20 can efficiently be processed.

In this case, the fluid 24 introduced into the channel 202 adjusts its form to the flow-path width of the channel 202. With a sufficient amount of the fluid 24 introduced into the channel 202, the interface 23 is formed to cover the entire flow-path cross section of the channel 202. The particles 22 retained in the channel 202 can efficiently be conveyed by the interface 23 because the fluid 24 adjusts its form along the cross section of the flow-path 201.

Figure 12:
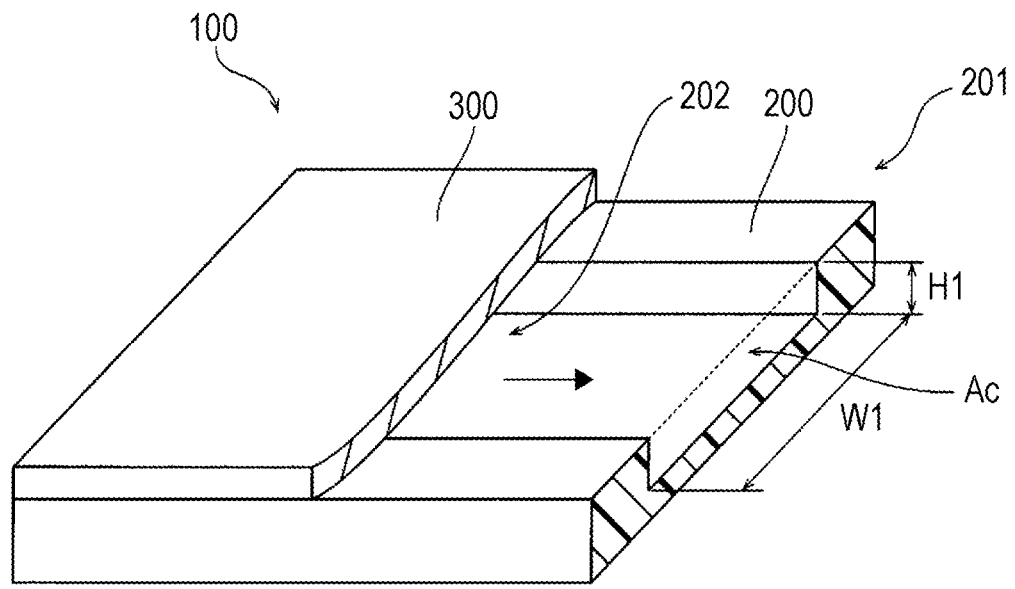
FIG. 12 is an enlarged perspective cross sectional view schematically illustrating a cross section of a channel of the flow-path in FIG. 11.

As illustrated in FIG. 12, the cross section of the channel 202 has the larger width W1 than a height H1. Namely, the channel 202 is flat and wide. The particles 22 are planarly distributed across the channel 202 to efficiently contact the process liquid 21, so that the target component 20 can efficiently be processed. The particles 22 retained in the channel 202 can efficiently be conveyed by the interface 23 since the fluid 24 adjusts its form along the cross section of the flow-path 201.

The channel 202 has a cross sectional area Ac of, for example, 0.01 $\mu m^2$ to 10 $mm^2$. The "cross sectional area of the channel 202" is the area of a cross section of the channel 202 normal to the flowing direction of the liquid. In the flow-path 201 having a channel 202 with a small cross sectional area Ac, it is difficult to increase the fluid flow velocity because of a high flow-path friction and an effect of fluid viscosity. Thus, the particles 22 are easily retained. With a small amount of liquid flowing in the flow-path 201 with a small total amount of the target component 20, remaining of the particles 22 in the flow-path 201 results in reduction in the collection rate of the finally collected sample. The method of processing a specimen according to the embodiment, which avoids remaining of the particles 22 by moving the interface 23, is effective for the flow-path 201 of such a size.

The flow-path 201 is provided as a part of the fluid module made of a block of resin or glass. The flow-path 201, or the fluid module, is preferably made of a material suitable for the processing performed in the flow-path 201. For example, polydimethylsiloxane (PDMS) and polymethylmethacrylate (PMMA) resin, which have hydrophobic property, are preferably used. Polycarbonate (PC), which has thermal resistance, is preferably used. Polycarbonate and polystyrene (PS), which have chemical resistance, are preferably used. Cycloolefin copolymer (COC) and cycloolefin polymer (COP), which have low autofluorescence, are preferably used for fluorescence detection. Glass and polycarbonate, which have high hydrophilic property, are preferably used to make hydrophilic processing easy.

The flow in the flow-path 201 is either a laminar flow or a disturbed flow. In the embodiment, for example, the target component 20 is processed in a laminar flow in the flow-path 201. In a laminar flow unlike a disturbed flow in which the liquid is mixed and flows in random directions, the velocity of the flow closer to the inner wall 11 of the flow-path 201 is smaller. Thus, in a laminar flow, the particles 22 are easily retained in the flow-path 201. The method of processing a specimen according to the embodiment, which avoids remaining of the particles 22 by moving the interface 23, is effective for processing the target component 20 in a laminar flow.

The flow in the flow-path 201 is represented by the Reynolds number Re. The Reynolds number Re is defined by Equation (1) expressed below.

$$Re = V \times d/v \quad (1)$$

V m/s is the average flow velocity in the flow-path 201, d m is the inner diameter of the flow-path 201, and v m$^2$/s is the dynamic viscosity of the fluid.

Generally, a flow of a Reynolds number Re of 2300 or below is a laminar flow. A flow in the flow-path 201 of a smaller inner diameter and a smaller flow velocity has a smaller Reynolds number. The particles 22 in a flow of a smaller Reynolds number are more easily retained in the flow-path 201. The method of processing a specimen according to the embodiment, which avoids remaining of the particles 22 by moving the interface 23, is effective for the processing of the target component 20 in a flow of a small Reynolds number. It is further effective in particular for a flow of a smaller Reynolds number in which the particles 22 are more easily retained.

For example, the target component 20 is processed in a flow of a Reynolds number preferably of 2000 or below in the flow-path 201. Preferably, the target component 20 is processed in a flow of a Reynolds number of 100 or below in the flow-path 201. More preferably, the target component 20 is processed in a flow of a Reynolds number of 10 or below in the flow-path 201.

For example, the fluid 24 is introduced into the flow-path 201 by a flow-rate of 0.1 μL/min to 5 mL/min. The flow-rate may be constant or vary within this range. The flow-rate from 0.1 μL/min to 5 mL/min is a very small flow-rate used in a micro-flow-path. Without supplying the fluid 24 by a flow-rate which is relatively very large for the dimension of the flow-path 201, the method of processing a specimen according to the embodiment can effectively avoid remaining of the particles 22 by moving the interface 23.

Figure 13:
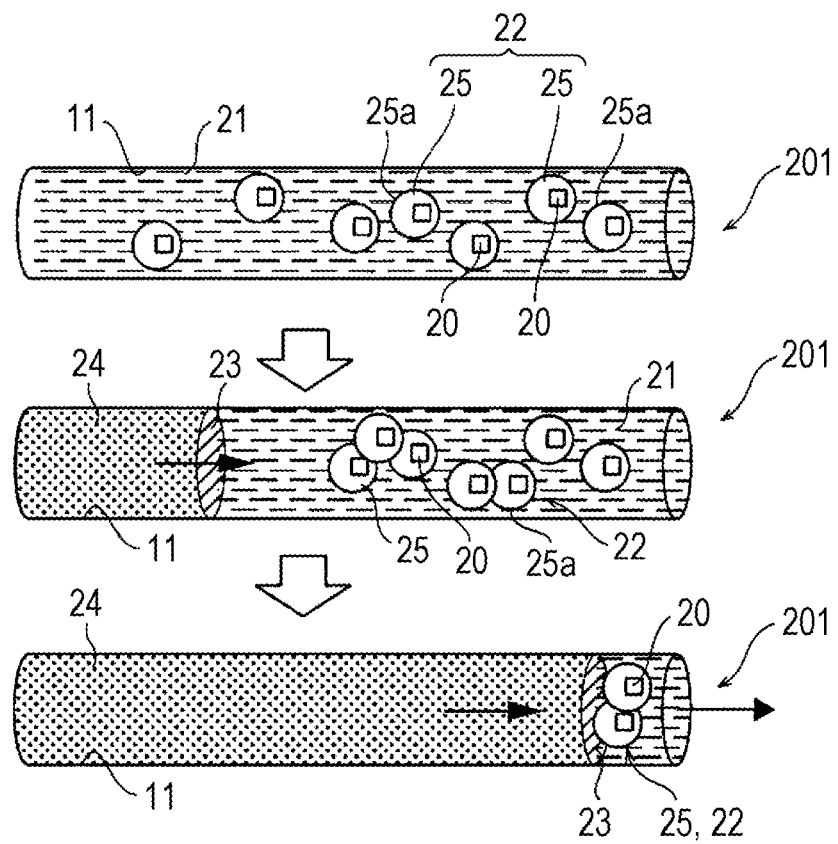
FIG. 13 illustrates another example method of processing a specimen where the particles are liquid particles.

FIG. 13 illustrates another method of processing a specimen. Particles 22 are liquid particles 25 in FIG. 13. The liquid particles 25 including the target component 20 are in a process liquid 21 in a flow-path 201. The liquid particle 25 in the process liquid 21 are formed by liquid particle interfaces 25a each divides each liquid particle 25 from the process liquid 21. The target component 20 is contained inside the liquid particle interface 25a. Each liquid particle 25 contains the target component 20 and is filled with a mixed liquid that forms the liquid particle interface 25a that divides the process liquid 21 from the mixed liquid. In FIG. 13, the target component 20 may not be processed in the flow-path 201. The flow-path 201 may be a flow-path for simply conveying liquid.

In the example in FIG. 13, the fluid 24 for forming an interface 23 that divides the liquid particle 25a from the process liquid 21 and is different from the liquid particle interfaces 25a forming the liquid particles 25 is introduced into the flow-path 201 that contains the process liquid 21 including the liquid particles 25 including the target component 20. The interface 23 is thereby formed with the rim of the interface 23 on the inner wall 11 of the flow-path 201. By moving the interface 23 along the flow-path 201, the liquid particles 25 in the process liquid 21 are conveyed along the flow-path 201.

For example, the liquid particle 25 is composed of a water phase liquid including the target component 20 and a reagent. The liquid particles 25 each having the liquid particle interface 25a are dispersed in the oil phase process liquid 21 such as oil. The fluid 24 is a gas phase liquid, such as air, and forms the interface 23 that divides the liquid particle 25 from the process liquid 21. The interface 23 is different from the liquid particle interface 25a.

When the liquid particles 25 dispersed in the process liquid 21 remain in the flow-path 201, the interface 23 different from the liquid particle interface 25a can be formed in the flow-path 201 with the rim of the interface 23 on the inner wall 11 by introducing the fluid 24. Then, the interface 23 is moved along the flow-path 201 to forcibly convey the liquid particles 25 retained in the process liquid 21 in the flow-path 201 together with the process liquid 21. In the specimen processing chip 100 provided with the flow-path 201 where the target component 20 is processed, remaining of the liquid particles 25 including the target component 20 in the flow-path 201 can be avoided.

Figure 14:
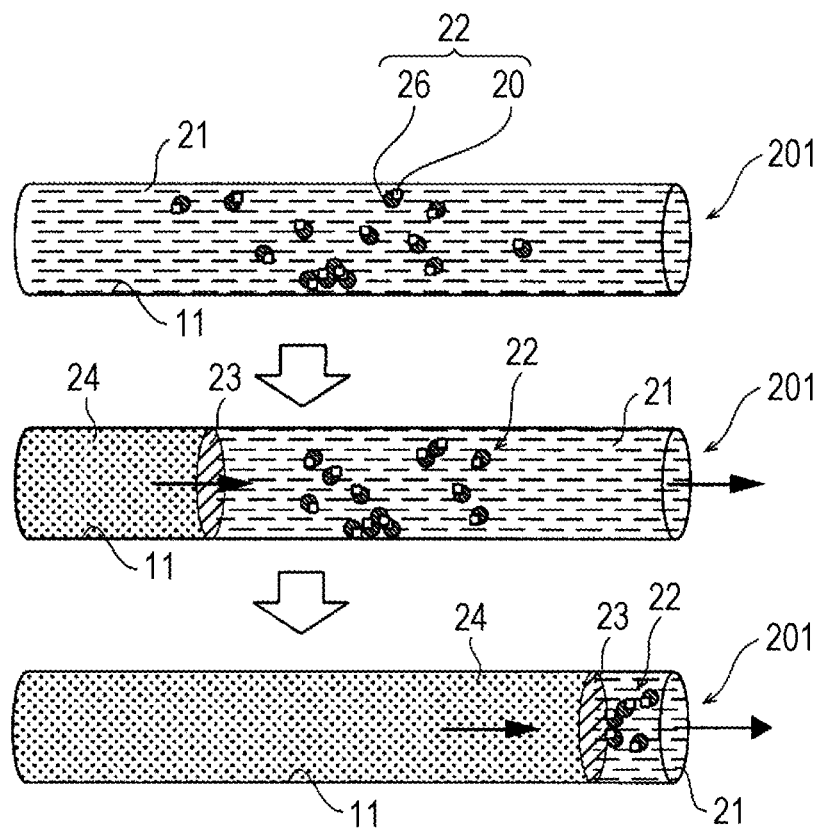
FIG. 14 illustrates another example method of processing a specimen where the particles are carriers.

FIG. 14 illustrates another method of processing a specimen. In FIG. 14, the particles 22 are solid carriers 26. The carriers 26 are surficially bonded to the target component 20. The target component 20 may be bonded by any type of bonding. In FIG. 14, the target component 20 may not be processed in the flow-path 201. The flow-path 201 may be a flow-path for simply conveying liquid.

The carriers 26 are, for example, known particles used for immunoassay. The particles are, for example, magnetic particles, latex particles, or gelatin particles. Magnetic particles are preferably used as the carriers 26. Any magnetic particle that includes a magnetic substance as a base material and used for immunoassay may be used. For example, the magnetic particles including $Fe_2O_3$ and/or $Fe_3O_4$, cobalt, nickel, phyllite, or magnetite as a base material can be used. The carriers 26 may be coated with a bonding material that bonds to the target component 20.

The carriers 26 are present in the process liquid 21. In the flow-path 201, the carriers 26 may aggregate near the inner wall 11.

In the example in FIG. 14, the fluid 24 is introduced into the flow-path 201 to form the interface 23 that divides the fluid 24 from the process liquid 21 with the rim of the interface 23 on the inner wall 11 of the flow-path 201. The interface 23 is moved along the flow-path 201 to convey the carriers 26 bonded to the target component 20 in the process liquid 21 along the flow-path 201.

In a case where the carriers 26 in the process liquid 21 are retained in the flow-path 201, the interface 23 is formed and moved along the flow-path 201 to forcibly convey the carriers 26 retained in the process liquid 21 in the flow-path 201 together with the process liquid 21. In the specimen processing chip 100 provided with the flow-path 201 where the target component 20 is processed, remaining of the liquid carriers 26 including the target component 20 in the flow-path 201 can be avoided.

When the carriers 26 are magnetic particles 26a, the magnetic particles 26a may be caught by a magnetic force. The magnetic particles 26a in the flow-path 201 are first magnetically caught and then released from the magnetic force. The magnetic particles 26a are then moved by the interface 23 of the fluid 24. When the magnetic particles 26a once magnetically caught adhere to the inner wall 11 of the flow-path 201, the magnetic particles 26a can be moved away from the inner wall 11 by the interface 23 of the fluid 24. As a result, remaining of the magnetic particles 26a once caught on the inner wall 11 in the flow-path 201 can effectively be avoided.

[Example Configuration of Specimen Processing Chip]

Figure 15:
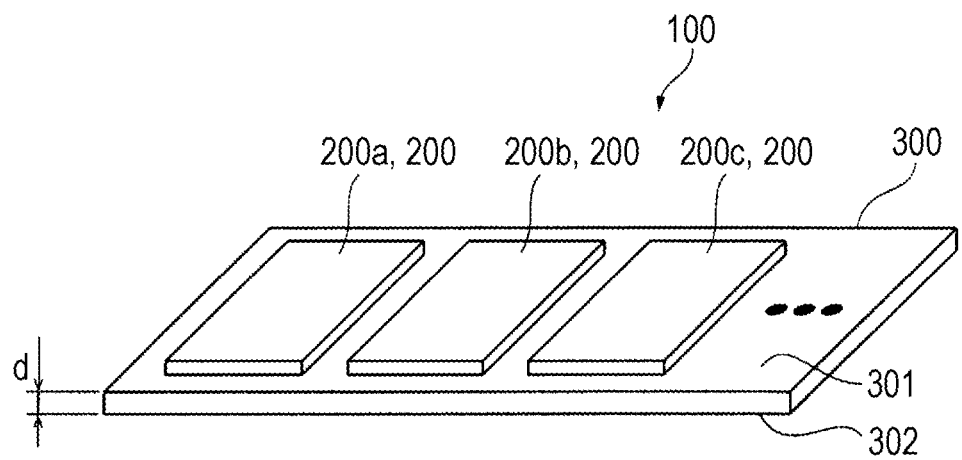
FIG. 15 is a perspective view illustrating an example specimen processing chip.

FIG. 15 is an example configuration illustrating a specimen processing chip 100 according to an embodiment. A plurality of types of fluid modules 200 having different functions are disposed on a base plate 300. In the example in FIG. 15, a specimen including a target component 20 or a reagent sequentially flow through the fluid modules 200a, 200b, and 200c, and an assay corresponding to the combination of the fluid modules is performed. The fluid modules 200a, 200b, and 200c are of different types. Different kind of assay can be performed by using different combination of fluid modules 200 disposed on the base plate 300. The number of fluid modules 200 disposed on the base plate 300 is not limited. The shape of the fluid module 200 may differ for different types of the fluid module 200.

Figure 16:
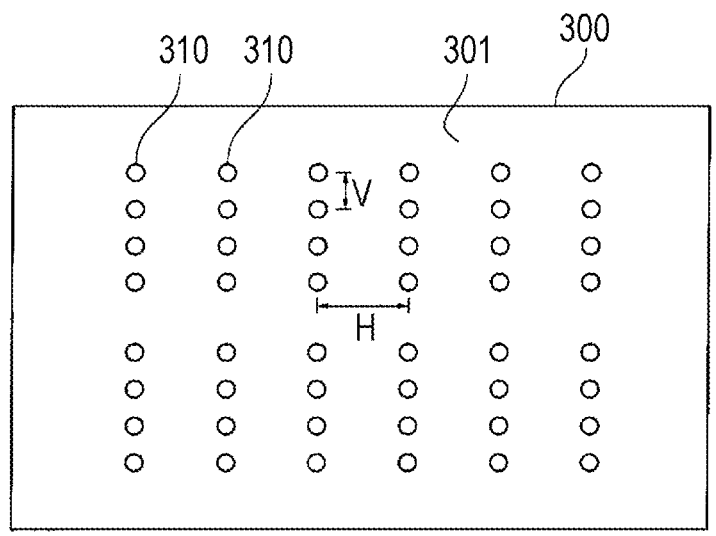
FIG. 16 is a plan view illustrating an example base plate of the specimen processing chip.

FIG. 16 illustrates an example configuration of the base plate 300. The base plate 300 includes a plurality of base flow-path 310. The base plate 300 has a form of a flat plate having a first face 301 and a second face 302 as main surfaces. The second face 302 is in the opposite side of the first face 301. The base plate 300 is made of, for example, resin or glass.

The base plate 300 has a thickness d of, for example, 1 mm to 5 mm. The base plate 300 has a height sufficiently larger than the height of the flow-path 201 provided in the fluid module 200 (the height is of the order of 10 μm to 500 μm). This gives the base plate 300 the sufficient pressure resistance without difficulty.

The base flow-path 310 is, for example, a through hole penetrating the base plate 300 in the thickness direction. The base flow-path 310 is connected to the flow-path 201 of the fluid module 200. The base flow-path 310 also serves as a port 110 (see FIG. 19) for supplying a liquid or a reagent to the fluid module 200 or a port 120 (see FIG. 19) for collecting a liquid from the specimen processing chip 100.

In the example in FIG. 16, the base plate 300 includes two groups of base flow-paths 310, each group consisting of the base flow-paths 310 disposed in four by six grid arrangement. The number of the base flow-paths 310 and the number of groups provided in the base plate 300 are not limited to those illustrated in FIG. 16.

The base flow-paths 310 are disposed, for example, by a certain pitch. In the example in FIG. 16, the base flow-paths 310 are disposed at pitch V in the longitudinal direction and at pitch H in the lateral direction. The fluid module 200 can be disposed at any position determined by a pitch on the base plate 300 to connect the flow-path 201 to an arbitrary base flow-path 310. The base flow-paths 310 may be provided only on locations necessary to connect the base flow-paths 310 to the fluid modules 200 disposed on the base plate 300.

Figure 17:
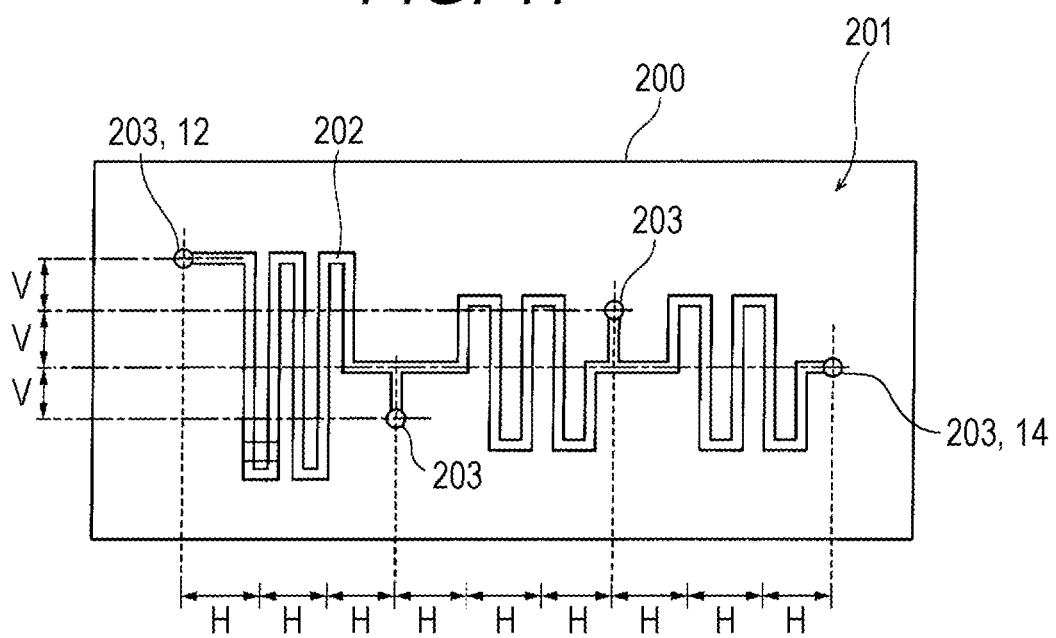
FIG. 17 is a plan view illustrating an example fluid module.

FIG. 17 is an example fluid module 200. The joints 203 are provided on the fluid module 200 at a pitch corresponding to the pitch of the base flow-paths 310 of the base plate 300. The pitches of the joints 203 provided on the fluid module 200 are multiples of the pitch V and the pitch H, which are the pitches of the base flow-paths 310 of the base plate 300. The channel 202 is provided so as to connect the joints 203 provided at predetermined pitches. A plurality of sets of the joints 203 located at predetermined pitches and the channel 202 are provided in the fluid module 200.

The fluid modules 200a to 200c may have different flow-path shapes. The fluid module 200 may be provided not only on the first face 301 but on the second face 302. The fluid module 200 may be provided only on the second face 302.

Figure 18:
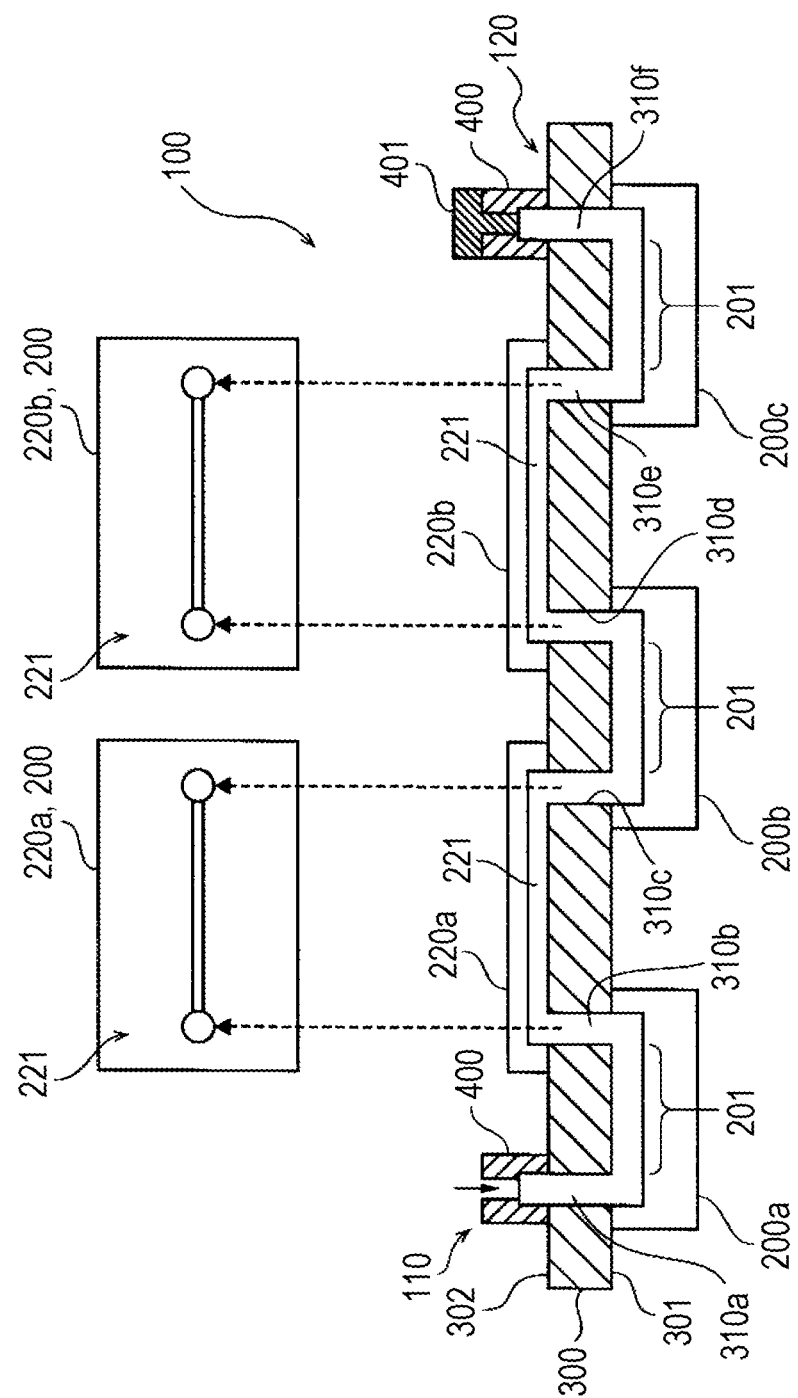
FIG. 18 is a longitudinal cross sectional view illustrating an example specimen processing chip.

In the example configuration in FIG. 18, the specimen processing chip 100 further includes a fluid module 220. The fluid module 220 is disposed on the second face 302 of the base plate 300. The second face 302 is on the opposite side of the first face 301 where the fluid module 200 is disposed. The fluid module 220 includes a flow-path 221 and also serves as a connection module that connects the fluid modules 200. The fluid module 220 is referred to as a connection module. The connection module 220 has no flow-path to perform a processing step of the target component 20. The base plate 300 may be provided with a flow-path like the connection module 220.

The fluid modules 200 (including the connection module 220) are bond to the base plate 300 by, for example, solid phase bonding. For example, the solid phase bonding may be performed by forming OH groups on the bonding surface by plasma treatment and then bonding together the bonding surfaces by hydrogen bonding, or alternatively, by vacuum pressure welding. The solid phase bonding firmly bonds together the fluid module 200 and the base plate 300. The fluid module 200 may be bonded to the base plate 300 by an adhesive.

In the example in FIG. 18, a base flow-path 310a of the base plate 300 serves as the port 110 for introducing liquid. A base flow-path 310f serves as the port 120 for collecting liquid. Any number of the ports 110 and the ports 120 may be provided.

The specimen, the process liquid 21, and the fluid 24 are introduced via an attachment such as a connector 400 into the base flow-path 310. The attachment, such as the connector 400, is connected to the base flow-path 310 at an end opposite the flow-path 201. Any base flow-path 310 can be plugged by inserting a plug 401 in the connector 400.

[Example Configuration of Specimen Processing Apparatus]

Figure 19:
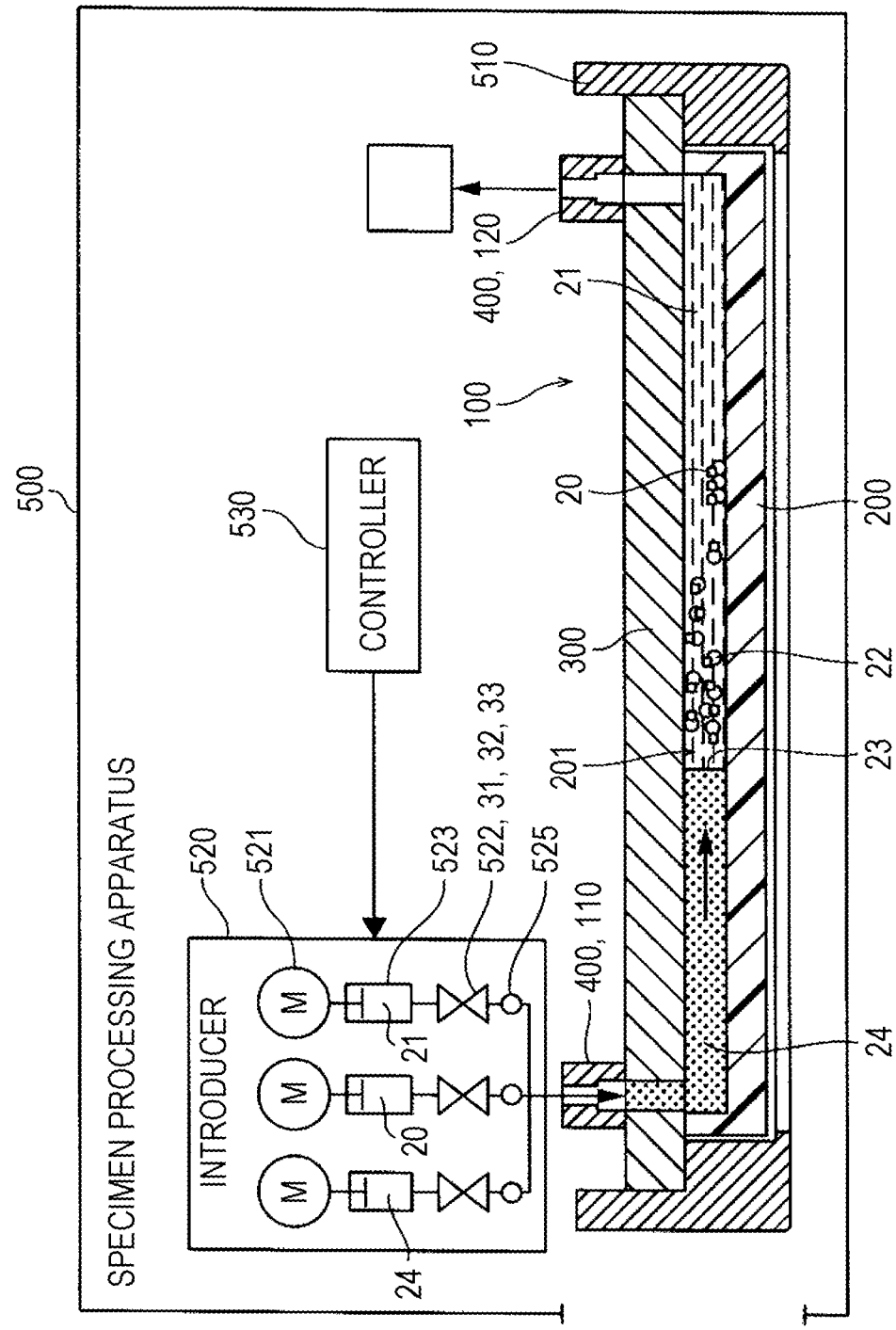
FIG. 19 schematically illustrates a specimen processing apparatus.

FIG. 19 schematically illustrates a specimen processing apparatus 500.

The specimen processing apparatus 500 uses a specimen processing chip 100 to perform processing of a target component 20 in a specimen. The specimen processing chip 100 which is to be used determines the processing of the specimen. The specimen processing apparatus 500 is capable of processing different types of specimens using different types of specimen processing chips 100.

The specimen processing apparatus 500 includes a chip base 510 where the specimen processing chip 100 provided with a flow-path 201 is disposed, an introducer 520, and a controller 530 that controls the introducer 520.

The chip base 510 has a form corresponding to the specimen processing chip 100 to support the specimen processing chip 100. The chip base 510 is openable to expose at least one of the top side and the bottom side of the specimen processing chip 100, so that the flow-path 201 of the specimen processing chip 100 can be connected and a processing unit used for processing steps performed in the specimen processing chip 100 can be set. The chip base 510 has a recess or has a frame shape, for example, to accommodate the specimen processing chip 100.

The introducer 520 introduces a liquid or a gas used for processing a specimen. The introducer 520 introduces a fluid 24 into the flow-path 201 of the specimen processing chip 100 to form an interface 23 that divides the fluid 24 from the process liquid 21. In the example in FIG. 19, the introducer 520 introduces the target component 20 and the process liquid 21 used for the processing of the target component 20 into the flow-path 201. The target component 20 and the process liquid 21 may previously be contained in the specimen processing chip 100 instead of being introduced by the introducer 520.

The introducer 520 provides a positive pressure to transfer the liquid in the specimen processing chip 100 according to the order of the steps as well as to discharge the liquid or gas out of the specimen processing chip 100. The introducer 520 may transfer and discharge liquid and gas in the specimen processing chip 100 by providing a negative pressure.

The controller 530 supplies the specimen including the target component 20 and the process liquid 21 to the flow-path 201 of the specimen processing chip 100 and controls the introducer 520 to perform the processing of the target component 20.

For the specimen processing apparatus 500 provided with the processing units used for performing processing steps, the controller 530 may control the processing units. The units for performing the processing steps are, for example, a heater unit or a cooling unit that controls the temperature of liquid, a magnetic unit that creates a magnetic force acting on the liquid, a camera unit that captures an images of the liquid, and a detecting unit that detects a specimen and a labeled matter in the liquid. Each of the processing units corresponds to at least one of a plurality of fluid modules 200. The processing unit operates during the processing step performed in the corresponding fluid module 200.

In the embodiment, the introducer 520 introduces the fluid 24 into the flow-path 201 to form the interface 23 that divides the fluid 24 from the process liquid 21 containing the particles 22 including the target component 20 with the rim of the interface 23 on the inner wall 11 of the flow-path 201. The introducer 520 moves the interface 23 along the flow-path 201 with the rim of the interface 23 on the inner wall 11 to force out the particles 22 retained in the process liquid 21 by the fluid 24. The introducer 520 forms the interface 23 of the fluid 24 in the flow-path 201 as illustrated in FIG. 2. The introducer 520 controls conveyance of the particles 22 along the flow-path 201 by moving the interface 23 along the flow-path 201.

For the particles 22 retained in the flow-path 201 during the processing of the target component 20 in the flow-path 201, the fluid 24 is introduced to form in the flow-path 201 the interface 23 that divides the fluid 24 from the process liquid 21 with the rim of the interface 23 on the inner wall 11. Then, the interface 23 is moved along the flow-path 201 to forcibly convey the particles 22 retained in the flow-path 201 together with the process liquid 21. Accordingly, in the specimen processing chip 100 provided with the flow-path 201 where the target component 20 is processed, remaining of particles 22 including the target component 20 in the flow-path 201 can be avoided.

As exemplarily illustrated in FIG. 2, for example, the introducer 520 forces the particles 22 retained in the process liquid 21 out of the specimen processing chip 100 by the introduced fluid 24. In such a manner, the process liquid 21 in the downstream of the interface 23 is forced out of the specimen processing chip 100 together with the retained particles 22, which enables collecting a large number of particles 22 while suppressing the increase in the amount of the sample collected from the specimen processing chip 100 compared to, for example, a method in which a great amount of the process liquid 21 is introduced in the flow-path 201 to force out the retained particles 22.

The introducer 520 moves the interface 23 along the flow-path 201 to move the retained particles 22 away from the inner wall 11 of the flow-path 201, thereby conveying the particles 22 along the flow-path 201. In this manner, the particles 22 retained on the inner wall 11 of the flow-path 201 are forcibly moved away from the inner wall 11 by the approaching interface 23. This effectively avoids remaining of the particles 22 retained particularly near the inner wall 11 of the flow-path 201 where the flow velocity is low and therefore conveyance of the particles 22 is very difficult.

As illustrated in FIG. 3, the introducer 520 may move the interface 23 along the flow-path 201 to let the interface 23 contact the particles 22 retained on the inner wall 11. In this manner, the moving interface 23 contacts the particles 22 adhering to the inner wall 11 of the flow-path 201 to apply a force that rips off the particles 22 from the inner wall 11. As a result, even for the particles 22 adhering to the inner wall of the flow-path 201, remaining of the particles 22 in the flow-path 201 can further effectively be avoided.

Figure 20:
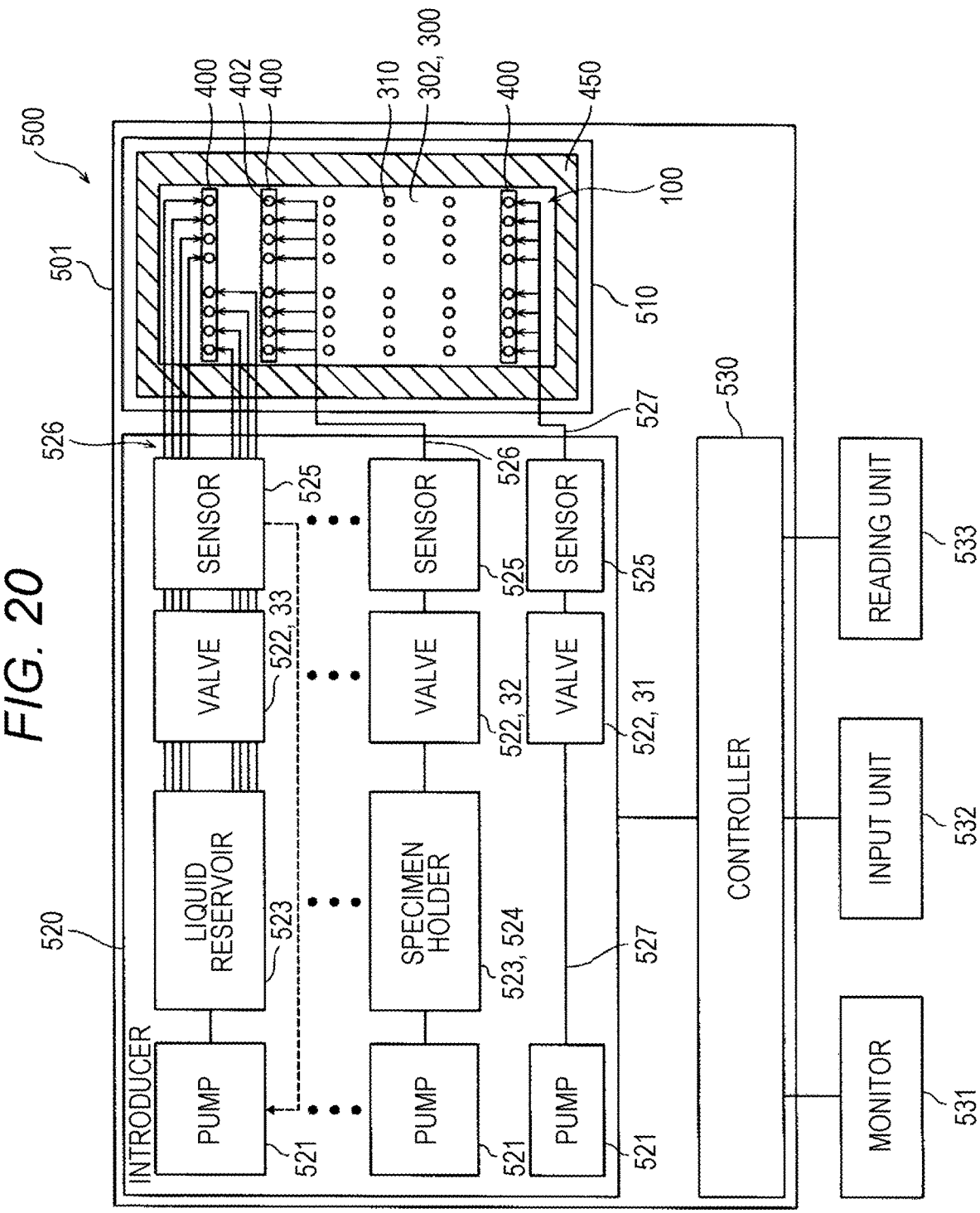
FIG. 20 is a block diagram illustrating an example specimen processing apparatus.

FIG. 20 illustrates an example configuration of the specimen processing apparatus 500. In the example configuration illustrated in FIG. 20, the introducer 520 includes a pump 521 that pressurizes the flow-path 201, and a plurality of valves 522 for opening and closing the pressure lines to the flow-path 201. The introducer 520 includes a liquid reservoir 523 that stores a liquid which is introduced into the specimen processing chip 100, and a specimen holder 524. The introducer 520 is equipped with a flow rate sensor 525 for measuring the flow rate of the liquid flowing in the specimen processing chip 100.

The pump 521, the liquid reservoir 523, the valve 522, and the flow rate sensor 525 are connected in this order by a supply tube 526. The specimen processing apparatus 500 uses the pump 521, the liquid reservoir 523, and the valve 522 to introduce the liquid into the specimen processing chip 100 and collect the liquid from the specimen processing chip 100 via the connector 400. In the example in FIG. 20, each set of the pump 521, the liquid reservoir 523, and the valve 522 is connected to corresponding connector 400. At least one liquid reservoir 523 serves as the specimen holder 524 that holds the specimen.

The liquid reservoir 523 serving as the specimen holder 524 may be provided in the specimen processing chip 100. In such a case, a sleeve-like liquid reservoir is provided on the port 110 from which the specimen is introduced. The liquid reservoir 523 for collecting a sample of the processed target component 20 from the specimen processing chip 100 may be provided on the port 120 from which the liquid is collected.

A plurality of liquid reservoirs 523 and a plurality of valves 522 may be connected to the single pump 521. By switching the lines by the valves 522, a plurality of types of liquid and reagent are supplied to the specimen processing chip 100 using the common pump 521.

The pump 521 pressurizes the liquid reservoir 523 and the specimen holder 524. The pump 521 provides a positive pressure to send out the liquid from the liquid reservoir 523. The pump 521 provides a negative pressure to supply the liquid from the specimen processing chip 100 to the liquid reservoir 523. The pump 521 is, for example, a pressure pump that supplies air pressure. Alternatively, a syringe pump or a diaphragm pump may be used as the pump 521.

When a liquid is used as the fluid 24, at least one of the liquid reservoirs 523 stores the fluid 24.

When a gas is used as the fluid 24, a gas reservoir (not shown) that gas-tightly holds a gas may be provided. When air is used as the fluid 24, the introducer 520 includes the air line 527 in which air flows between the pump 521 and the valve 522 and between the valve 522 and the specimen processing chip 100. Air can be supplied from the atmosphere surrounding the specimen processing apparatus 500.

The pump 521 pressurizes the specimen processing chip 100 via the air line 527 to introduce air, or the fluid 24, into the flow-path 201. Using air as the fluid 24, the interface 23 can easily be formed for various types of the process liquid 21. Unlike using a liquid as the fluid 24, the liquid amount in the flow-path 201 does not increase, and thus the increase in the liquid amount of the finally collected sample containing the particles 22 including the target component 20 is suppressed. Unlike using a specific gas other than air as the fluid 24, the air as the fluid 24 can be obtained easily and introduced into the flow-path 201 via the air line 527.

The controller 530 controls opening and closing of the valves 522 of each introducer 520 to transfer by pressure the liquid or the gas into the specimen processing chip 100. The controller 530 controls the timing of opening the valves 522 based on, for example, the time elapsed after introducing the liquid into the specimen processing chip 100 or the amount of the liquid or gas introduced into the specimen processing chip 100.

At least one of the valves 522 serves as the valve 31 for introducing the fluid 24 into the flow-path 201. At least one of the valves 522 serves as the valve 32 for introducing the particles 22 into the flow-path 201. At least one of the valves 522 serves as the valve 33 for introducing the process liquid 21 into the flow-path 201.

The introducer 520 opens and closes the valve 31 to form the interface 23 between the process liquid 21 and fluid 24 which are introduced in the flow-path 201. The introducer 520 opens and closes the valve 31 to move the interface 23 by pressure. The interface 23 of the fluid 24 can easily be formed by opening and closing the valve 31. By regulating the pressure of the pump 521 and the opened period and the number of opening and closing of the valve 31, the amount of the fluid 24 introduced and the number of interfaces 23 formed can be controlled. The interface suitable for the flow-path shape and the particles 22 can thus be formed.

For example, the introducer 520 opens and closes the valve 33 for introducing the process liquid 21 and the valve 31 for introducing the fluid 24 alternately to interpose the fluid 24 in the flow of the process liquid 21 in the flow-path 201. An interposed region 28 of the fluid 24 (see FIG. 4) having the interfaces 23 on both ends is thus formed in the process liquid 21. By simply interposing the fluid 24 midway in the flow of the process liquid 21, two interfaces 23 are formed to divide the process liquid 21 from the fluid 24. By moving the interposed regions 28 of the fluid 24 together with the process liquid 21, the particles 22 that the first interface 23 has failed to convey along the moving direction can be conveyed by the second interface 23. The conveyance efficiency of the interface 23 can thus be improved. By a simple control of alternately regulating opening and closing of only the valves 522 (31 and 33), the interposed region 28 of the fluid 24 is easily formed in the flow-path 201.

The controller 530 controls the operation of each pump 521 independently. The controller 530 independently controls each pump 521 to regulate supply of liquids suitable for the combination of the fluid modules 200 mounted on the specimen processing chip 100.

The flow rate sensor 525 in FIG. 20 detects the flow-rate (for example, by a unit of µL/min) of the liquid or gas flowing in the supply tube 526. The flow rate sensor 525 feeds back the detected flow-rate to the pump 521. The pump 521 controls the pressure according to the feedback from the flow rate sensor 525. The flow rate sensor 525 may give a feedback to the controller 530. Based on the flow-rate measured by the flow rate sensor 525, the controller 530 controls the pressure at the introducer 520 to transfer the liquid.

The connector 400 is connected to the supply tube 526. The liquid, such as a specimen, is supplied to the specimen processing chip 100 via the connector 400. The liquid is collected from the specimen processing chip 100 via the connector 400.

The specimen processing chip 100 is set in the chip base 510. For example, the specimen processing chip 100 is held with the second face 302 of the base plate 300 facing upward to connect the end of the base flow-path 310 opposing the second face 302 to the connector 400.

The specimen processing chip 100 may be equipped with a fixing device 450 to set the specimen processing chip 100 to the chip base 510. The fixing device 450 may be separable from the chip base 510 or fixed to the chip base 510.

The specimen processing apparatus 500 may be equipped with a monitor 531, an input unit 532, and a reading unit 533. The controller 530 presents a predetermined display screen corresponding to an operation of the specimen processing apparatus 500 on the monitor 531. The specimen processing apparatus 500 may presents a screen on a monitor of an external computer (not shown) connected to the specimen processing apparatus 500. The input unit 532 comprises, for example, a keyboard to receive input information. The reading unit 533 comprises, for example, a code reader that reads a bar code or a two-dimensional code and a tag reader that reads an RFID tag. The reading unit 533 reads information given to the specimen processing chip 100. The reading unit 533 can also read information on a specimen container (not shown) that contains a specimen including the target component.

(Example Configuration of Valve)

Figure 21:
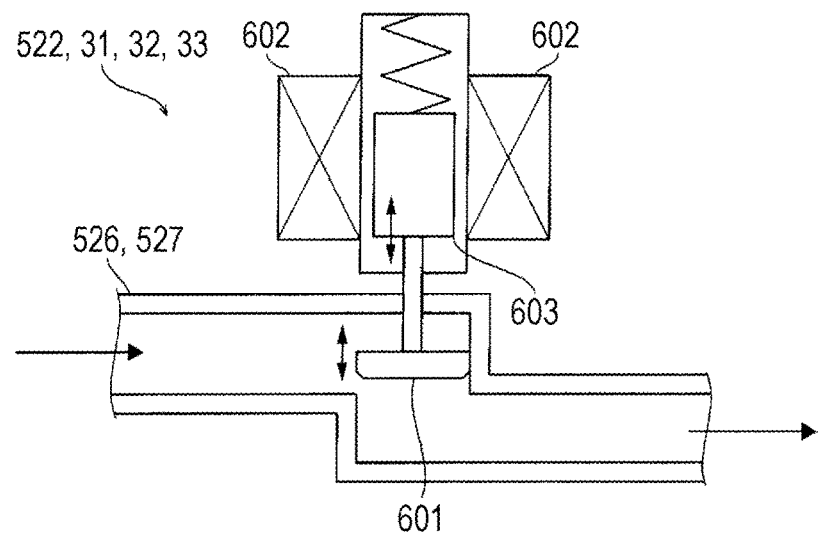
FIG. 21 is a cross sectional view illustrating an example valve.

FIG. 21 illustrates an example configuration of the valve 522 (31, 32, and 33). The valve 522 is, for example, an electromagnetic valve. The valve 522 includes a valve 601, a coil 602, and a plunger 603. The valve 601 opens and closes the supply tube 526. As illustrated in FIG. 20, a plurality of valves 522 is disposed in the specimen processing apparatus 500. The controller 530 controls opening and closing of each valve 522 independently.

(Example Configuration of Liquid Reservoir and Specimen Holder)

Figure 22:
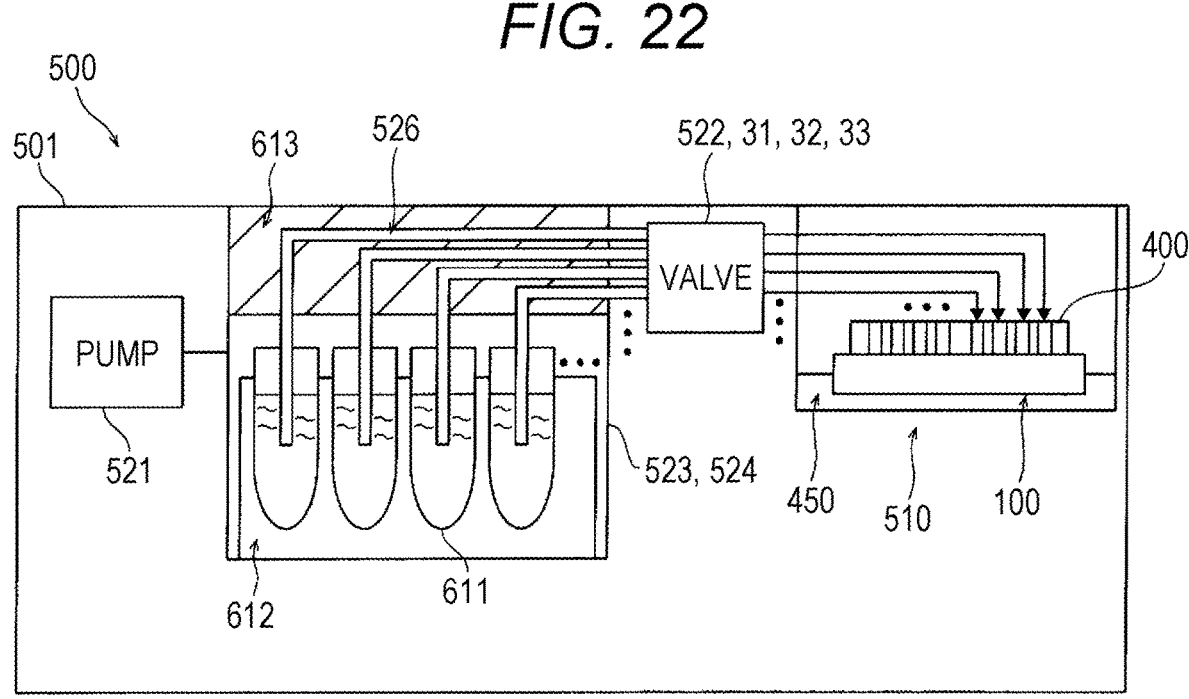
FIG. 22 is a longitudinal cross sectional view illustrating an example liquid reservoir.

FIG. 22 illustrates an example configuration of the liquid reservoir 523 and the specimen holder 524.

Liquid containers 611 for specimens and reagents are disposed in a container receiver 612 in the liquid reservoir 523 and the specimen holder 524. As illustrated in FIG. 22, a single or a plurality of container receivers 612 may be provided.

The supply tubes 526 provided on a lid 613 of the container receiver 612 are connected to the specimen processing chip 100 via the valve 522. By raising the pressure in the liquid reservoir 523 and opening the valve 522, the liquid in the container 611 is supplied to the specimen processing chip 100.

(Example Configuration of Chip Base Lid)

Figure 23:
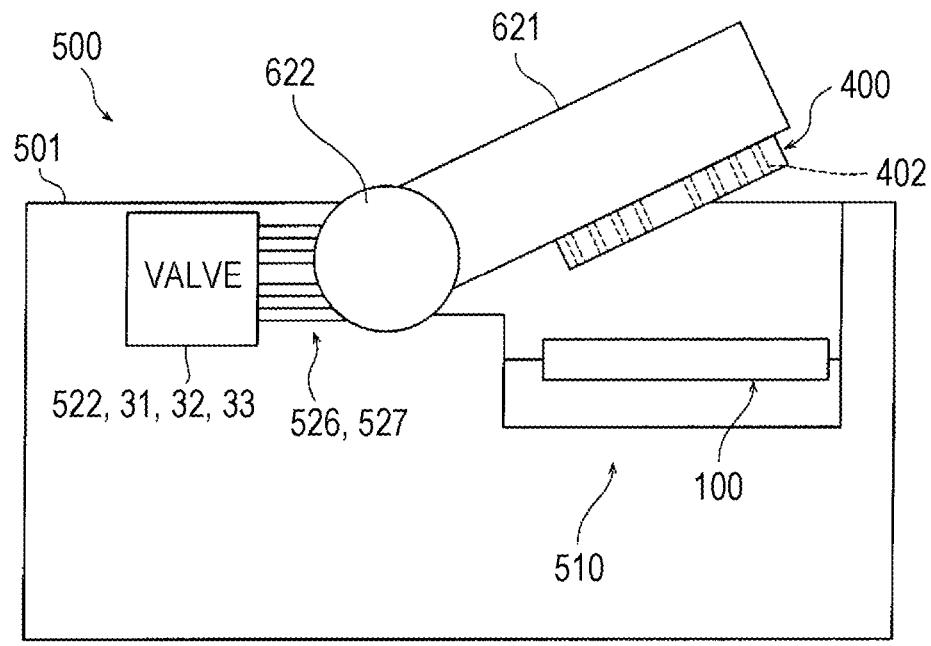
FIG. 23 is a longitudinal cross sectional view illustrating an example chip base.

The chip base 510 may be provided with a dedicated lid 621. FIG. 23 illustrates an example configuration of the lid 621 of the chip base 510. The lid 621 is provided to cover the specimen processing chip 100 set in the chip base 510.

The lid 621 is joined to a specimen processing apparatus body 501 by a hinge 622. The hinge 622 rotates to open and close the lid 621. The lid 621 may include the connector 400. By simply closing the lid 621 of the chip base 510, the specimen processing chip 100 set in the chip base 510 is connected to the connector 400. The lid 621 may be detachably attached to the specimen processing apparatus body 501. In such a case, the hinge 622 may not be provided.

(Example Configuration of Connector)

Figure 24:
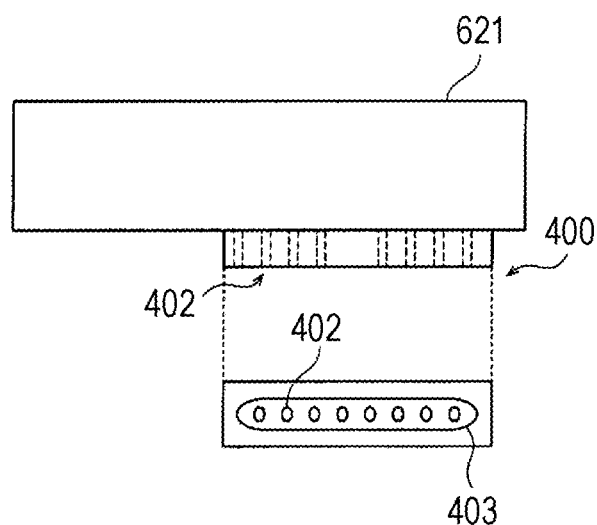
FIG. 24 illustrates an example connector.

FIG. 24 illustrates an example configuration of the connector 400. The connector 400 is provided on the lid 621. The connector 400 has holes 402 to provide access to the base flow-paths 310 of the base plate 300. The connector 400 is set at a position corresponding to the base flow-paths 310 of the base plate 300. The connector 400 may be set in a position that only corresponds to arbitrarily selected base flow-paths 310. The connector 400 may be a manifold provided with a plurality of supply tubes 526 and air lines 527. In this case, the supply tubes 526 and the air lines 527 are connected to all the ports 110 and 120 of the specimen processing chip 100 via the connector 400 by closing the lid 621.

The liquid, such as a specimen and a reagent, is introduced from the supply tube 526 into the specimen processing chip 100 via the hole 402. The liquid flowing in the specimen processing chip 100 is collected from the specimen processing chip 100 via the hole 402. The connector 400 is provided with a sealing material, such as a gasket 403, on the contact face of the specimen processing chip 100 to prevent leakage of liquid and contamination of objects.

<Example Configuration of Fixing Device>

Figure 25:
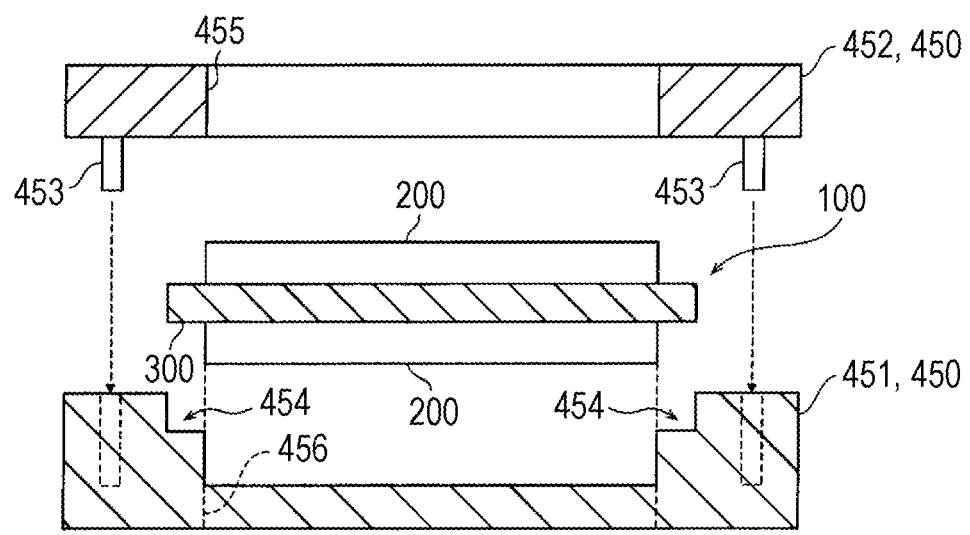
FIG. 25 is an exploded view illustrating an example fixing device.
Figure 26:
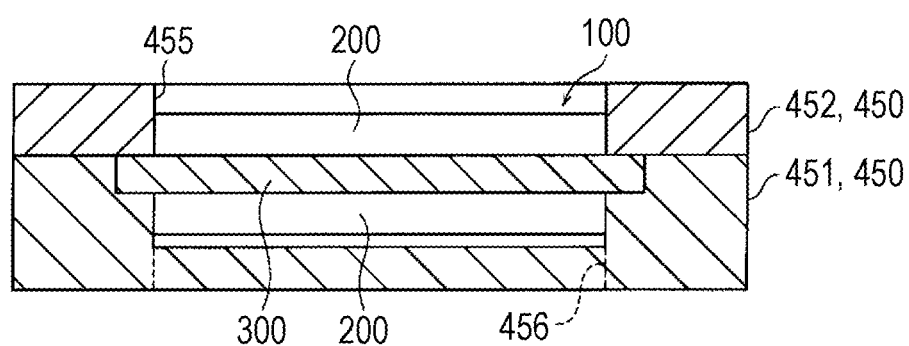
FIG. 26 illustrates a fixing device in which the specimen processing chip is fixed.

FIGS. 25 to 27 illustrate an example of the fixing device 450 used to set the specimen processing chip 100 in the specimen processing apparatus 500.

As illustrated in FIG. 25, the specimen processing chip 100 is fixed, for example, by fixing devices 451 and 452. The fixing devices 451 and 452 are fixed by fitting members 453. Positioning sections 454 determine the relative position of the specimen processing chip 100 to the fixing devices 451 and 452. The specimen processing chip 100 is fixed by the fixing devices 451 and 452 as illustrated in FIG. 26.

Figure 27A:
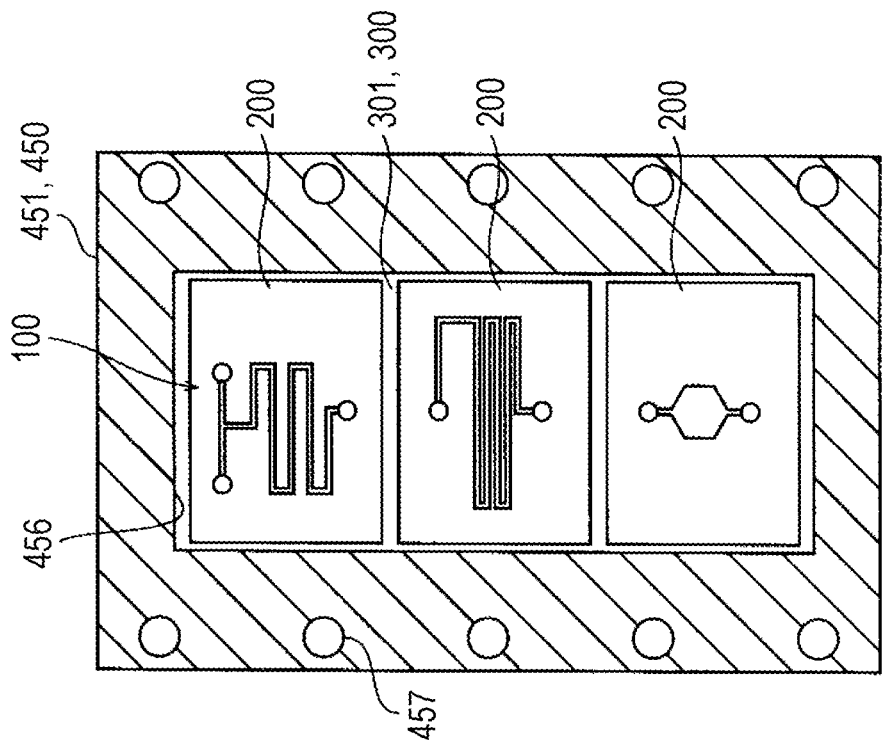
FIG. 27A is a top view of the fixing device in FIG. 26.
Figure 27B:
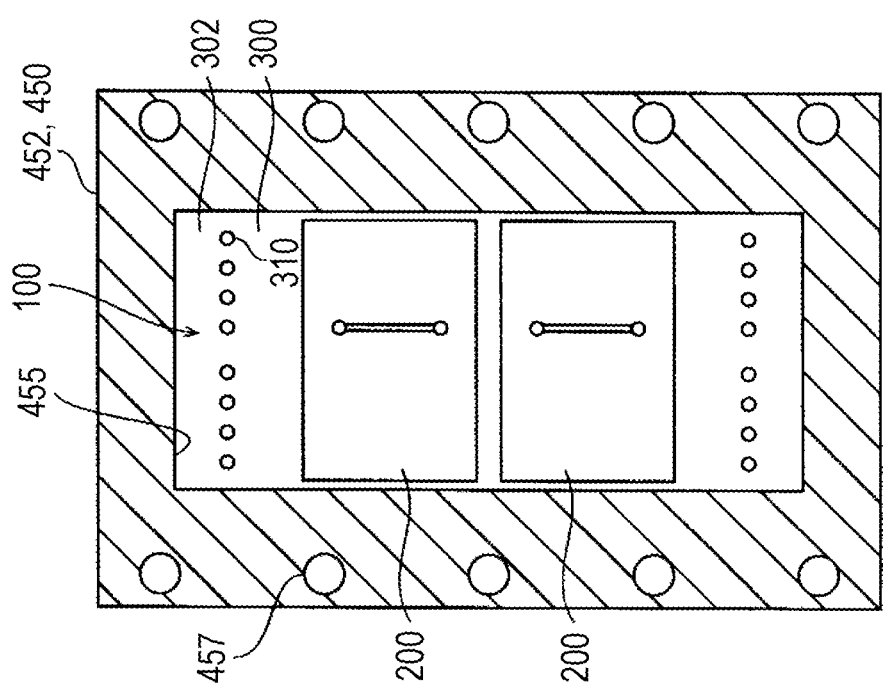
FIG. 27B is a bottom view of the fixing device in FIG. 26.

As illustrated in FIG. 27A, the fixing device 452 has an aperture 455, which is a through hole, where the base plate 300 comes. Parts, such as the connector 400 of the specimen processing apparatus 500, are accessible from above the base plate 300 via the aperture 455. As illustrated in FIG. 27B, the fixing device 451 has an aperture 456, which is a through hole, where the base plate 300 and the fluid module 200 come. The base plate 300 and the fluid module 200 are accessible from below via the aperture 456.

The fixing device 452 may be fixed to the lid 621 of the chip base 510. The fixing devices 451 and 452 may have securing holes 457 to position the processing units set in the specimen processing apparatus 500.

(Example Setting of Processing Units)

Figure 28A:
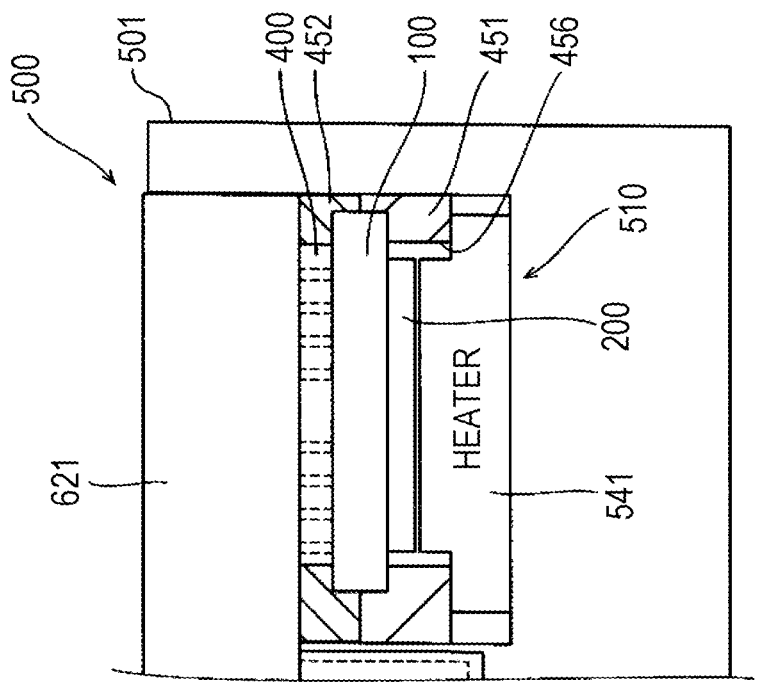
FIG. 28A is a bottom view illustrating an example disposition of a heater unit.
Figure 28B:
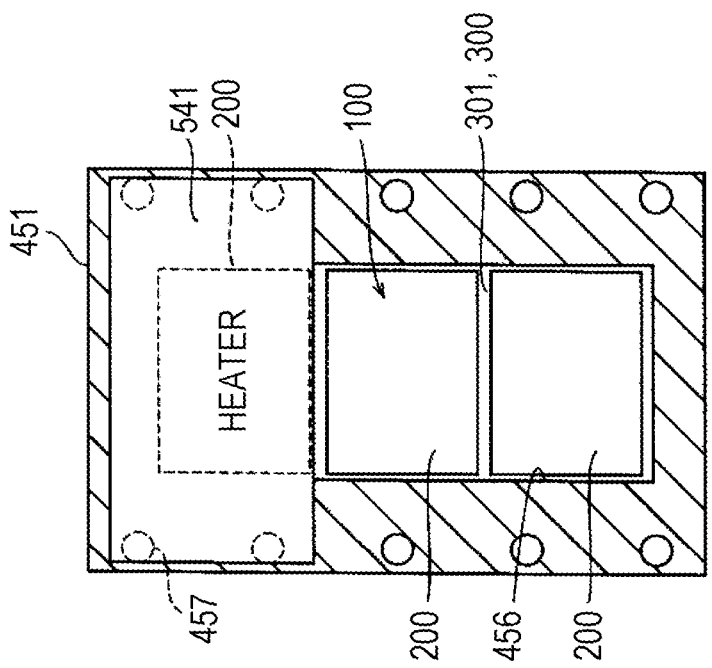
FIG. 28B is a cross sectional view schematically illustrating an example disposition of the heater unit in the chip base.

FIGS. 28 to 30 illustrate example settings of the processing units used for processing steps performed in the specimen processing apparatus 500.

For example, processing units such as a heater unit (heater 541) that heats the liquid in the fluid module 200, a magnetic unit 542 (see FIG. 30) that creates a magnetic force acting on the liquid in the fluid module 200, a cooling unit (not shown) that cools the liquid in the fluid module 200, a detecting unit (detector 544, see FIG. 29) that detects the target component in the specimen processing chip 100, and a camera unit (not shown) that captures an image of the liquid flow in the fluid module 200 are mounted using the securing holes 457 on the fixing device 451 or 452. The connector 400 may be mounted on the fixing device 451 or 452. The unit may be a combined unit having some of the functions described above. For example, such a unit that has a function of heating the liquid and a function of creating a magnetic force acting on the liquid may be used.

<Heater Unit>

FIG. 28 illustrates an example setting of the heater 541 in the specimen processing apparatus 500.

The heater 541 adjusts the temperature of the specimen processing chip 100. For example, the heater 541 heats the specimen processing chip 100 to amplify DNA by PCR in the fluid module 200.

The heater 541 is provided in the chip base 510. For example, the heater 541 is attached to the fixing device 451 on the bottom side of the specimen processing chip 100. The heater 541 adjusts from the bottom side the temperature of the specimen processing chip 100 set in the chip base 510. The heater 541 may be attached to the lid 621 or the fixing device 452 on the upper side. The heater 541 is positioned where the fluid module 200 of which temperature is to be adjusted is set. The heater 541 may be movable.

<Detecting Unit>

FIG. 29 is an example configuration of the detector 544 of the specimen processing apparatus 500.

The detector 544 detects, for example, fluorescence of a labeled matter bond to the target component. The detector 544 is, for example, a photomultiplier. For example, the detector 544 is attached to the fixing device 452 on the top side of the specimen processing chip 100. The detector 544 may be provided on the lid 621. The detector 544 detects fluorescence through the connector 400 connected to the specimen processing chip 100. The detector 544 may be provided on the fixing device 451 on the bottom side of the specimen processing chip 100 or on the specimen processing apparatus body 501. In such a case, the detector 544 detects fluorescence from the bottom side of the specimen processing chip 100.

<Magnetic Unit>

FIG. 30 illustrates an example configuration of the magnetic unit 542 used for controlling the magnetic particles 26a contained in the liquid in the specimen processing chip 100.

For example, the magnetic unit 542 is attached to the fixing device 451 on the bottom side of the specimen processing chip 100. The magnetic unit 542 may be provided on the specimen processing apparatus body 501. The magnetic unit 542 may be attached to the lid 621 or the fixing device 452 on the upper side. The magnetic unit 542 includes a magnet 640. The magnet 640 creates a magnetic force acting on the magnetic particles 26a contained in the liquid in the specimen processing chip 100. The magnetic unit 542 allows the magnet 640 to move, for example, in the longitudinal direction of the specimen processing chip 100.

As illustrated in FIG. 10, when the target component 20 is nucleic acid and the particles 22 are magnetic particles 26a bonded to nucleic acid, for example, the magnetic particles 26a are magnetically caught in the flow-path 201 by the magnetic unit 542. The magnetic particles 26a magnetically caught in the flow-path 201 are gathered at a location and therefore easily aggregate. The magnetic particles 26a magnetically pressed against the inner wall 11 of the flow-path 201 are easily retained on the inner wall 11.

The specimen processing apparatus 500 is controlled such that, after the magnetic particles 26a bonded to nucleic acid in the flow-path 201 are magnetically caught and then released, the magnetic particles 26a are moved by the interface 23 of the fluid 24. When the magnetic particles 26a once magnetically caught adhere to the inner wall 11 of the flow-path 201, the moving interface 23 of the fluid 24 can move the magnetic particles 26a away from the inner wall 11. As a result, remaining of the magnetic particles 26a once caught on the inner wall 11 in the flow-path 201 can effectively be avoided.

Although not shown in the drawing, the camera unit and the cooling unit are controlled in a similar manner.

[Example Assay Using Specimen Processing Chip]

A specific example assay using the specimen processing chip 100 will now be described.

(Emulsion PCR Assay)

An example of emulsion PCR assay using the specimen processing chip 100 will now be described.

Figure 31:
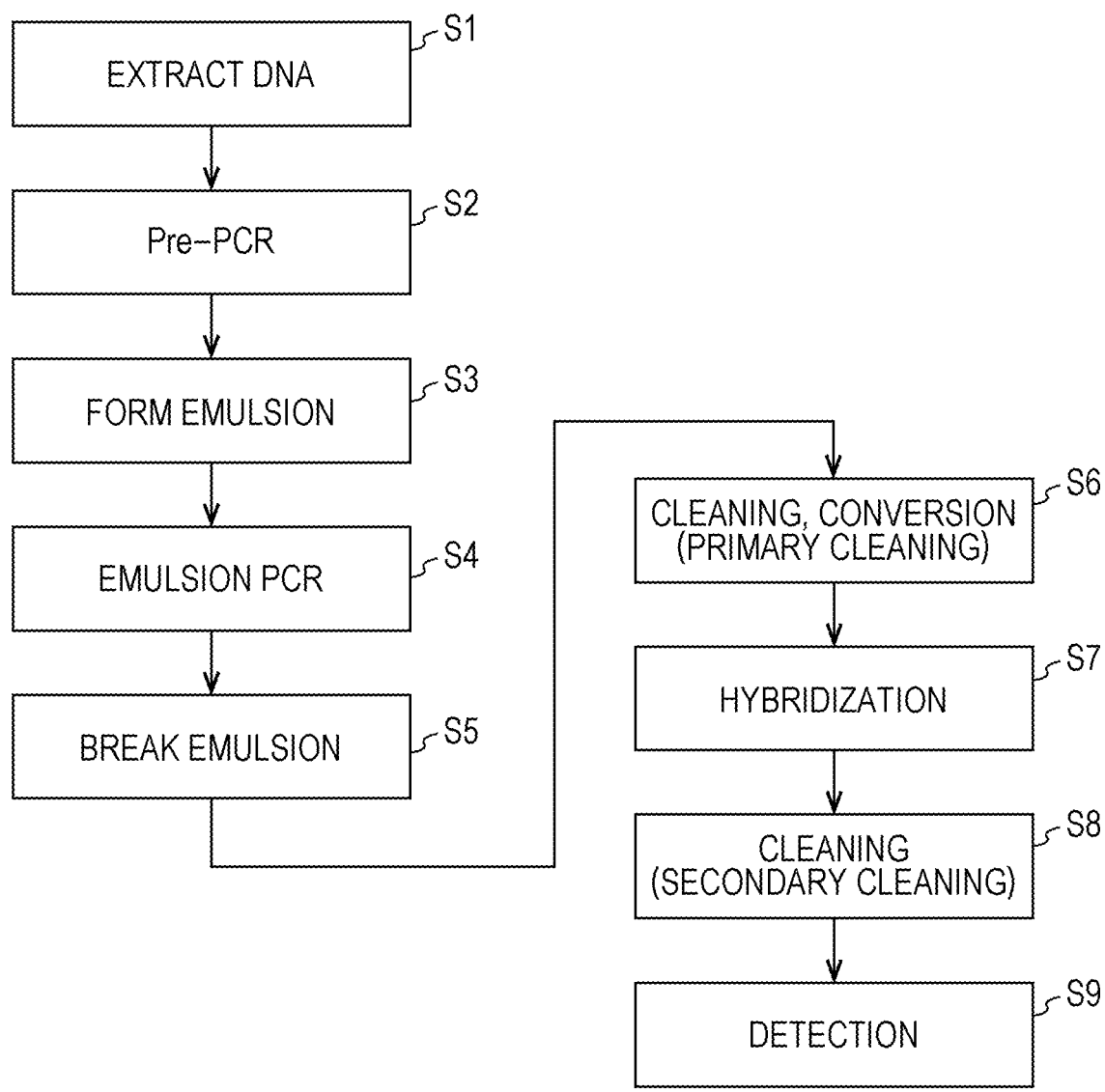
FIG. 31 is a flowchart illustrating an example of emulsion PCR assay.
Figure 32:
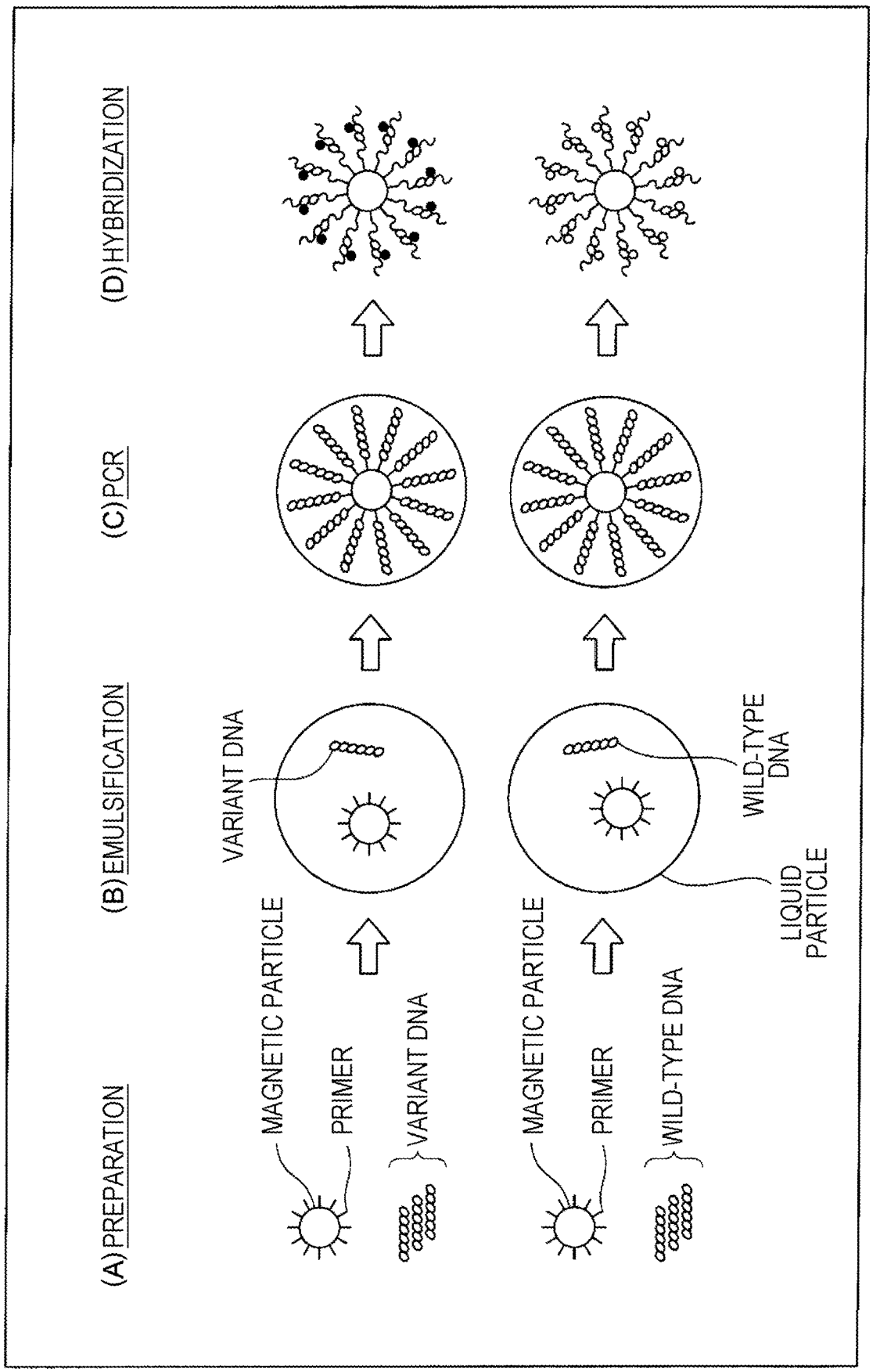
FIG. 32 illustrates reaction steps in the emulsion PCR assay.

FIG. 31 is an example flow of emulsion PCR assay. FIG. 32 illustrates reaction steps in the emulsion PCR assay.

In step S1, DNA is extracted from a sample, such as blood sample, by pre-processing (see (A) in FIG. 32). The pre-processing may be performed using a dedicated nucleic acid extraction device or by a pre-processing mechanism provided in the specimen processing apparatus 500.

In step S2, the extracted DNA is amplified by Pre-PCR (see (A) in FIG. 32). In the Pre-PCR, the DNA contained in the extraction liquid resulting from the pre-processing is previously amplified to such an amount sufficient to perform the subsequent processing of producing emulsion. In the Pre-PCR, the extracted DNA is mixed with a PCR amplifying reagent including polymerase and primer, and then the DNA in the mixed liquid is amplified by controlling temperature by a thermal cycler. The thermal cycler performs thermal cycle processing on the mixed liquid, which thermal cycle processing includes a plurality cycles of setting the temperature to different values.

Step S3 is an emulsion forming step in which liquid particles including a mixed liquid of nucleic acid (DNA), which is the target component, a reagent for nucleic acid amplification reaction, and carriers of nucleic acid are formed in a dispersion media. The reagent for nucleic acid amplification reaction includes a substance necessary for PCR, such as DNA polymerase. In step S3, emulsion containing the reagent, including magnetic particles and polymerase, and DNA is produced (see (B) in FIG. 32). Emulsion is a dispersion solution in which a liquid that does not mix with a dispersion media is dispersed in the dispersion media. In step S3, liquid particles containing the mixed liquid of the reagent, including the magnetic particles and polymerase, and DNA is formed. A large number of the liquid particles are dispersed in the dispersion media. The magnetic particles contained in the liquid particles have on their surfaces primers for amplifying nucleic acid. Each liquid particle is formed so as to include a magnetic particle and a DNA molecule. The dispersion media is immiscible in the mixed liquid. In the example, the mixed liquid is of water base and the dispersion media is of oil base. The dispersion media is, for example, an oil.

Step S4 is an emulsion PCR step in which the nucleic acid (DNA) in the liquid particles formed in the emulsion forming step is amplified. In Step S4, the thermal cycler controls the temperature to cause the DNA to bond to the primers on the magnetic particles and amplify in the liquid particles in the emulsion (emulsion PCR, see (C) in FIG. 32). The target DNA molecule is amplified in each liquid particle. Namely, the nucleic acid is amplified in each liquid particle. The amplified nucleic acid bonds to the carrier via the primer in the liquid particle.

Step S5 is an emulsion breaking step in which the liquid particles containing the carriers (magnetic particles) carrying the nucleic acid (DNA) amplified in the emulsion PCR step are broken. After amplifying the DNA on the magnetic particles in step S4, the emulsion is broken and the magnetic particles including the amplified DNA are taken out of the liquid particles in step S5 (emulsion breaking). A single or a plurality of types of emulsion breaking reagent including alcohol or surfactant is used to break the emulsion.

Step S6 is a cleaning step of gathering the carriers (magnetic particles) taken out of the liquid particles broken in the emulsion breaking step. In step S6, the magnetic particles taken out of the liquid particles are cleaned in a Bound/Free-separation (B/F-separation) step (primary cleaning). In the B/F-separation step, the magnetic particles including the amplified DNA are magnetically gathered and moved in the cleaning liquid, thereby cleaning unnecessary substances off the magnetic particles. In the primary cleaning step, for example, a cleaning liquid including alcohol is used. Alcohol removes the oil film from the magnetic particles and converts an amplified double-stranded DNA to a single-stranded DNA.

Step S7 is a hybridization step in which the amplified product on the carriers (magnetic particles) gathered in the cleaning step reacts with the labeled matter. After the cleaning, the DNA converted to the single stranded DNA on the magnetic particle is hybridized with the labeled matter for detection (hybridization) in step S7 (see (D) in FIG. 32). The labeled matter includes, for example, a fluorescent substance. The labeled matter is designed to specifically bond to the DNA to be detected.

In step S8, the magnetic particles bonded to the labeled matter are cleaned in the B/F-separation step (secondary cleaning). The secondary B/F-separation step is performed in a manner similar to the primary B/F-separation. For example, phosphate buffered saline (PBS) is used as the cleaning liquid in the secondary cleaning step. PBS removes the unreacted labeled matter, which failed to bond to the DNA (including the labeled matter non-specifically bonded to the magnetic particle).

In step S9, the DNA is detected via the hybridized labeled matter. The DNA is detected by, for example, a flow cytometer. In the flow cytometer, the magnetic particles including the DNA bonded to the labeled matter flow through a flow cell where a laser beam is radiated to the magnetic particles. Fluorescence of the labeled matter caused by the laser beam is detected.

The DNA may be detected by image processing. For example, the magnetic particles including the DNA bonded to the labeled matter are dispersed on a slide plate. An image of the dispersed magnetic particles is captured by a camera unit. The number of the magnetic particles emitting fluorescence is counted based on the captured image.

[Example Processing of Specimen]

An example assay of processing a specimen using various types of the specimen processing chips 100 will now be described. In the following description, the controller 530 of the specimen processing apparatus 500 in which the specimen processing chip 100 is set controls the introducer 520 to control transfer of fluids, such as a specimen, reagents, the process liquid 21, and the fluid 24 to the specimen processing chip 100 and to control the flow in the specimen processing chip 100.

(Emulsion PCR Assay)

Figure 33:
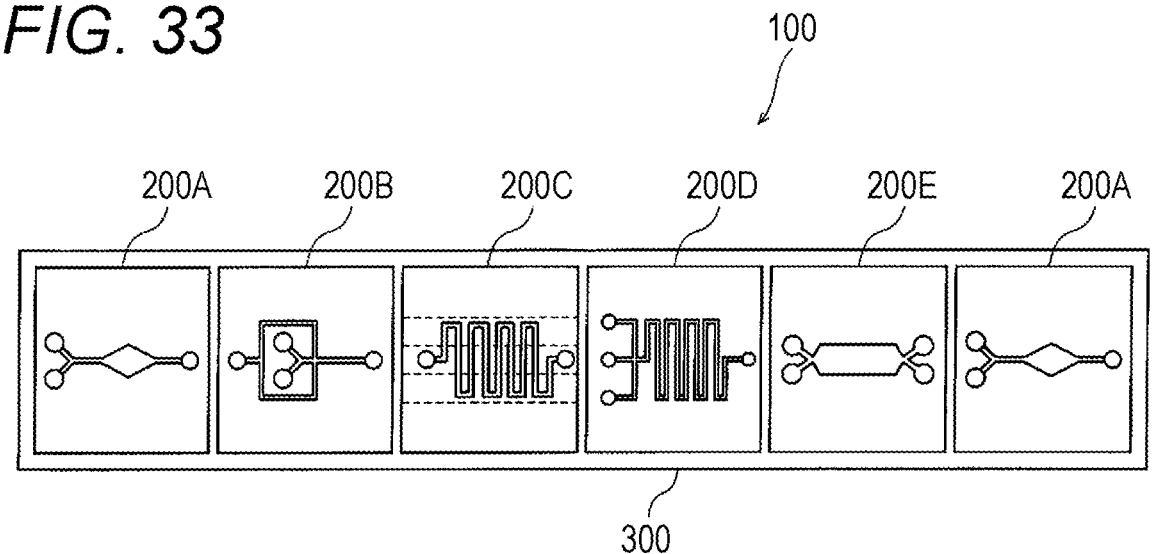
FIG. 33 illustrates an example specimen processing chip used for emulsion PCR assay.

FIG. 33 illustrates an example specimen processing chip 100 used for emulsion PCR assay.

The specimen processing chip 100 in FIG. 33 is composed of a combination of several types of fluid modules (200A to 200E) having different functions. Specifically, Pre-PCR is performed on the target component 20 in the fluid module 200A. Liquid particle forming is performed as the processing of the target component 20 in the fluid module 200B. Emulsion PCR is performed as the processing of the target component 20 in the fluid module 200C. Liquid particle breaking is performed as the processing of the target component 20 in the fluid module 200D. Cleaning (primary cleaning) is performed as the processing of the target component 20 in the fluid module 200E. Hybridization and cleaning (secondary cleaning) are performed as the processing of the target component 20 in the fluid module 200A. Liquids such as DNA, which is the target component, and the reagents flow through each fluid module in the specimen processing chip 100 and the emulsion PCR assay is performed. The fluid modules 200A to 200E may be integrated into a single fluid module 200 provided with flow-paths 201 where the processing is performed.

<Pre-PCR>

Figure 34:
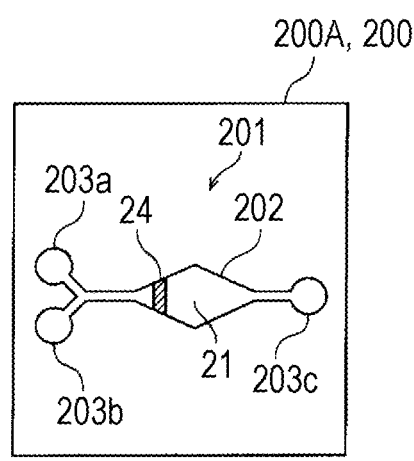
FIG. 34 illustrates an example fluid module used for Pre-PCR.

FIG. 34 illustrates an example fluid module 200A used for Pre-PCR. The flow-path 201 of the fluid module 200A includes a channel 202, joints 203a and 203b from which the reagent and the specimen are introduced, and a joint 203c from which the liquid is discharged. The channel 202 has a rhombic shape, for example, to control the flow velocity of the liquid.

The fluid module 200A is made of a high thermal resistance material, such as polycarbonate. The channel 202 has a height of, for example, 50 µm to 500 µm.

For example, the DNA extracted in the pre-processing is introduced from the joint 203a and a PCR amplification reagent is introduced from the joint 203b. While the mixed liquid of DNA and the reagent flows through the channel 202, the temperature of the mixed liquid is controlled by the heater 541. By controlling the temperature, the DNA reacts with the reagent and is amplified. The liquid containing the amplified DNA is transferred to the adjacent fluid module 200 via the joint 203c.

<Emulsion Forming>

Figure 35:
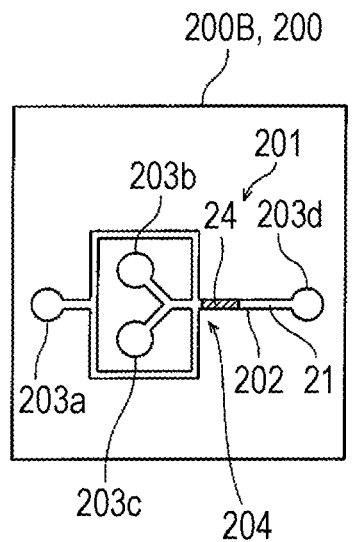
FIG. 35 illustrates an example fluid module used for forming emulsion.

FIG. 35 illustrates an example fluid module 200B used for forming emulsion. The flow-path 201 of the fluid module 200B includes a channel 202, joints 203a, 203b, and 203c from which the specimen and the reagent are introduced, and a joint 203d from which the liquid is discharged. The channel 202 has an intersection 204 where at least two channels intersect. The width of each channel at the intersection 204 is about tens of micrometers. In the embodiment, the channel has a width of 20 µm. The fluid module 200B may be provided with only either of the joints 203b or 203c.

For example, the channel 202 of the fluid module 200B has a height of 10 µm to 20 µm. To improve wettability against oil, the wall of the channel 202 is treated, for example, with hydrophobic material or fluorine. The material of the fluid module 200B is, for example, polydimethylsiloxane (PDMS) or polymethylmethacrylate (PMMA).

For example, a liquid containing the DNA amplified by Pre-PCR is introduced from the joint 203b, and a liquid containing magnetic particles and a reagent for PCR amplification is introduced from the joint 203c. The liquids introduced from the joints 203b and 203c are mixed in the channel 202 and then flow to the intersection 204. The diameter of the magnetic particles are selected, for example, so as the average particle diameter to be within a range from 0.5 µm to 3 µm. The average particle diameter is the average of particle diameters measured by the light scattering method. The pump 521 provides pressure P (1000 mbar≤P≤10000 mbar) to send the liquids to the joints 203b and 203c so as the flow-rate of the liquids introduced from the joints 203b and 203c to be constant.

For example, an oil for forming emulsion is introduced from the joint 203a. The introduced oil is branched from the channel 202 into a plurality of lines. The oil flows into the intersection 204 from a plurality of branched lines. The pump 521 provides pressure P (1000 mbar≤P≤10000 mbar) to send the oil to the joint 203a so as the flow-rate of the liquid introduced from the joint 203a to be constant.

Figure 36:
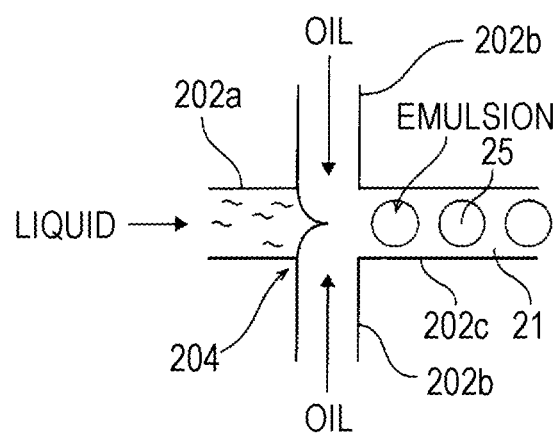
FIG. 36 is an enlarged view illustrating a first example intersection where emulsion is formed.

FIG. 36 illustrates an example of emulsion forming at the intersection 204. The mixed liquid of DNA and the reagent flows into the intersection 204 where the oil flows in along the vertical direction in FIG. 36. The oil intrudes into the mixed liquid from both sides at the intersection 204, creating a shear force. The mixed liquid is thereby separated into liquid particles. The oil that has flown into the intersection 204 covers each separated liquid particle, and emulsion is formed. The sample flow transformed into emulsion is transferred to the adjacent fluid module 200 via the joint 203d.

For example, the mixed liquid of DNA and the reagent flows into the intersection 204 by a constant flow-rate selected from a range from 0.4 µL/min to 7 µL/min. The oil flows into the intersection 204 by a constant flow-rate selected from a range from 1 µL/min to 50 µL/min. The flow-rate is controlled by the pressure provided by the pump 521. For example, the mixed liquid of DNA and the reagent and the oil flow into the intersection 204 by respective flow-rates of 2 µL/min (about 5200 mbar) and 14 µL/min (about 8200 mbar) to form about 10 million liquid particles 25 per minute. The liquid particles 25 are formed, for example, by about 600 thousand per minute to about 18 million per minute (about 10 thousand per second to about 300 thousand per second).

Figure 37:
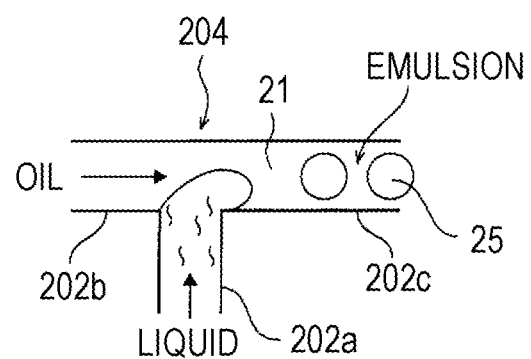
FIG. 37 is an enlarged view illustrating a second example intersection where emulsion is formed.

In the example in FIG. 36, total four channels 202 intersect to constitute the intersection 204 in a crisscross shape. The four channels 202 are a channel 202a in which the mixed liquid flows, two channels 202b in which the oil flows, and a channel 202c in which the emulsion flows. As illustrated in FIG. 37, the intersection 204 may be formed in a T-shape by three intersecting channels 202.

As a result of the liquid particle forming performed as the processing of the target component 20 in the fluid module 200B, the liquid particles 25 as the particles 22 are dispersed in the process liquid 21, which is an oil, in the channel 202. After forming the liquid particles 25, air is introduced as the fluid 24 from one of the joints 203a, 203b, and 203c. The fluid 24 forms the interface 23 that divides the fluid 24 from the oil in the channel 202. The fluid 24 is introduced at a predetermined flow-rate for a predetermined time period. The process liquid 21 is then supplied to move the interface 23 in the channel 202 toward the joint 203d. As a result, the liquid particles 25 retained in the channel 202 are moved together with the interface 23 and are discharged from the joint 203d.

In this manner, the processing of the target component 20 in the fluid module 200B includes forming the liquid particles 25 in the process liquid 21 in the flow-path 201, which liquid particles 25 include the mixed liquid of nucleic acid, the reagent for amplification reaction of nucleic acid, and the carriers 26 that bond to nucleic acid. After forming the liquid particles 25, the interface 23 of the fluid 24 is moved to move the liquid particles 25 in the flow-path 201. When the liquid particles 25 are formed in the process liquid 21 in the flow-path 201, the liquid particles 25 may adhere to the inner wall 11 and be retained. By moving the liquid particles 25 formed in the process liquid 21 by the interface 23 of the fluid 24, remaining of the liquid particles 25 can effectively be avoided.

<PCR>

Figure 38:
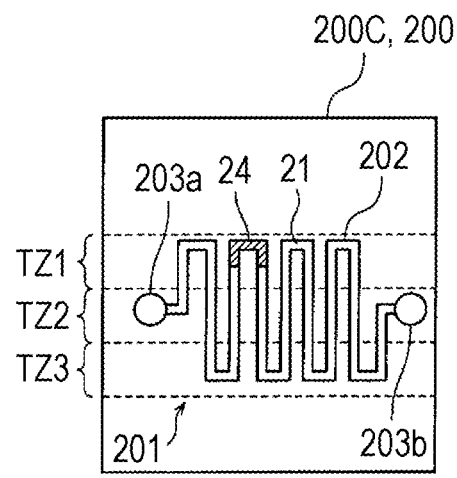
FIG. 38 illustrates an example fluid module used for emulsion PCR.

FIG. 38 illustrates an example fluid module 200C used for emulsion PCR.

The flow-path 201 of the fluid module 200C includes a channel 202, a joint 203a from which the liquid is introduced, and a joint 203b from which the liquid is discharged.

The fluid module 200C is made of a high thermal resistance material, such as polycarbonate. The channel 202 has a height of, for example, 50 μm to 500 μm.

The channel 202 runs a plurality of times through temperature zones TZ1 to TZ3 which are created by the heater 541. The number of the temperature zones TZ may be more than three or less than three. The number of times the channel 202 runs through the temperature zones TZ1 to TZ3 corresponds to the number of thermal cycles. As illustrated in a simplified manner in FIG. 38, the number of thermal cycles of emulsion PCR is, for example, about 40. The channel 202 has turnings or serpentine portions, which number corresponds to the number of cycles.

As illustrated in FIG. 38, the DNA in each liquid particle 25 is amplified as they flow through the channel 202.

While the emulsion PCR is performed as the processing of the target component 20 in the fluid module 200C, the liquid particles 25 as the particles 22 are kept dispersed in the process liquid 21, which is an oil, in the channel 202. During or after the emulsion PCR, air is introduced from the joint 203a as the fluid 24. The fluid 24 forms the interface 23 that divides the fluid 24 from the oil in the channel 202. The fluid 24 is introduced, for example, at a predetermined flow-rate for a predetermined time period. The process liquid 21 is then supplied to move the interface 23 in the channel 202 toward the joint 203b. As a result, the liquid particles 25 retained in the channel 202 are moved together with the interface 23 and are discharged from the joint 203b. The liquid particles 25 including the amplified DNA are transferred to the adjacent fluid module 200D via the joint 203b.

As described above, the processing of the target component 20 in the fluid module 200C includes amplifying the nucleic acid included in the liquid particles 25 dispersed in the process liquid 21, the liquid particles 25 including the mixed liquid of nucleic acid, the reagent for amplification reaction of nucleic acid, and the carriers 26 that bond to nucleic acid. During or after amplifying the nucleic acid, the interface 23 of the fluid 24 is moved to move the liquid particles 25 including the carriers 26 bonded to the nucleic acid amplified by nucleic acid amplification. To perform the thermal cycle processing in the flow-path 201, the liquid particles 25 are conveyed through a plurality of temperature zones TZ, namely, through a long conveyed distance. This may cause failure of conveying some liquid particles 25 retained in the course of conveyance. By moving the liquid particles 25 by the interface 23 of the fluid 24, remaining of the liquid particles 25 can effectively be avoided.

<Emulsion Breaking>

Figure 39:
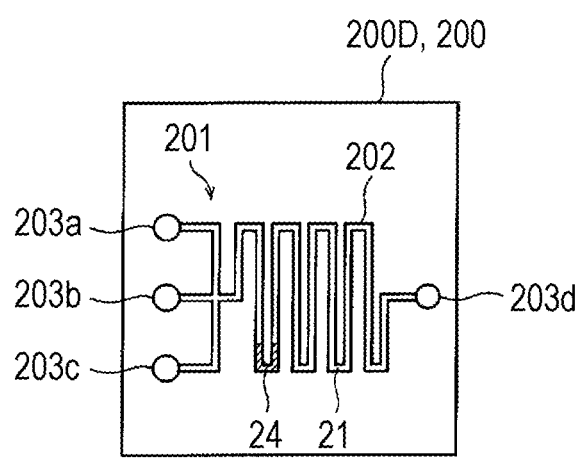
FIG. 39 illustrates an example fluid module used for breaking emulsion.

FIG. 39 illustrates an example fluid module 200D used for breaking emulsion. The flow-path 201 of the fluid module 200D includes a channel 202, joints 203a, 203b, and 203c from which the emulsion or the reagent for breaking emulsion flows in, and a joint 203d from which the liquid is discharged.

The fluid module 200A is made of a high chemical resistance material, such as polycarbonate and polystyrene. The channel 202 has a height of, for example, 50 μm to 500 μm.

For example, the emulsion that has gone under the emulsion PCR step flows in from the joint 203b, and the reagent for breaking emulsion flows in from the joints 203a and 203c. The emulsion and the reagent for breaking emulsion are mixed while flowing through the channel 202, and the liquid particles 25 in the emulsion are broken. In the processing of the target component 20, the liquid particles 25 including the carriers 26 bonded to amplified nucleic acid are mixed with the reagent for breaking the liquid particles 25, and thereby the liquid particles 25 are broken. The liquid particles 25 can easily be broken by simply mixing the liquid particles 25 with the reagent for breaking the liquid particles 25. The channel 202 has a form that promotes mixing of the liquids. For example, the channel 202 lets the liquid to flow a plurality of times from one side to the other side in the width direction of the specimen processing chip 100. The magnetic particles taken out of the liquid particles 25 are transferred to the adjacent fluid module 200 via the joint 203d.

As a result of the liquid particle breaking performed as the processing of the target component 20 in the fluid module 200D, the particles 22 and the magnetic particles 26a as the carriers 26 are dispersed in the process liquid 21 in the channel 202. The magnetic particles 26a taken out of the broken liquid particles 25 are bonded to amplified nucleic acid. The process liquid 21 in the channel 202 is a mixed liquid including the oil, the reagent for breaking emulsion, and the liquid that has come out of the broken liquid particles 25 (the liquid that has been contained in the liquid particles 25 together with the reagent for PCR amplification and DNA).

After the liquid particle breaking, air is introduced as the fluid 24 from one of the joints 203a, 203b, and 203c. The fluid 24 forms the interface 23 that divides the fluid 24 from the process liquid 21 in the channel 202. The fluid 24 is introduced, for example, at a predetermined flow-rate for a predetermined time period. As the amount of the fluid 24 introduced into the channel 202 increases, the interface 23 moves toward the joint 203d in the channel 202. As a result, the magnetic particles 26a retained in the channel 202 are moved together with the interface 23 and are discharged from the joint 203d.

As described above, the processing of the target component 20 in the fluid module 200D is breaking the liquid particles 25 containing the carriers 26 bonded to the amplified nucleic acid. After breaking the liquid particles 25, the interface 23 of the fluid 24 is moved to move the carriers 26 taken out of the broken liquid particles 25. When breaking the water phase liquid particles 25 formed in the oil phase oil, the carriers 26 taken out of the broken liquid particles 25 contact the surrounding oil and easily aggregate or adhere. With the carriers 26 taken out of the broken liquid particles 25 moved by the interface 23 of the fluid 24, remaining of the carriers 26 can efficiently be avoided.

<Cleaning (Primary Cleaning)>

Figure 40:
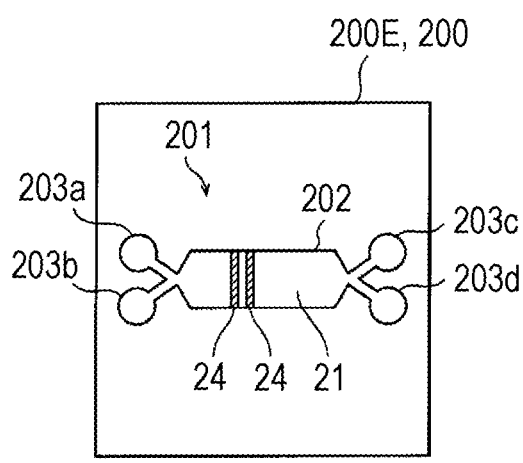
FIG. 40 illustrates an example fluid module used in a cleaning step (primary cleaning)

FIG. 40 illustrates an example fluid module 200E used in a cleaning step (primary cleaning). The flow-path 201 of the fluid module 200E includes joints 203a and 203b from which a liquid is introduced, joints 203c and 203d from which the liquid is discharged, and a channel 202. The channel 202 has a shape linearly extending in a certain direction, for example, an approximate rectangle. The channel 202 has a wide shape so that magnetic particles can be magnetically gathered and dispersed sufficiently. The joints 203a and 203b for liquid in-flow are disposed at one end of the channel 202, and the joints 203c and 203d for liquid out-flow are disposed at the other end of the channel 202.

The fluid module 200E is made of a high chemical resistance material, such as polycarbonate and polystyrene. The channel 202 has a height of, for example, 50 μm to 500 μm.

Figure 41:
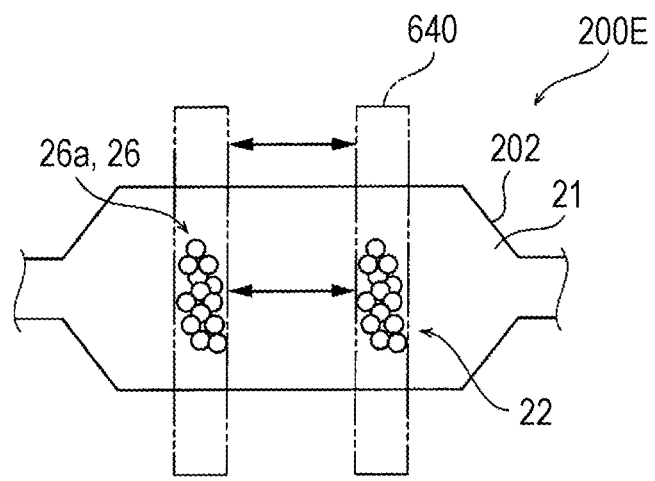
FIG. 41 illustrates an example operation of washing and condensing magnetic particles in the fluid module.

FIG. 41 illustrates an example operation of washing and condensing the magnetic particles in the fluid module 200E. The liquid including magnetic particles flows from the joint 203a toward the joint 203c. The magnetic particles in the liquid are magnetically condensed by a magnet 640. The magnet 640 can be moved back and forth along the longitudinal direction of the channel 202. The magnetic particles move back and forth in the channel 202 along with the magnet 640. The back and forth motion causes the magnetic particles to aggregate.

A cleaning liquid is supplied from the joint 203b. The cleaning liquid continuously flows from the joint 203b to the joint 203d. The joint 203d serves as a drain for discharging the cleaning liquid.

For example, the magnetic particles 26a magnetically caught in the flow of the cleaning liquid are moved back and forth along the flow-path 201 to be cleaned. The cleaning is performed by moving the magnetic particles, along with the magnet 640, in the channel 202 back and forth under the flow of the cleaning liquid. By moving the magnetically gathered magnetic particles 26a along the flow-path 201, the gathered magnetic particles 26a efficiently contact the cleaning liquid. This improves cleaning efficiency. Meanwhile, moving the magnetic particles 26a that are magnetically forced against the inner wall 11 of the flow-path 201 causes the magnetic particles 26a to further strongly adhere to the inner wall 11. Nevertheless, moving the released magnetic particles 26a by moving the interface 23 of the fluid 24 effectively avoids remaining of the magnetic particles 26a, which easily adhere to the inner wall 11.

In the primary cleaning step, a cleaning liquid including alcohol is used. The primary cleaning using the cleaning liquid removes the oil film from the magnetic particles and converts the amplified double-stranded DNA to the single-stranded DNA.

As a result of the primary cleaning performed in the fluid module 200E as the processing of the target component 20, the particles 22 and the magnetic particles 26a as the carriers 26 are dispersed in the process liquid 21 in the channel 202. After the cleaning, the magnetic particles 26a are released from the magnetic force but aggregate at the final magnetically gathered location in the channel 202. The process liquid 21 in the channel 202 is a cleaning liquid. After the primary cleaning, air is introduced as the fluid 24 from the joint 203a or 203b. The fluid 24 forms the interface 23 that divides the fluid 24 from the process liquid 21 in the channel 202. The fluid 24 is introduced, for example, at a predetermined flow-rate for a predetermined time period. The process liquid 21 is then supplied to move the interface 23 in the channel 202 toward the joint 203d. As a result, the magnetic particles 26a retained in the channel 202 are moved together with the interface 23 and are discharged from the joint 203d. The cleaned and condensed magnetic particles 26a are discharged from the joint 203b and conveyed to the adjacent fluid module 200A.

<Hybridization>

The magnetic particles are mixed with the reagent including the labeled matter in a fluid module 200A having a configuration similar to that illustrated in FIG. 34. The mixture is subjected to a thermal cycle. For example, the liquid containing the magnetic particles is transferred from the joint 203a, and the reagent including the labeled matter is introduced from the joint 203b. The thermal cycle causes the DNA on the magnetic particles to bond to the labeled matter.

<Cleaning (Secondary Cleaning)>

The secondary cleaning step, performed after hybridization (bounding) with the labeled matter, may be performed in the fluid module 200A. For example, in FIG. 34, the cleaning liquid is introduced from the joint 203b into the channel 202 in which the magnetic particles are magnetically gathered by the magnet 640 (see FIG. 41). PBS is used as a cleaning liquid in the secondary cleaning step. In the secondary cleaning using the cleaning liquid, the unreacted labeled matter which has failed to bond to DNA (including the labeled matter non-specifically bonded to the magnetic particle) is removed. After the secondary cleaning, the magnetic particles including the labeled matter are discharged from the joint 203c. Similarly to the fluid module 200E (see FIG. 40), the joint 203 for draining is preferably provided on the discharge side of the fluid module 200A.

As a result of the hybridization and the secondary cleaning performed in the fluid module 200A as the processing of the target component 20, the particles 22 and the magnetic particles 26a as the carriers 26 are dispersed in the process liquid 21 in the channel 202. After the cleaning, the magnetic particles 26a are released from the magnetic force but aggregate at the final magnetically gathered location in the channel 202. The process liquid 21 in the channel 202 is a cleaning liquid. After the secondary cleaning, air is introduced as the fluid 24 from the joint 203a or 203b. The fluid 24 forms the interface 23 that divides the fluid 24 from the process liquid 21 in the channel 202. The fluid 24 is introduced, for example, at a predetermined flow-rate for a predetermined time period. The process liquid 21 is then supplied to move the interface 23 in the channel 202 toward the joint 203d. As a result, the magnetic particles 26a retained in the channel 202 are moved together with the interface 23 and are discharged from the joint 203c.

The interface 23 of the fluid 24 sends the magnetic particles 26a out of the specimen processing chip 100 from the joint 203c. The magnetic particles 26a are collected, for example, in a sample container (see FIG. 2). When the fluid 24 is a gas, such as air, the fluid 24 sent out of the specimen processing chip 100 dissipates into the atmospheric air. The amount of the sample liquid finally sent out of the specimen processing chip 100 is approximately identical to the amount of the cleaning liquid in which the magnetic particles 26a have been dispersed in the channel 202 before introducing the fluid 24. This is the minimum necessary amount of the sample liquid to achieve a high collection rate of the magnetic particles 26a.

When the fluid 24 is a liquid, the fluid 24 is sent out of the specimen processing chip 100 to be collected together with the magnetic particles 26a. The amount of the collected sample therefore increases by the amount of the fluid 24. The increased amount of the fluid 24 dilutes the concentration of the magnetic particles 26a in the collected sample. For example, when the concentration of the magnetic particles 26a in the sample is below the concentration range suitable for detection, condensation processing of the magnetic particles 26a is performed. In the condensation processing, for example, the magnetic particles 26a are magnetically gathered in the sample container and then the supernatant liquid component is removed while the magnetic particles 26a are magnetically caught. When the carriers 26 other than the magnetic particles 26a are used, the liquid component is removed after separating the carriers 26 from the liquid component by, for example, centrifugation. Dilution of the collected sample may increase the processing procedures and the processing time. Thus, the fluid 24 is preferably a gas, for example, air.

As described above, the processing of the target component 20 in the fluid module 200A includes magnetically catching the magnetic particles 26a in the flow-path 201, introducing the cleaning liquid into the flow-path 201 in which the magnetic particles 26a are caught, and releasing the magnetic particles 26a. The magnetic particles 26a magnetically gathered and caught are more likely to be retained in the flow-path 201 because the magnetic particles 26a are surficially covered with the amplified nucleic acid which promotes aggregation and adherence of the magnetic particles 26a. After cleaning the magnetic particles 26a with the cleaning liquid, the fluid 24 is introduced into the flow-path 201 to move the released magnetic particles 26a by the interface 23 of the fluid 24. Remaining of the magnetic particles 26a, which are easily retained, can effectively be avoided.

More specifically, the processing of the target component 20 in the fluid module 200A includes magnetically catching the magnetic particles 26a in the flow-path 201, introducing the labeled matter for detecting the amplified nucleic acid into the flow-path 201 to cause reaction with the amplified nucleic acid and thereby form the magnetic particles 26a including the labeled matter, and introducing the cleaning liquid into the flow-path 201 in which the magnetic particles 26a including the labeled matter are caught to clean the magnetic particles 26a. In this case, the magnetic particles 26a magnetically gathered and caught are more easily retained in the flow-path 201 because the magnetic particles 26a are surficially bonded to the amplified nucleic acid and the labeled matter and therefore aggregate and adhere easily. After cleaning the magnetic particles 26a with the cleaning liquid, the fluid 24 is introduced into the flow-path 201 to move the released magnetic particles 26a by the interface 23 of the fluid 24. Remaining of the magnetic particles 26a, which are easily retained, can effectively be avoided.

The fluid module 200E for performing the secondary cleaning may be added in the downstream of the fluid module 200A that performs hybridization. In such a configuration, the fluid 24 is introduced into the fluid module 200E after the secondary cleaning as the processing of the target component 20 so that the interface 23 sends the magnetic particles 26a out of the specimen processing chip 100 and the magnetic particles 26a are collected.

<Exemplary Modification of Primary Cleaning, Hybridization and Secondary Cleaning>

In another example configuration, primary cleaning, hybridization, and secondary cleaning may be performed in a single fluid module 200E (see FIG. 40). In this case, a sample in which emulsion has been broken is introduced from the joint 203a into the channel 202 and magnetic gathering is performed by the magnet 640. A cleaning liquid including alcohol for primary cleaning, a labeling reagent for hybridization, and a cleaning liquid (PBS) for secondary cleaning are introduced in this order from the joint 203b to perform each processing step. In this case, it is not necessary to provide the fluid module 200A in the downstream of the fluid module 200E. In such a case, the fluid 24 is introduced into the fluid module 200E after performing the primary cleaning, hybridization, and the secondary cleaning as the processing of the target component 20. The interface 23 sends the magnetic particles 26a out of the specimen processing chip 100 and the magnetic particles 26a are collected.

<Detection>

After being subjected to the secondary cleaning, the magnetic particles 26a including the labeled matter are detected by, for example, a flow cytometer 40 (see FIG. 2) or imaging analysis. To be detected by the flow cytometer 40 (see FIG. 2), for example, the magnetic particles including the labeled matter are transferred to the separately provided flow cytometer 40 after being recovered from the specimen processing apparatus 500. The magnetic particles including the labeled matter are detected by the detector 544 of the specimen processing apparatus 500 by fluorescence of the label. An image of the magnetic particles including the labeled matter is captured by the camera unit 545 of the specimen processing apparatus 500. The captured image is analyzed by the specimen processing apparatus 500 or a computer connected to the specimen processing apparatus 500.

(Single Cell Analysis)

Figure 42:
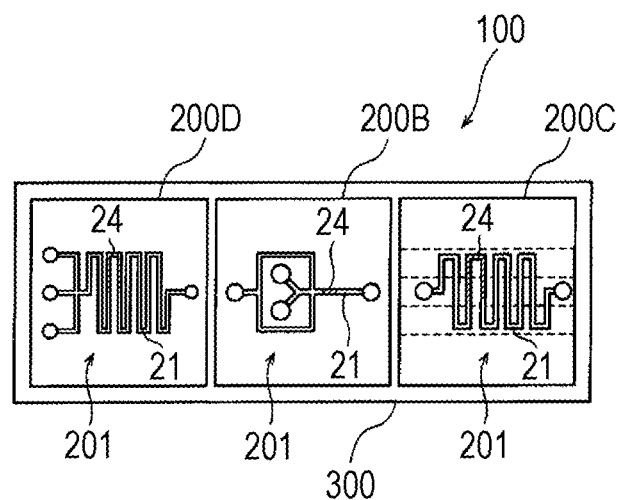
FIG. 42 illustrates an example specimen processing chip used for single cell analysis.

An example of single cell analysis using the specimen processing chip 100 will now be described. The analysis is performed for each cell included in a sample such as blood. FIG. 42 illustrates an example specimen processing chip 100 used for the single cell analysis.

For example, the specimen processing chip 100 is configured as a combination of a fluid module 200D for mixing liquids, a fluid module 200B for forming emulsion, and a fluid module 200C for PCR amplification.

The single cell analysis includes a step of mixing cells as the target component with a reagent for amplification reaction of nucleic acid (first step), a step of forming liquid particles in a dispersion media, the liquid particles including a mixed liquid of the liquid formed in the first step and a cytolysis reagent (second step), and a step of amplifying nucleic acid, which has come out of the disintegrated cells in the second step, in the liquid particles.

The configuration of the fluid module 200D (for example, material and channel height) is similar to that in FIG. 39. Thus, detailed description is omitted. A specimen, such as blood, is introduced from a joint 203b of the fluid module 200D, and a PCR amplification reagent is introduced from joints 203a and 203c. The cells included in the specimen and the PCR amplification reagent are mixed while flowing through the channel 202.

As a result of the mixing of the liquids performed as the processing of the target component 20 in the fluid module 200D, the cells as the particles 22 are dispersed in the process liquid 21 in the channel 202. The process liquid 21 in the channel 202 is a mixed liquid of the liquid component in the specimen and the PCR amplification reagent. After the mixing of the liquids, air is introduced as the fluid 24 from one of the joints 203a, 203b, and 203c. The fluid 24 forms the interface 23 that divides the fluid 24 from the process liquid 21 in the channel 202. The fluid 24 is introduced, for example, at a predetermined flow-rate for a predetermined time period. The process liquid 21 is then supplied to move the interface 23 in the channel 202 toward the joint 203d. As a result, the cells retained in the channel 202 are moved together with the interface 23 and are discharged from the joint 203c. The mixed liquid is transferred to the adjacent fluid module 200B via the joint 203c.

The configuration of the fluid module 200B (for example, material and channel height) is similar to that in FIG. 35. Thus, detailed description is omitted. The mixed liquid of the cells, the PCR amplification reagent, and a fluorescent pigment is introduced from the joint 203b of the fluid module 200B. The cytolysis reagent is introduced from the joint 203c. An oil for forming emulsion is introduced from the joint 203a. The mixed liquid of the cells, the PCR amplification reagent, and the cytolysis reagent is formed into the liquid particles 25 each covered with the oil at the intersection 204 to form the emulsion. The liquid particles 25 containing the mixed liquid are transferred to the adjacent fluid module 200C via the joint 203c. While the emulsion is transferred to the fluid module 200C, the cells in the liquid particles 25 are disintegrated by the cytolysis reagent. Disintegration of the cells let the DNA to come out of the cells into the liquid particles 25 including the PCR amplification reagent.

As a result of the liquid particle forming performed as the processing of the target component 20 in the fluid module 200B, the liquid particles 25 as the particles 22 are dispersed in the process liquid 21 in the channel 202. After disintegration of the cells, the liquid particles 25 including the mixed liquid of the cells, the PCR amplification reagent, and the cytolysis reagent also includes the target component 20 and the DNA, or nucleic acid. The process liquid 21 in the channel 202 is an oil. After the liquid particle forming, air is introduced as the fluid 24 from one of the joints 203a, 203b, and 203c. The fluid 24 forms the interface 23 that divides the fluid 24 from the process liquid 21 in the channel 202. The fluid 24 is introduced, for example, at a predetermined flow-rate for a predetermined time period. The process liquid 21 is then supplied to move the interface 23 in the channel 202 toward the joint 203d. As a result, the liquid particles 25 retained in the channel 202 are moved together with the interface 23 and are discharged from the joint 203c. The mixed liquid is transferred to the adjacent fluid module 200C via the joint 203c.

As described above, the processing of the target component 20 in the fluid module 200B is forming of the liquid particles 25 in the process liquid 21 in the flow-path 201, which liquid particles 25 include the mixed liquid of the cells, the reagent for disintegrating the cells, and the carriers 26 that bond to nucleic acid. During or after the forming the liquid particles 25, the interface 23 of the fluid 24 is moved to move the liquid particles 25 including the cells and the carriers 26 bonded to nucleic acid. When the liquid particles 25 are formed in the process liquid 21 in the flow-path 201, the liquid particles 25 may adhere to the inner wall 11 and be retained. By moving the liquid particles 25 formed in the process liquid 21 by the interface 23 of the fluid 24, remaining of the liquid particles 25 can effectively be avoided.

Figure 46:
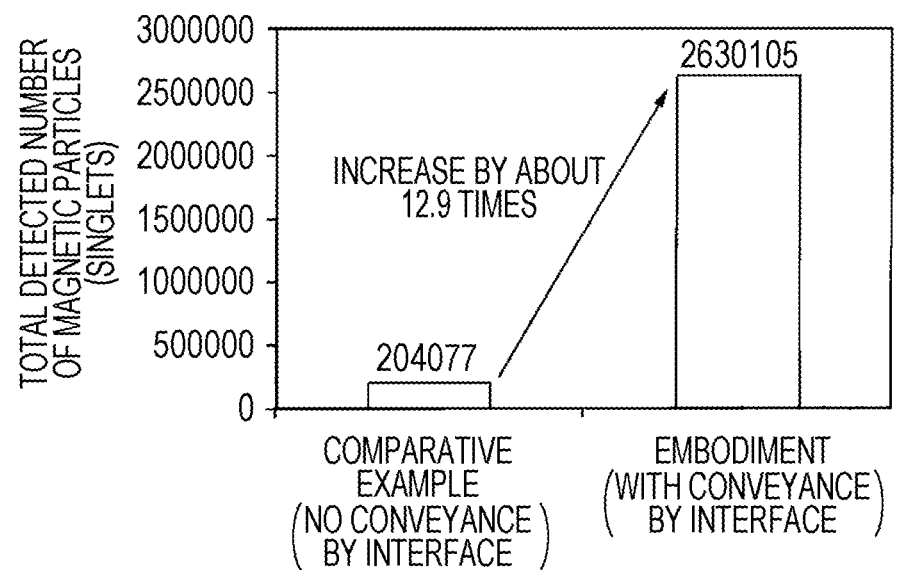
FIG. 46 illustrates an experimental result of detecting the number of magnetic particles.
Figure 47:
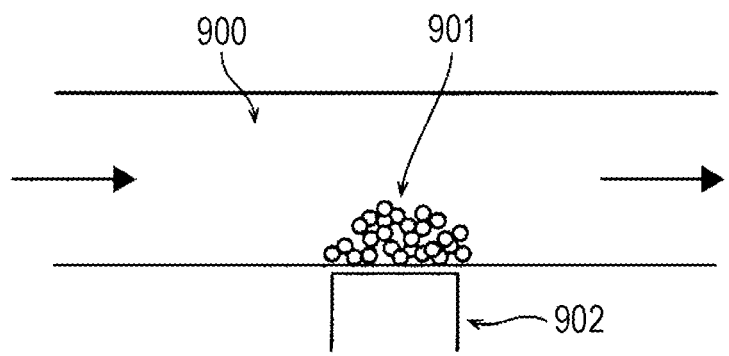
FIG. 47 illustrates transfer of particles in a flow-path of prior art.

The configuration of the fluid module 200C (for example, material and channel height) is similar to that in FIG. 46. Thus, detailed description is omitted. The emulsion transferred to the fluid module 200C is subjected to a thermal cycle while flowing through the channel 202 of the fluid module 200C. The DNA taken out of the disintegrated cells in the liquid particles 25 is amplified by the thermal cycle. Protein taken out of the disintegrated cells in the liquid particles 25 may be detected by transformation of protein into enzyme and reaction between the enzyme and the substrate.

While the PCR is performed as the processing of the target component 20 in the fluid module 200C, the liquid particles 25 as the particles 22 are kept dispersed in the process liquid 21 in the channel 202. The liquid particles 25 are a mixed liquid of the PCR amplification reagent and the cytolysis reagent and includes the target component 20 and the DNA, or nucleic acid. The process liquid 21 in the channel 202 is an oil. During or after the PCR, air is introduced as the fluid 24 from the joint 203a. The fluid 24 forms the interface 23 that divides the fluid 24 from the process liquid 21 in the channel 202. The fluid 24 is introduced, for example, at a predetermined flow-rate for a predetermined time period. As the amount of the fluid 24 introduced into the channel 202 increases, the interface 23 further moves toward the joint 203b in the channel 202. As a result, the liquid particles 25 retained in the channel 202 are moved together with the interface 23 and are discharged from the joint 203c.

The fluid module 200D illustrated in FIG. 39 may be provided in the downstream of the fluid module 200C to perform breaking of the liquid particles 25. In this case, the processing of the target component 20 in the fluid module 200D is breaking the liquid particles 25 in the process liquid 21 in the flow-path 201, the liquid particles 25 including the carriers 26 bonded to the nucleic acid taken out of the disintegrated cells in the mixed liquid of the cells, the reagent for disintegrating the cells, and the carriers 26 to be bonded to nucleic acid. After breaking the liquid particles 25, the interface 23 of the fluid 24 is moved to move the carriers 26 bonded to the nucleic acid taken out of the disintegrated cells. By moving the carriers 26 taken out of the broken liquid particles 25 by the interface 23 of the fluid 24, remaining of the carriers 26 can efficiently be avoided.

(Immunoassay <Digital ELISA>)

Figure 43:
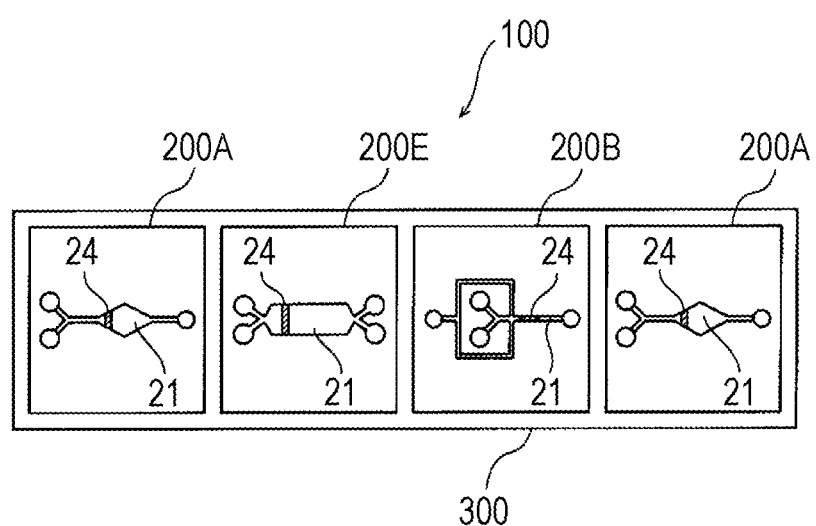
FIG. 43 illustrates an example specimen processing chip used for immunoassay.

An example of immunoassay using the specimen processing chip 100 described above will now be described. The target component of immunoassay is a protein such as an antigen and an antibody included in blood. FIG. 43 illustrates an example specimen processing chip 100 used in enzyme-linked immunosorbent assay (Digital ELISA).

The specimen processing chip 100 is configured as a combination of a fluid module 200A for temperature control, a fluid module 200BE for B/F-separation, a fluid module 200B for forming emulsion, and a fluid module 200A for temperature control.

Figure 44:
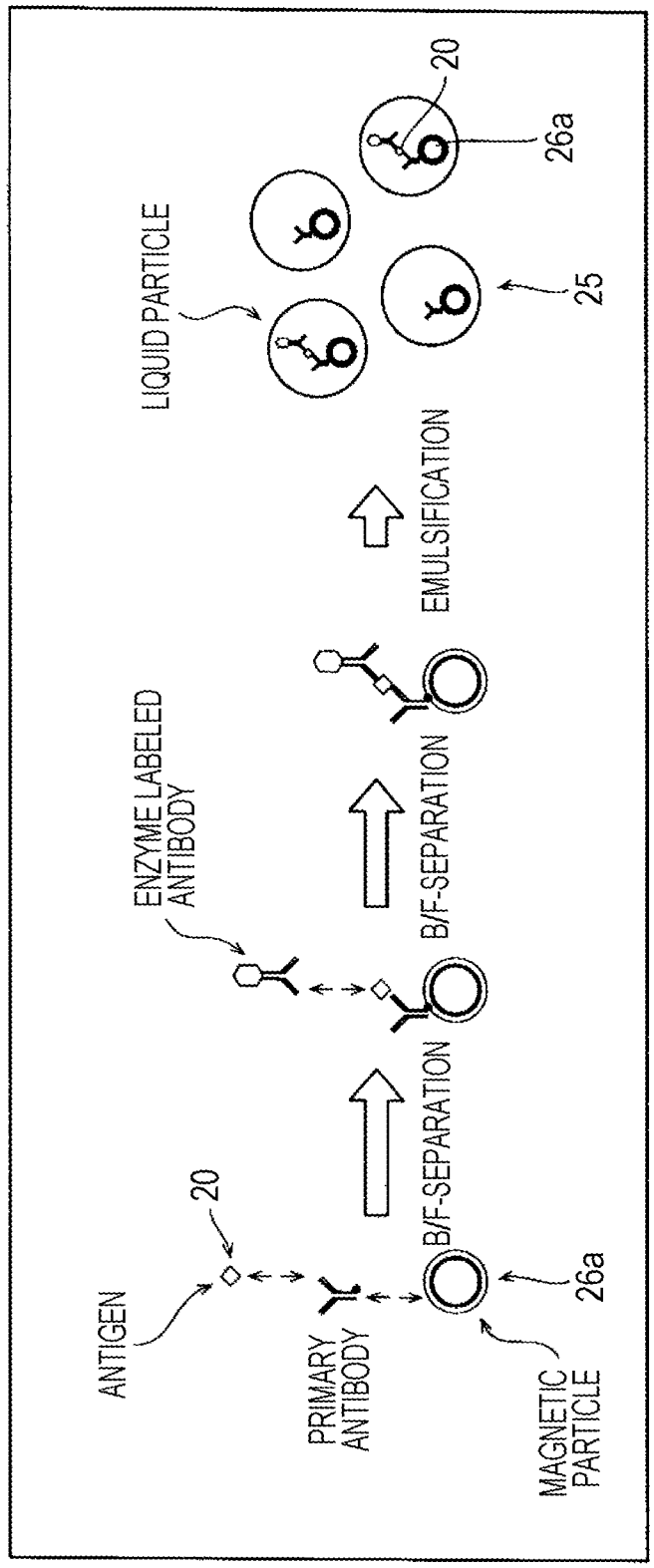
FIG. 44 illustrates reaction steps in immunoassay.

FIG. 44 schematically illustrates Digital ELISA. ELISA is a method in which an immune complex is formed by letting the magnetic particles carry the antigen (or the antibody) and the labeled matter, which are the target component, and the target component is detected based on the label in the immune complex. Digital ELISA is a method in which the sample diluted to the limit (diluted so as the number of the target component in each micro segment to be 1 or 0) is dispersed in micro segments, and the number of the micro segments that gives a positive signal based on the label is directly counted to measure the absolute concentration of the target component in the sample. In FIG. 44, each liquid particle 25 in the emulsion composes a micro segment. The specimen processing chip 100 performs the assay illustrated in the example in FIG. 44.

More specifically, Digital ELISA Assay includes a step of forming the immune complex composed of the target component (antigen or antibody) bonded to the carrier by antigen-antibody reaction (first step), a step of causing reaction between the immune complex formed in the first step and the labeled matter (second step), a step of forming the liquid particles in a dispersion media, the liquid particles including the immune complex bonded to the labeled matter as a result of the second step and a substrate for detecting the labeled matter (third step), and a step of causing the labeled matter in the liquid particles formed in the third step to react with the substrate (fourth step).

The configuration of the fluid module 200A (for example, material and channel height) is similar to that in FIG. 34. Thus, detailed description is omitted. The specimen including the antigen is introduced from the joint 203a into the fluid module 200A, and a reagent including a primary antibody and the magnetic particles is introduced from the joint 203b. The specimen and the reagent are mixed in the channel 202. The mixed liquid is subjected to temperature control in the channel 202 to form the immune complex including the antigen, the primary antibody, and the magnetic particles. The temperature is controlled at about 40° C. to 50° C., more preferably, about 42° C. The liquid containing the produced complex is transferred to the adjacent fluid module 200E via the joint 203c.

The configuration of the fluid module 200E (for example, material and channel height) is similar to that in FIG. 40. Thus, detailed description is omitted. In the channel 202 of the fluid module 200, the complex including the magnetic particles is magnetically gathered by the magnet 640 and cleaned (primary B/F-separation). After the primary B/F-separation, the magnetic force of the magnet 640 is removed to disperse the immune complex. The dispersed immune complex reacts with the enzyme labeled antibody. After the reaction, the immune complex is magnetically gathered again by the magnet 640 and cleaned (secondary B/F-separation). After the cleaning, the immune complex is transferred to the adjacent fluid module 200B.

The configuration of the fluid module 200B (for example, material and channel height) is similar to that in FIG. 35. Thus, detailed description is omitted. The complex is introduced from the joint 203b of the fluid module 200B, and the reagent including fluorescent/light-emitting substrate is introduced from the joint 203c. An oil for forming emulsion is introduced from the joint 203a. At the intersection 204, the liquid including the immune complex and the reagent including the fluorescent/light-emitting substrate are formed into the liquid particles 25 each covered by the oil at the intersection 204 to form the emulsion. The emulsion is transferred from the joint 203c to the adjacent fluid module 200A.

The emulsion transferred to the fluid module 200A is heated in the channel 202 and the substrate in each liquid particle 25 reacts with the immune complex to emit fluorescence. The detector 544 of the specimen processing apparatus 500 detects the fluorescence. This enables detection, by a unit of a single molecule, of the target component contained in each liquid particle 25.

In the fluid module 200A, the magnetic particles 26a as the particles 22 bond to the antigen or the antibody, which is the target component 20. The magnetic particles 26a are dispersed as the process liquid 21 in the mixed liquid of the specimen and the reagent. In the fluid module 200E, the magnetic particles 26a as the particles 22 are dispersed in the cleaning liquid, which is the process liquid 21. In the fluid module 200B, the liquid particles 25 as the particles 22 are dispersed in the oil, which is the process liquid 21. In the fluid module 200A, the liquid particles 25 as the particles 22 are dispersed in the oil, which is the process liquid 21.

In each of the fluid modules 200A, 200E, 200B, and 200A, air as the fluid 24 is introduced during or after the processing of the target component 20. The interface 23 formed by the fluid 24 moves in the channel 202 and thereby the particles 22 retained in the channel 202 move together with the interface 23 to be discharged. The magnetic particles 26a are conveyed effectively by the interface 23 of the fluid 24, because the step of magnetically catching and releasing the magnetic particles 26a are performed in the fluid module 200E.

(Result of Experiment)

An experiment performed to check the effect of the method of processing a specimen according to the embodiment will now be described. In the experiment, particles 22 in a flow-path 201 were conveyed by moving an interface 23 of a fluid 24, and a sample discharged from the flow-path 201 was collected. As a comparative example, a process liquid 21 was introduced into the flow-path 201 and samples discharged from the flow-path 201 were collected. Magnetic particles 26a bonded to a target component 20 included in each collected sample were detected. The number of detection was compared among the samples.

Figure 45:
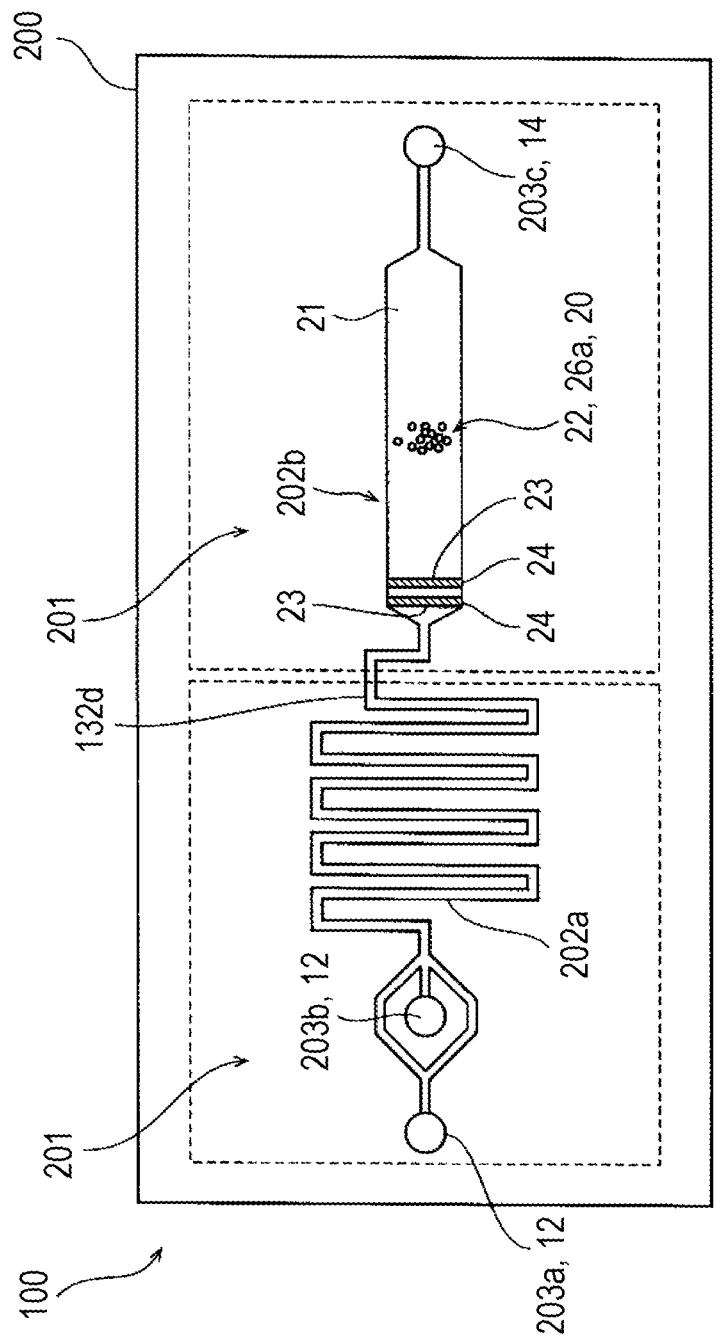
FIG. 45 illustrates a specimen processing chip used in an exemplary experiment.

FIG. 45 illustrates a flow-path used for the experiment. A flow-path 201 is composed of a flow-path 201 of a fluid module 200D for performing liquid particle breaking and a flow-path 201 of a fluid module 200E for performing cleaning, the two flow-paths 201 being connected to each other. Joints 203a and 203b (12) provided at one end of the flow-path 201 are connected to one end of a channel 202a in which the liquid particle breaking is performed. The other end of the channel 202a is connected to one end of a channel 202b in which cleaning is performed. Magnetic gathering and cleaning are performed in the channel 202b. The other end of the channel 202b is connected to a joint 203c (14) which serves as a discharge port.

The joint 203a serves as a common inlet port for introducing a reagent for breaking emulsion, a cleaning liquid for primary cleaning including alcohol, and PBS which is a cleaning liquid for secondary cleaning. Air was introduced as a fluid 24 from the joint 203a. The joint 203b is an inlet port for introducing emulsion in which the magnetic particles 26a as the particles 22 are dispersed in the oil. The joint 203c is a discharge port. The liquid flowing out during each processing was discarded but the liquid flowing out as the final sample was collected in a container.

In the experiment, the secondary cleaning, which is the processing immediately before the detection in the emulsion PCR assay described above, was performed to simulate a step of collecting a sample for FCM analysis. The particles 22 are the magnetic particles 26a bonded to the target component 20 and the labeled matter. The process liquid 21 is a cleaning liquid. In the secondary cleaning, the magnetic particles 26a were magnetically caught, cleaned, and then released.

<Embodiment>

An experimental method of the embodiment will now be described.

(1) Liquid particles 25 formed by using the reagent described below were prepared. Instead of using DNA, an alternative component was used, since the experiment was for checking the effect of the method.

BEAMing PCR Master Mix
Emulsion Beads (Magnetic Particles)
Taq-DNA Polymerase
EmulsiFIRE
1×, TE, pH 8.0 (Used as Alternative for DNA)
50 mM NaOH (2) The liquid particles 25 and BB1/1% BB2 were mixed in the channel 202a to break the liquid particles 25. The resulting mixture was transferred to the channel 202b and the magnetic particles 26a were magnetically caught. The liquid particles 25 and BB1 were supplied respectively at a pressure of 40 mbar and a pressure of 140 mbar. BB1 and BB2 are each a cleaning liquid including alcohol.

(3) The magnetic particles 26a in the channel 202b were magnetically caught by a magnet set close to the channel 202b, and BB2 was introduced to flow through the channel 202b. BB2 was supplied at a pressure of 100 mbar for three minutes.

(4) PBS was supplied as the process liquid 21 (cleaning liquid) with the magnetic particles 26a caught in the channel 202b. PBS was supplied at a pressure of 80 mbar for three minutes.

(5) The magnet was moved away from the channel 202 to release the magnetic particles 26a from a magnetic force.

(6) A valve 31 for the fluid 24 and a valve 33 for the process liquid 21 were alternately opened and closed to alternately supply PBS as the process liquid 21 and air as the fluid 24 to the channel 202. An interposed region 28 was thereby formed by the fluid 24. The interposed region 28 was moved to the joint 203c to collect the magnetic particles 26a in the PBS as the process liquid 21. Five interposed regions 28 were formed. Air was supplied at a pressure of 70 mbar for three minutes.

(7) The collected sample liquid was measured by a flow cytometer. The amount of collected magnetic particles were compared by the number of detected singlets. Each singlet is a single magnetic particle 26 that passed through the detector of the flow cytometer.

The Reynolds number Re was calculated by Equation 1 to be 0.451 under the experimental condition, where the average flow velocity V was 0.002 m/s, the flow-path inner diameter d was approximately $0.2257 \times 10^{-3}$ m, and the dynamic viscosity was $1.0 \times 1010^{-6}$ m$^2$/s.

<Comparative Example>

In a comparative example, PBS was introduced instead of air as the fluid 24 in (6) and the magnetic particles 26a were collected. PBS was supplied at a pressure of 70 mbar for three minutes. Other processing performed in the comparative example was same as the embodiment.

Comparison of the collected amount (i.e., the number of detected magnetic particles 26a) is shown in FIG. 46. The number of detection (counted number) was 2630105 for the embodiment where conveyance was performed by the interface 23 using the fluid 24. The number of detection was 204077 for the comparative example. It was confirmed that the embodiment collected a larger number of magnetic particles 26a by about 12.9 times. It was confirmed that the method of processing a specimen according to the embodiment avoids remaining of the particles 22 in the flow-path 201.

The embodiments are disclosed totally as examples and not by means of limitation. The scope of the disclosure is defined not by the description on the embodiments but by the scope of the claims. Alterations (modifications) within the scope of the claims and the meaning of equivalency all fall within the scope of the disclosure.

What is claimed is:

1. A method of processing a specimen in which a target component in a specimen is processed using a specimen processing chip provided with a flow-path, the method comprising:
   intermittently introducing an air into the flow-path, in which a process liquid used for processing the target component flows, to form multiple air-phases each having interfaces dividing an air-phase and a liquid-phase, wherein the process liquid contains particles including the target component; and
   moving the interfaces along the flow-path to force the particles retained in the process liquid out of the specimen processing chip.

2. The method of processing a specimen according to claim 1, wherein the particles retained in the process liquid are forced out of the specimen processing chip by the air.

3. The method of processing a specimen according to claim 2, wherein the particles forced out of the specimen processing chip are counted by a flow cytometer.

4. The method of processing a specimen according to claim 1, wherein a number of the particles in the process liquid are from 100 thousand to 10 million.

5. The method of processing a specimen according to claim 1, wherein the interfaces are moved along the flow-path to convey the particles retained on an inner wall of the flow-path along the flow-path away from the inner wall.

6. The method of processing a specimen according to claim 5, wherein the interfaces are moved along the flow-path to contact the particles retained on the inner wall so as to move the particles away from the inner wall.

7. The method of processing a specimen according to claim 1, wherein an interface of the air is moved back and forth along the inner wall in a region in the flow-path where the particles are retained.

8. The method of processing a specimen according to claim 1, wherein the particles including the target component are liquid particles including the target component.

9. The method of processing a specimen according to claim 1, wherein the particles including the target component are solid carriers surficially bonded to the target component.

10. The method of processing a specimen according to claim 9, wherein the processing of the target component includes catching the carriers in the flow-path, and after catching the carriers, the carriers are released and moved by an interface of the air.

11. The method of processing a specimen according to claim 10, wherein the carriers are magnetic particles, and after magnetically catching the magnetic particles in the flow-path, the magnetic particles are then released from a magnetic force and moved by an interface of the air.

12. The method of processing a specimen according to claim 1, wherein the particles and the process liquid are introduced from an inlet joint for introducing fluid provided on an end of the flow-path,
   the target component included in the particles is processed in a channel of the flow-path, and
   the processed particles and the process liquid are conveyed to an outlet joint for discharging liquid provided on another end of the flow-path.

13. The method of processing a specimen according to claim 12, wherein the channel has a flow-path width larger than a flow-path width of the joint.

14. The method of processing a specimen according to claim 12, wherein a cross section of the channel has a larger width than a height.

15. The method of processing a specimen according to claim 1, wherein the target component is processed in a laminar flow in the flow-path.

16. The method of processing a specimen according to claim 1, wherein the target component is processed in a flow which has a Reynolds number of 2000 or below in the flow-path.

17. The method of processing a specimen according to claim 1, wherein the air introduced into the flow-path forms the interfaces entirely covering a flow-path cross section.

18. The method of processing a specimen according to claim 1, wherein the air is a liquid that separately stays in a phase different from the process liquid which is in contact, or a gas.

19. The method of processing a specimen according to claim 18, wherein:

when the process liquid is a water phase liquid, using an oil phase liquid or a gas as the fluid, and when the process liquid is the oil phase liquid, using the water phase liquid or the gas as the fluid.

20. A specimen processing apparatus for processing a target component in a specimen using a specimen processing chip, the apparatus comprising:

a chip base on which the specimen processing chip provided with a flow-path is provided; and an introducer for intermittently introducing an air into the flow-path, in which a process liquid used for processing the target component flows, of the specimen processing chip to form multiple air-phases each having interfaces dividing an air-phase and a liquid phase, wherein the process liquid contains particles including the target component, and the introducer moves the interfaces along the flow-path to force the particles retained in the process liquid out of the specimen processing chip.

* * * * *